US012799476B2

(12) United States Patent
Galonska et al.

(10) Patent No.: US 12,799,476 B2
(45) Date of Patent: Nov. 17, 2026

(54) METHODS, COMPOSITIONS, AND SYSTEMS FOR IDENTIFYING ANTIGEN-BINDING MOLECULES

(71) Applicant: 10x Genomics, Inc., Pleasanton, CA (US)

(72) Inventors: Christina Galonska, Stockholm (SE); Marlon Stoeckius, Stockholm (SE)

(73) Assignee: 10x Genomics, Inc.

( * ) Notice: Subject to any disclaimer, the term of this patent is extended or adjusted under 35 U.S.C. 154(b) by 524 days.

(21) Appl. No.: 18/683,075

(22) PCT Filed: Aug. 10, 2022

(86) PCT No.: PCT/US2022/039956

§ 371 (c)(1),
(2) Date: Feb. 12, 2024

(87) PCT Pub. No.: WO2023/018799

PCT Pub. Date: Feb. 16, 2023

(65) Prior Publication Data

US 2025/0019689 A1 Jan. 16, 2025

Related U.S. Application Data

(60) Provisional application No. 63/232,386, filed on Aug. 12, 2021.

(51) Int. Cl.
*C12N 15/10* (2006.01)

(52) U.S. Cl.
CPC ................................ *C12N 15/1065* (2013.01)

(58) Field of Classification Search
None
See application file for complete search history.

(56) References Cited

U.S. PATENT DOCUMENTS 4,514,388 A 4/1985 Psaledakis
4,683,195 A 7/1987 Mullis
4,683,202 A 7/1987 Mullis
4,800,159 A 1/1989 Mullis
4,883,867 A 11/1989 Lee
4,965,188 A 10/1990 Mullis
4,988,617 A 1/1991 Landegren et al.
5,002,882 A 3/1991 Lunnen
5,130,238 A 7/1992 Malek
5,308,751 A 5/1994 Ohkawa
5,321,130 A 6/1994 Yue
5,410,030 A 4/1995 Yue
5,436,134 A 7/1995 Haugland
5,455,166 A 10/1995 Walker
5,487,972 A 1/1996 Gelfand et al.
5,494,810 A 2/1996 Barany et al.
5,503,980 A 4/1996 Cantor
5,512,439 A 4/1996 Hornes
5,512,462 A 4/1996 Cheng
5,582,977 A 12/1996 Yue
5,599,675 A 2/1997 Brenner
5,641,658 A 6/1997 Adams
5,648,245 A 7/1997 Fire et al.
5,658,751 A 8/1997 Yue
5,695,940 A 12/1997 Drmanac et al.
5,750,341 A 5/1998 Macevicz
5,763,175 A 6/1998 Brenner
5,830,711 A 11/1998 Barany et al.
5,837,832 A 11/1998 Chee et al.
5,854,033 A 12/1998 Lizardi
5,863,753 A 1/1999 Haugland
5,871,921 A 2/1999 Landegren et al.
5,912,148 A 6/1999 Eggerding
5,925,545 A 7/1999 Reznikoff et al.
5,928,906 A 7/1999 Koester et al.
5,958,775 A 9/1999 Wickstrrom
5,962,271 A 10/1999 Chenchik et al.
5,962,272 A 10/1999 Chenchik et al.
5,965,443 A 10/1999 Reznikoff et al.
6,013,440 A 1/2000 Lipshutz
6,027,889 A 2/2000 Barany et al.
6,054,274 A 4/2000 Sampson et al.
6,060,240 A 5/2000 Kamb et al.
6,130,073 A 10/2000 Eggerding
6,143,496 A 11/2000 Brown
6,153,389 A 11/2000 Haarer
6,159,736 A 12/2000 Reznikoff et al.
6,165,714 A 12/2000 Lane et al.
6,210,891 B1 4/2001 Nyren
6,210,894 B1 4/2001 Brennan
6,214,587 B1 4/2001 Dattagupta
6,251,639 B1 6/2001 Kurn
6,258,568 B1 7/2001 Nyren
6,266,459 B1 7/2001 Walt
6,268,148 B1 7/2001 Barany et al.
6,274,320 B1 8/2001 Rothberg
6,291,180 B1 9/2001 Chu
6,291,187 B1 9/2001 Kingsmore et al.
6,300,063 B1 10/2001 Lipshutz et al.
6,309,824 B1 10/2001 Drmanac
6,323,009 B1 11/2001 Lasken et al.
6,344,316 B1 2/2002 Lockhart
6,344,329 B1 2/2002 Lizardi et al.
(Continued)

FOREIGN PATENT DOCUMENTS

AU 2003200718 10/2006
CN 1273609 11/2000
(Continued)

OTHER PUBLICATIONS

10x Genomics, "Assay Scheme and Configuration of Chromium™ Single Cell V(D)J Libraries," 10x Genomics, CG000109 Rev D, 2017, 10 pages.
(Continued)

*Primary Examiner* — Christopher M Gross
(74) *Attorney, Agent, or Firm* — Fish & Richardson P.C.

(57) ABSTRACT

Provided herein are methods, compositions, and kits including single-chain antibody nucleic acid libraries and methods of displaying single-chain antibodies and screening single-chain antibodies on a spatial array.

20 Claims, 7 Drawing Sheets

(56) References Cited

U.S. PATENT DOCUMENTS

| | | | |
|---|---|---|---|
| 6,355,431 | B1 | 3/2002 | Chee |
| 6,368,801 | B1 | 4/2002 | Faruqi |
| 6,401,267 | B1 | 6/2002 | Drmanac |
| 6,404,907 | B1 | 6/2002 | Gilchrist |
| 6,432,360 | B1 | 8/2002 | Church et al. |
| 6,503,713 | B1 | 1/2003 | Rana |
| 6,506,561 | B1 | 1/2003 | Cheval et al. |
| 6,534,266 | B1 | 3/2003 | Singer |
| 6,544,732 | B1 | 4/2003 | Chee |
| 6,573,043 | B1 | 6/2003 | Cohen et al. |
| 6,579,695 | B1 | 6/2003 | Lambalot |
| 6,620,584 | B1 | 9/2003 | Chee |
| 6,632,641 | B1 | 10/2003 | Brennan |
| 6,737,236 | B1 | 5/2004 | Pieken et al. |
| 6,770,441 | B2 | 8/2004 | Dickinson |
| 6,773,886 | B2 | 8/2004 | Kaufman |
| 6,787,308 | B2 | 9/2004 | Balasubramanian |
| 6,797,470 | B2 | 9/2004 | Barany et al. |
| 6,800,453 | B2 | 10/2004 | Labaer |
| 6,812,005 | B2 | 11/2004 | Fan et al. |
| 6,828,100 | B1 | 12/2004 | Ronaghi |
| 6,833,246 | B2 | 12/2004 | Balasubramanian |
| 6,852,487 | B1 | 2/2005 | Barany et al. |
| 6,859,570 | B2 | 2/2005 | Walt |
| 6,864,052 | B1 | 3/2005 | Drmanac |
| 6,867,028 | B2 | 3/2005 | Janulaitis |
| 6,872,816 | B1 | 3/2005 | Hall et al. |
| 6,875,572 | B2 | 4/2005 | Prudent et al. |
| 6,890,741 | B2 | 5/2005 | Fan et al. |
| 6,897,023 | B2 | 5/2005 | Fu |
| 6,913,881 | B1 | 7/2005 | Aizenstein et al. |
| 6,942,968 | B1 | 9/2005 | Dickinson et al. |
| 7,011,944 | B2 | 3/2006 | Prudent et al. |
| 7,057,026 | B2 | 6/2006 | Barnes |
| 7,083,980 | B2 | 8/2006 | Reznikoff et al. |
| 7,115,400 | B1 | 10/2006 | Adessi |
| 7,118,883 | B2 | 10/2006 | Inoue |
| 7,166,431 | B2 | 1/2007 | Chee et al. |
| 7,192,735 | B2 | 3/2007 | Lambalot |
| 7,211,414 | B2 | 5/2007 | Hardin |
| 7,255,994 | B2 | 8/2007 | Lao |
| 7,258,976 | B2 | 8/2007 | Mitsuhashi |
| 7,282,328 | B2 | 10/2007 | Kong et al. |
| 7,297,518 | B2 | 11/2007 | Quake |
| 7,329,492 | B2 | 2/2008 | Hardin |
| 7,358,047 | B2 | 4/2008 | Hafner et al. |
| 7,361,488 | B2 | 4/2008 | Fan et al. |
| 7,378,242 | B2 | 5/2008 | Hurt |
| 7,393,665 | B2 | 7/2008 | Brenner |
| 7,405,281 | B2 | 7/2008 | Xu |
| 7,407,757 | B2 | 8/2008 | Brenner |
| 7,473,767 | B2 | 1/2009 | Dimitrov |
| 7,499,806 | B2 | 3/2009 | Kermani et al. |
| 7,537,897 | B2 | 5/2009 | Brenner |
| 7,563,576 | B2 | 7/2009 | Chee |
| 7,579,153 | B2 | 8/2009 | Brenner |
| 7,582,420 | B2 | 9/2009 | Oliphant et al. |
| 7,601,498 | B2 | 10/2009 | Mao |
| 7,608,434 | B2 | 10/2009 | Reznikoff et al. |
| 7,611,869 | B2 | 11/2009 | Fan |
| 7,635,566 | B2 | 12/2009 | Brenner |
| 7,666,612 | B2 | 2/2010 | Johnsson |
| 7,674,752 | B2 | 3/2010 | He |
| 7,709,198 | B2 | 5/2010 | Luo et al. |
| 7,776,547 | B2 | 8/2010 | Roth |
| 7,776,567 | B2 | 8/2010 | Mao |
| 7,803,943 | B2 | 9/2010 | Mao |
| 7,888,009 | B2 | 2/2011 | Barany et al. |
| 7,892,747 | B2 | 2/2011 | Barany et al. |
| 7,910,304 | B2 | 3/2011 | Drmanac |
| 7,914,981 | B2 | 3/2011 | Barany et al. |
| 7,955,794 | B2 | 6/2011 | Shen et al. |
| 7,960,119 | B2 | 6/2011 | Chee |
| 7,985,565 | B2 | 7/2011 | Mayer et al. |
| 8,003,354 | B2 | 8/2011 | Shen et al. |
| 8,076,063 | B2 | 12/2011 | Fan |
| 8,092,784 | B2 | 1/2012 | Mao |
| 8,148,068 | B2 | 4/2012 | Brenner |
| 8,206,917 | B2 | 6/2012 | Chee |
| 8,268,554 | B2 | 9/2012 | Schallmeiner |
| 8,288,103 | B2 | 10/2012 | Oliphant |
| 8,288,122 | B2 | 10/2012 | O'Leary et al. |
| 8,383,338 | B2 | 2/2013 | Kitzman |
| 8,431,691 | B2 | 4/2013 | McKernan et al. |
| 8,460,865 | B2 | 6/2013 | Chee |
| 8,481,257 | B2 | 7/2013 | Van Eijk |
| 8,481,258 | B2 | 7/2013 | Church et al. |
| 8,481,292 | B2 | 7/2013 | Casbon |
| 8,481,698 | B2 | 7/2013 | Lieberman et al. |
| 8,507,204 | B2 | 8/2013 | Pierce et al. |
| 8,519,115 | B2 | 8/2013 | Webster et al. |
| 8,551,710 | B2 | 10/2013 | Bernitz et al. |
| 8,568,979 | B2 | 10/2013 | Stuelpnagel et al. |
| 8,586,310 | B2 | 11/2013 | Mitra |
| 8,597,891 | B2 | 12/2013 | Barany et al. |
| 8,603,743 | B2 | 12/2013 | Liu et al. |
| 8,604,182 | B2 | 12/2013 | Luo et al. |
| 8,614,073 | B2 | 12/2013 | Van Eijk |
| 8,624,016 | B2 | 1/2014 | Barany et al. |
| 8,685,889 | B2 | 4/2014 | Van Eijk |
| 8,741,564 | B2 | 6/2014 | Seligmann |
| 8,741,606 | B2 | 6/2014 | Casbon |
| 8,771,950 | B2 | 7/2014 | Church et al. |
| 8,785,353 | B2 | 7/2014 | Van Eijk |
| 8,790,873 | B2 | 7/2014 | Namsaraev et al. |
| 8,809,238 | B2 | 8/2014 | Livak et al. |
| 8,815,512 | B2 | 8/2014 | Van Eijk |
| 8,835,358 | B2 | 9/2014 | Fodor |
| 8,865,410 | B2 | 10/2014 | Shendure |
| 8,906,626 | B2 | 12/2014 | Oliphant et al. |
| 8,911,945 | B2 | 12/2014 | Van Eijk |
| 8,936,912 | B2 | 1/2015 | Mitra |
| 8,951,726 | B2 | 2/2015 | Luo et al. |
| 8,951,728 | B2 | 2/2015 | Rasmussen |
| 8,986,926 | B2 | 3/2015 | Ferree et al. |
| 9,005,891 | B2 | 4/2015 | Sinicropi et al. |
| 9,005,935 | B2 | 4/2015 | Belyaev |
| 9,023,768 | B2 | 5/2015 | Van Eijk |
| 9,062,348 | B1 | 6/2015 | Van Eijk |
| 9,080,210 | B2 | 7/2015 | Van Eijk |
| 9,194,001 | B2 | 11/2015 | Brenner |
| 9,201,063 | B2 | 12/2015 | Sood et al. |
| 9,273,349 | B2 | 3/2016 | Nguyen et al. |
| 9,290,808 | B2 | 3/2016 | Fodor |
| 9,290,809 | B2 | 3/2016 | Fodor |
| 9,328,383 | B2 | 5/2016 | Van Eijk |
| 9,330,295 | B2 | 5/2016 | Dunn |
| 9,334,536 | B2 | 5/2016 | Van Eijk |
| 9,371,563 | B2 | 6/2016 | Geiss et al. |
| 9,371,598 | B2 | 6/2016 | Chee |
| 9,376,716 | B2 | 6/2016 | Van Eijk |
| 9,376,717 | B2 | 6/2016 | Gao et al. |
| 9,376,719 | B2 | 6/2016 | Van Eijk |
| 9,416,409 | B2 | 8/2016 | Hayden |
| 9,447,459 | B2 | 9/2016 | Van Eijk |
| 9,453,256 | B2 | 9/2016 | Van Eijk |
| 9,493,820 | B2 | 11/2016 | Van Eijk |
| 9,506,061 | B2 | 11/2016 | Brown et al. |
| 9,512,422 | B2 | 12/2016 | Barnard et al. |
| 9,574,230 | B2 | 2/2017 | Van Eijk |
| 9,593,365 | B2 | 3/2017 | Frisen et al. |
| 9,598,728 | B2 | 3/2017 | Barany et al. |
| 9,624,538 | B2 | 4/2017 | Church et al. |
| 9,644,204 | B2 | 5/2017 | Hindson et al. |
| 9,657,335 | B2 | 5/2017 | Van Eijk |
| 9,670,542 | B2 | 6/2017 | Van Eijk |
| 9,694,361 | B2 | 7/2017 | Bharadwaj |
| 9,702,004 | B2 | 7/2017 | Van Eijk |
| 9,714,446 | B2 | 7/2017 | Webster et al. |
| 9,714,937 | B2 | 7/2017 | Dunaway |
| 9,727,810 | B2 | 8/2017 | Fodor et al. |
| 9,745,627 | B2 | 8/2017 | Van Eijk |
| 9,777,324 | B2 | 10/2017 | Van Eijk |
| 9,783,841 | B2 | 10/2017 | Nolan et al. |

(56) References Cited

U.S. PATENT DOCUMENTS

| | | | |
|---|---|---|---|
| 9,790,476 | B2 | 10/2017 | Gloeckner et al. |
| 9,816,134 | B2 | 11/2017 | Namsaraev |
| 9,834,814 | B2 | 12/2017 | Peter et al. |
| 9,850,536 | B2 | 12/2017 | Oliphant et al. |
| 9,856,521 | B2 | 1/2018 | Stevens et al. |
| 9,868,979 | B2 | 1/2018 | Chee et al. |
| 9,879,313 | B2 | 1/2018 | Chee et al. |
| 9,896,721 | B2 | 2/2018 | Van Eijk |
| 9,898,576 | B2 | 2/2018 | Van Eijk |
| 9,898,577 | B2 | 2/2018 | Van Eijk |
| 9,902,991 | B2 | 2/2018 | Sinicropi et al. |
| 9,909,167 | B2 | 3/2018 | Samusik et al. |
| 9,938,566 | B2 | 4/2018 | Shepard et al. |
| 9,957,550 | B2 | 5/2018 | Yeakley et al. |
| 10,002,316 | B2 | 6/2018 | Fodor et al. |
| 10,023,907 | B2 | 7/2018 | Van Eijk |
| 10,030,261 | B2 | 7/2018 | Frisen et al. |
| 10,035,992 | B2 | 7/2018 | Gloeckner et al. |
| 10,041,949 | B2 | 8/2018 | Bendall et al. |
| 10,059,989 | B2 | 8/2018 | Giresi et al. |
| 10,059,990 | B2 | 8/2018 | Boyden et al. |
| 10,095,832 | B2 | 10/2018 | Van Eijk |
| 10,101,336 | B2 | 10/2018 | Bergo |
| 10,144,966 | B2 | 12/2018 | Cantor |
| 10,208,982 | B2 | 2/2019 | Bannish et al. |
| 10,227,639 | B2 | 3/2019 | Levner et al. |
| 10,273,541 | B2 | 4/2019 | Hindson et al. |
| 10,308,982 | B2 | 6/2019 | Chee |
| 10,357,771 | B2 | 7/2019 | Bharadwaj |
| 10,370,698 | B2 | 8/2019 | Nolan et al. |
| 10,415,080 | B2 | 9/2019 | Dunaway et al. |
| 10,465,235 | B2 | 11/2019 | Gullberg et al. |
| 10,472,669 | B2 | 11/2019 | Chee |
| 10,480,022 | B2 | 11/2019 | Chee |
| 10,480,029 | B2 | 11/2019 | Bent et al. |
| 10,494,667 | B2 | 12/2019 | Chee |
| 10,495,554 | B2 | 12/2019 | Deisseroth et al. |
| 10,501,777 | B2 | 12/2019 | Beechem et al. |
| 10,501,791 | B2 | 12/2019 | Church et al. |
| 10,510,435 | B2 | 12/2019 | Cai et al. |
| 10,544,403 | B2 | 1/2020 | Gloeckner et al. |
| 10,550,429 | B2 | 2/2020 | Harada et al. |
| 10,590,244 | B2 | 3/2020 | Delaney et al. |
| 10,633,648 | B2 | 4/2020 | Seelig et al. |
| 10,640,816 | B2 | 5/2020 | Beechem et al. |
| 10,640,826 | B2 | 5/2020 | Church et al. |
| 10,662,466 | B2 | 5/2020 | Berry et al. |
| 10,662,468 | B2 | 5/2020 | Chee |
| 10,669,569 | B2 | 6/2020 | Gullberg et al. |
| 10,724,078 | B2 | 7/2020 | Van Driel et al. |
| 10,725,027 | B2 | 7/2020 | Bell |
| 10,774,372 | B2 | 9/2020 | Chee et al. |
| 10,774,374 | B2 | 9/2020 | Frisen et al. |
| 10,787,701 | B2 | 9/2020 | Chee |
| 10,815,519 | B2 | 10/2020 | Husain et al. |
| 10,829,803 | B2 | 11/2020 | Terbrueggen et al. |
| 10,844,426 | B2 | 11/2020 | Daugharthy et al. |
| 10,858,698 | B2 | 12/2020 | Church et al. |
| 10,858,702 | B2 | 12/2020 | Lucero et al. |
| 10,913,975 | B2 | 2/2021 | So et al. |
| 10,914,730 | B2 | 2/2021 | Chee et al. |
| 10,927,403 | B2 | 2/2021 | Chee et al. |
| 10,961,566 | B2 | 3/2021 | Chee |
| 11,001,879 | B1 | 5/2021 | Chee |
| 11,008,607 | B2 | 5/2021 | Chee |
| 11,046,996 | B1 | 6/2021 | Chee et al. |
| 11,067,567 | B2 | 7/2021 | Chee |
| 11,104,936 | B2 | 8/2021 | Zhang et al. |
| 11,118,216 | B2 | 9/2021 | Koshinsky et al. |
| 11,156,603 | B2 | 10/2021 | Chee |
| 11,162,132 | B2 | 11/2021 | Frisen et al. |
| 11,208,684 | B2 | 12/2021 | Chee |
| 11,214,796 | B2 | 1/2022 | Shirai et al. |
| 11,286,515 | B2 | 3/2022 | Chee et al. |
| 11,293,917 | B2 | 4/2022 | Chee |
| 11,299,774 | B2 | 4/2022 | Frisen et al. |
| 11,313,856 | B2 | 4/2022 | Chee |
| 11,332,790 | B2 | 5/2022 | Chell et al. |
| 11,352,659 | B2 | 6/2022 | Frisen et al. |
| 11,352,667 | B2 | 6/2022 | Hauling et al. |
| 11,359,228 | B2 | 6/2022 | Chee et al. |
| 11,365,442 | B2 | 6/2022 | Chee |
| 11,371,086 | B2 | 6/2022 | Chee |
| 11,384,386 | B2 | 7/2022 | Chee |
| 11,390,912 | B2 | 7/2022 | Frisen et al. |
| 11,401,545 | B2 | 8/2022 | Chee |
| 11,407,992 | B2 | 8/2022 | Dadhwal |
| 11,408,029 | B2 | 8/2022 | Katiraee et al. |
| 11,434,524 | B2 | 9/2022 | Ramachandran Iyer et al. |
| 11,459,607 | B1 | 10/2022 | Terry et al. |
| 11,479,809 | B2 | 10/2022 | Frisen et al. |
| 11,479,810 | B1 | 10/2022 | Chee |
| 11,492,612 | B1 | 11/2022 | Dadhwal |
| 11,501,440 | B2 | 11/2022 | Weisenfeld et al. |
| 11,505,828 | B2 | 11/2022 | Chell et al. |
| 11,512,308 | B2 | 11/2022 | Gallant et al. |
| 11,519,022 | B2 | 12/2022 | Chee |
| 11,519,033 | B2 | 12/2022 | Schnall-Levin et al. |
| 11,530,438 | B2 | 12/2022 | Persson et al. |
| 11,535,887 | B2 | 12/2022 | Gallant et al. |
| 11,542,543 | B2 | 1/2023 | Chee |
| 11,549,138 | B2 | 1/2023 | Chee |
| 11,560,587 | B2 | 1/2023 | Chee |
| 11,560,592 | B2 | 1/2023 | Chew et al. |
| 11,560,593 | B2 | 1/2023 | Chell et al. |
| 11,592,447 | B2 | 2/2023 | Uytingco et al. |
| 11,608,498 | B2 | 3/2023 | Gallant et al. |
| 11,608,520 | B2 | 3/2023 | Galonska et al. |
| 11,613,773 | B2 | 3/2023 | Frisen et al. |
| 11,618,897 | B2 | 4/2023 | Kim et al. |
| 11,618,918 | B2 | 4/2023 | Chee et al. |
| 11,624,063 | B2 | 4/2023 | Dadhwal |
| 11,624,086 | B2 | 4/2023 | Uytingco et al. |
| 11,634,756 | B2 | 4/2023 | Chee |
| 11,649,485 | B2 | 5/2023 | Yin et al. |
| 11,661,626 | B2 | 5/2023 | Katiraee et al. |
| 11,680,260 | B2 | 6/2023 | Kim et al. |
| 11,692,218 | B2 | 7/2023 | Engblom et al. |
| 11,702,693 | B2 | 7/2023 | Bharadwaj |
| 11,702,698 | B2 | 7/2023 | Stoeckius |
| 11,713,480 | B2 | 8/2023 | Lee |
| 11,732,292 | B2 | 8/2023 | Chee |
| 11,732,299 | B2 | 8/2023 | Ramachandran Iyer |
| 11,732,300 | B2 | 8/2023 | Bava |
| 11,733,238 | B2 | 8/2023 | Chee |
| 11,739,372 | B2 | 8/2023 | Frisen et al. |
| 11,739,381 | B2 | 8/2023 | Chew et al. |
| 11,753,673 | B2 | 9/2023 | Chew et al. |
| 11,753,674 | B2 | 9/2023 | Chee et al. |
| 11,753,675 | B2 | 9/2023 | Ramachandran Iyer |
| 11,761,030 | B2 | 9/2023 | Chee |
| 11,761,038 | B1 | 9/2023 | Stoeckius |
| 11,767,550 | B2 | 9/2023 | Chee |
| 11,768,175 | B1 | 9/2023 | Kim et al. |
| 11,773,433 | B2 | 10/2023 | Gallant et al. |
| 11,781,130 | B2 | 10/2023 | Dadhwal |
| 11,788,122 | B2 | 10/2023 | Frisen et al. |
| 11,795,498 | B2 | 10/2023 | Frisen et al. |
| 11,795,507 | B2 | 10/2023 | Chell et al. |
| 11,808,769 | B2 | 11/2023 | Uytingco et al. |
| 11,821,024 | B2 | 11/2023 | Chee et al. |
| 11,821,035 | B1 | 11/2023 | Bent et al. |
| 11,827,935 | B1 | 11/2023 | Ramachandran Iyer et al. |
| 11,835,462 | B2 | 12/2023 | Bava |
| 11,840,687 | B2 | 12/2023 | Gallant et al. |
| 11,840,724 | B2 | 12/2023 | Chew et al. |
| 11,845,979 | B2 | 12/2023 | Engblom et al. |
| 11,859,178 | B2 | 1/2024 | Gallant et al. |
| 11,866,767 | B2 | 1/2024 | Uytingco et al. |
| 11,866,770 | B2 | 1/2024 | Chee |
| 11,873,482 | B2 | 1/2024 | Kim et al. |
| 11,891,654 | B2 | 2/2024 | Alvarado Martinez et al. |
| 11,898,205 | B2 | 2/2024 | Bava |
| 11,926,822 | B1 | 3/2024 | Gohil et al. |

(56) References Cited

U.S. PATENT DOCUMENTS

| | | | |
|---|---|---|---|
| 11,926,863 | B1 | 3/2024 | Boutet |
| 11,926,867 | B2 | 3/2024 | Yin et al. |
| 11,933,957 | B1 | 3/2024 | Tentori et al. |
| 11,952,627 | B2 | 4/2024 | Stoeckius |
| 11,959,076 | B2 | 4/2024 | Kim et al. |
| 11,959,130 | B2 | 4/2024 | Galonska et al. |
| 11,965,213 | B2 | 4/2024 | Williams |
| 11,970,739 | B2 | 4/2024 | Chew et al. |
| 11,981,958 | B1 | 5/2024 | Galonska |
| 11,981,960 | B1 | 5/2024 | Lin et al. |
| 11,981,965 | B2 | 5/2024 | Chell et al. |
| RE50,065 | E | 7/2024 | Frisen et al. |
| 12,024,741 | B2 | 7/2024 | Tentori et al. |
| 12,031,177 | B1 | 7/2024 | Tentori et al. |
| 12,060,604 | B2 | 8/2024 | Katiraee et al. |
| 12,071,655 | B2 | 8/2024 | Sukovich et al. |
| 12,076,701 | B2 | 9/2024 | Bava |
| 12,098,417 | B2 | 9/2024 | Engblom et al. |
| 12,098,985 | B2 | 9/2024 | Cox et al. |
| 12,110,541 | B2 | 10/2024 | Bava |
| 12,117,439 | B2 | 10/2024 | Delaney et al. |
| 12,128,403 | B2 | 10/2024 | Kim et al. |
| 12,129,516 | B2 | 10/2024 | Tentori et al. |
| 12,157,124 | B2 | 12/2024 | Cox et al. |
| 12,180,543 | B2 | 12/2024 | Uytingco et al. |
| 12,195,790 | B2 | 1/2025 | Sukovich et al. |
| 12,203,134 | B2 | 1/2025 | Nagendran et al. |
| 12,209,280 | B1 | 1/2025 | Mignardi et al. |
| D1,064,308 | S | 2/2025 | Alimsijah et al. |
| 12,223,751 | B2 | 2/2025 | Lin et al. |
| 12,228,544 | B2 | 2/2025 | Kim et al. |
| 12,234,505 | B2 | 2/2025 | Chee |
| 12,241,060 | B2 | 3/2025 | Kim et al. |
| 12,241,890 | B2 | 3/2025 | Delaney et al. |
| 12,249,085 | B2 | 3/2025 | Tentori et al. |
| 12,265,079 | B1 | 4/2025 | Bent |
| 12,270,077 | B2 | 4/2025 | Schnall-Levin et al. |
| 12,275,988 | B2 | 4/2025 | Galonska et al. |
| 12,281,357 | B1 | 4/2025 | Tentori et al. |
| 12,286,673 | B2 | 4/2025 | Bava |
| 12,287,264 | B2 | 4/2025 | Cox et al. |
| 12,297,486 | B2 | 5/2025 | Patterson et al. |
| 12,297,487 | B2 | 5/2025 | Chee |
| 12,297,488 | B2 | 5/2025 | Chee |
| 12,344,892 | B2 | 7/2025 | Schnall-Levin et al. |
| 12,365,935 | B2 | 7/2025 | Chew et al. |
| 12,365,942 | B2 | 7/2025 | Stoeckius |
| 12,371,688 | B2 | 7/2025 | Kim et al. |
| 12,378,607 | B2 | 8/2025 | Schnall-Levin et al. |
| 12,385,083 | B2 | 8/2025 | Shah |
| 12,391,979 | B2 | 8/2025 | Chee |
| 12,391,980 | B2 | 8/2025 | Chee |
| 12,399,123 | B1 | 8/2025 | Shah et al. |
| 12,404,544 | B2 | 9/2025 | Tentori et al. |
| 12,405,264 | B2 | 9/2025 | Stoeckius |
| 12,416,603 | B2 | 9/2025 | Tentori et al. |
| 12,435,363 | B1 | 10/2025 | Gallant et al. |
| 12,442,045 | B2 | 10/2025 | Williams |
| 12,497,654 | B2 | 12/2025 | Ramachandran Iyer et al. |
| 12,508,590 | B2 | 12/2025 | Kim et al. |
| D1,108,656 | S | 1/2026 | Alimsijah et al. |
| 12,529,094 | B2 | 1/2026 | Bent et al. |
| 12,545,949 | B2 | 2/2026 | Bent et al. |
| 12,553,805 | B2 | 2/2026 | Shahjamali |
| 12,553,898 | B1 | 2/2026 | Uytingco et al. |
| 12,566,113 | B2 | 3/2026 | Delaney et al. |
| 12,566,114 | B2 | 3/2026 | Cox et al. |
| 12,571,029 | B1 | 3/2026 | Galonska et al. |
| 12,668,835 | B1 | 6/2026 | Tentori et al. |
| 12,692,492 | B2 | 7/2026 | Gallant et al. |
| 2001/0055764 | A1 | 12/2001 | Empendocles et al. |
| 2002/0040275 | A1 | 4/2002 | Cravatt |
| 2002/0051986 | A1 | 5/2002 | Baez et al. |
| 2002/0055100 | A1 | 5/2002 | Kawashima |
| 2002/0058250 | A1 | 5/2002 | Firth |
| 2002/0086441 | A1 | 7/2002 | Baranov et al. |
| 2002/0164611 | A1 | 11/2002 | Bamdad |
| 2003/0017451 | A1 | 1/2003 | Wang et al. |
| 2003/0022207 | A1 | 1/2003 | Balasubramanian |
| 2003/0064398 | A1 | 4/2003 | Barnes |
| 2003/0092624 | A1 | 5/2003 | Wang et al. |
| 2003/0138879 | A1 | 7/2003 | Lambalot |
| 2003/0148335 | A1 | 8/2003 | Shen et al. |
| 2003/0162216 | A1 | 8/2003 | Gold |
| 2003/0165948 | A1 | 9/2003 | Alsmadi et al. |
| 2003/0211489 | A1 | 11/2003 | Shen et al. |
| 2003/0224419 | A1 | 12/2003 | Corcoran |
| 2003/0232348 | A1 | 12/2003 | Jones et al. |
| 2003/0232382 | A1 | 12/2003 | Brennan |
| 2003/0235854 | A1 | 12/2003 | Chan et al. |
| 2004/0009487 | A1 | 1/2004 | Kadushin et al. |
| 2004/0033499 | A1 | 2/2004 | Ilsley et al. |
| 2004/0067492 | A1 | 4/2004 | Peng et al. |
| 2004/0082059 | A1 | 4/2004 | Webb et al. |
| 2004/0096853 | A1 | 5/2004 | Mayer |
| 2004/0101835 | A1 | 5/2004 | Willis et al. |
| 2004/0106110 | A1 | 6/2004 | Balasubramanian |
| 2004/0235103 | A1 | 11/2004 | Reznikoff et al. |
| 2004/0241660 | A1 | 12/2004 | Wojtowicz et al. |
| 2004/0248325 | A1 | 12/2004 | Bukusoglu et al. |
| 2004/0259105 | A1 | 12/2004 | Fan et al. |
| 2005/0003431 | A1 | 1/2005 | Wucherpfennig |
| 2005/0014203 | A1 | 1/2005 | Darfler et al. |
| 2005/0037393 | A1 | 2/2005 | Gunderson et al. |
| 2005/0048498 | A1 | 3/2005 | Woudenberg et al. |
| 2005/0048580 | A1 | 3/2005 | Labaer |
| 2005/0064460 | A1 | 3/2005 | Holliger et al. |
| 2005/0095627 | A1 | 5/2005 | Kolman et al. |
| 2005/0100900 | A1 | 5/2005 | Kawashima et al. |
| 2005/0130173 | A1 | 6/2005 | Leamon et al. |
| 2005/0136414 | A1 | 6/2005 | Gunderson et al. |
| 2005/0164292 | A1 | 7/2005 | Farooqui |
| 2005/0170373 | A1 | 8/2005 | Monforte |
| 2005/0191656 | A1 | 9/2005 | Drmanac et al. |
| 2005/0191698 | A1 | 9/2005 | Chee et al. |
| 2005/0202433 | A1 | 9/2005 | Van Beuningen |
| 2005/0227271 | A1 | 10/2005 | Kwon |
| 2005/0239119 | A1 | 10/2005 | Tsukada et al. |
| 2005/0260653 | A1 | 11/2005 | LaBaer |
| 2005/0266417 | A1 | 12/2005 | Barany et al. |
| 2006/0041385 | A1 | 2/2006 | Bauer et al. |
| 2006/0046313 | A1 | 3/2006 | Roth |
| 2006/0084078 | A1 | 4/2006 | Zhao |
| 2006/0105352 | A1 | 5/2006 | Qiao et al. |
| 2006/0154286 | A1 | 7/2006 | Kong et al. |
| 2006/0188901 | A1 | 8/2006 | Barnes et al. |
| 2006/0199183 | A1 | 9/2006 | Valat et al. |
| 2006/0211001 | A1 | 9/2006 | Yu et al. |
| 2006/0216775 | A1 | 9/2006 | Burkart et al. |
| 2006/0240439 | A1 | 10/2006 | Smith et al. |
| 2006/0263789 | A1 | 11/2006 | Kincaid |
| 2006/0275782 | A1 | 12/2006 | Gunderson et al. |
| 2006/0281109 | A1 | 12/2006 | Barr Ost et al. |
| 2007/0020640 | A1 | 1/2007 | McCloskey et al. |
| 2007/0020669 | A1 | 1/2007 | Ericsson |
| 2007/0026430 | A1 | 2/2007 | Andersen et al. |
| 2007/0054288 | A1 | 3/2007 | Su et al. |
| 2007/0087360 | A1 | 4/2007 | Boyd |
| 2007/0099208 | A1 | 5/2007 | Drmanac et al. |
| 2007/0128624 | A1 | 6/2007 | Gormley et al. |
| 2007/0128656 | A1 | 6/2007 | Agrawal |
| 2007/0134723 | A1 | 6/2007 | Kozlov et al. |
| 2007/0161020 | A1 | 7/2007 | Luo et al. |
| 2007/0166705 | A1 | 7/2007 | Milton et al. |
| 2007/0172873 | A1 | 7/2007 | Brenner et al. |
| 2007/0207482 | A1 | 9/2007 | Church et al. |
| 2007/0254305 | A1 | 11/2007 | Paik et al. |
| 2007/0269805 | A1 | 11/2007 | Hogers |
| 2008/0003586 | A1 | 1/2008 | Hyde et al. |
| 2008/0009420 | A1 | 1/2008 | Schroth et al. |
| 2008/0108082 | A1 | 5/2008 | Rank et al. |
| 2008/0108804 | A1 | 5/2008 | Hayashizaki et al. |
| 2008/0132429 | A1 | 6/2008 | Perov et al. |
| 2008/0160580 | A1 | 7/2008 | Adessi et al. |

(56) References Cited

U.S. PATENT DOCUMENTS

| | | | |
|---|---|---|---|
| 2008/0220434 | A1 | 9/2008 | Thomas |
| 2008/0261204 | A1 | 10/2008 | Lexow |
| 2008/0286795 | A1 | 11/2008 | Kawashima et al. |
| 2008/0293046 | A1 | 11/2008 | Allawi et al. |
| 2009/0005252 | A1 | 1/2009 | Drmanac et al. |
| 2009/0006002 | A1 | 1/2009 | Honisch et al. |
| 2009/0018024 | A1 | 1/2009 | Church et al. |
| 2009/0026082 | A1 | 1/2009 | Rothberg et al. |
| 2009/0036323 | A1 | 2/2009 | van Eijk et al. |
| 2009/0082212 | A1 | 3/2009 | Williams |
| 2009/0099041 | A1 | 4/2009 | Church et al. |
| 2009/0105959 | A1 | 4/2009 | Braverman et al. |
| 2009/0117573 | A1 | 5/2009 | Fu et al. |
| 2009/0127589 | A1 | 5/2009 | Rothberg et al. |
| 2009/0155781 | A1 | 6/2009 | Drmanac et al. |
| 2009/0170713 | A1 | 7/2009 | van Eijk et al. |
| 2009/0202998 | A1 | 8/2009 | Schlumpberger et al. |
| 2009/0233802 | A1 | 9/2009 | Bignell et al. |
| 2009/0253581 | A1 | 10/2009 | van Eijk et al. |
| 2009/0270273 | A1 | 10/2009 | Burns et al. |
| 2009/0283407 | A1 | 11/2009 | Shah et al. |
| 2009/0286249 | A1 | 11/2009 | Bekcer et al. |
| 2009/0291854 | A1 | 11/2009 | Weisinger-Mayr et al. |
| 2009/0312193 | A1 | 12/2009 | Kim et al. |
| 2010/0035249 | A1 | 2/2010 | Hayashizaki et al. |
| 2010/0047790 | A1 | 2/2010 | Southern et al. |
| 2010/0069263 | A1 | 3/2010 | Shendure et al. |
| 2010/0105052 | A1 | 4/2010 | Drmanac et al. |
| 2010/0120097 | A1 | 5/2010 | Matz et al. |
| 2010/0120098 | A1 | 5/2010 | Grunenwald et al. |
| 2010/0129874 | A1 | 5/2010 | Mitra et al. |
| 2010/0145037 | A1 | 6/2010 | Brive et al. |
| 2010/0173384 | A1 | 7/2010 | Johnsson et al. |
| 2010/0184618 | A1 | 7/2010 | Namsaraev et al. |
| 2010/0210475 | A1 | 8/2010 | Lee et al. |
| 2010/0227329 | A1 | 9/2010 | Cuppens |
| 2010/0273219 | A1 | 10/2010 | May et al. |
| 2011/0028685 | A1 | 2/2011 | Purkayastha et al. |
| 2011/0031123 | A1 | 2/2011 | Schulze et al. |
| 2011/0033854 | A1 | 2/2011 | Drmanac et al. |
| 2011/0045462 | A1 | 2/2011 | Fu et al. |
| 2011/0059436 | A1 | 3/2011 | Hardin et al. |
| 2011/0111409 | A1 | 5/2011 | Sinicropi et al. |
| 2011/0152111 | A1 | 6/2011 | Fan et al. |
| 2011/0237449 | A1 | 9/2011 | McMaster et al. |
| 2011/0245101 | A1 | 10/2011 | Chee et al. |
| 2011/0245111 | A1 | 10/2011 | Chee |
| 2011/0269631 | A1 | 11/2011 | Fu et al. |
| 2011/0287435 | A1 | 11/2011 | Grunenwald et al. |
| 2012/0021930 | A1 | 1/2012 | Schoen et al. |
| 2012/0046175 | A1 | 2/2012 | Rodesch et al. |
| 2012/0046178 | A1 | 2/2012 | Van Den Boom et al. |
| 2012/0065081 | A1 | 3/2012 | Chee |
| 2012/0135871 | A1 | 5/2012 | van Eijk et al. |
| 2012/0202698 | A1 | 8/2012 | van Eijk et al. |
| 2012/0202704 | A1 | 8/2012 | Fan et al. |
| 2012/0220479 | A1 | 8/2012 | Ericsson et al. |
| 2012/0245053 | A1 | 9/2012 | Shirai et al. |
| 2012/0252702 | A1 | 10/2012 | Muratani et al. |
| 2012/0258871 | A1 | 10/2012 | Kozlov et al. |
| 2012/0289414 | A1 | 11/2012 | Mitra et al. |
| 2012/0301925 | A1 | 11/2012 | Belyaev |
| 2013/0005594 | A1 | 1/2013 | Terbrueggen et al. |
| 2013/0005600 | A1 | 1/2013 | Olek |
| 2013/0023433 | A1 | 1/2013 | Luo et al. |
| 2013/0035239 | A1 | 2/2013 | Kong et al. |
| 2013/0040842 | A1 | 2/2013 | Lim et al. |
| 2013/0065768 | A1 | 3/2013 | Zheng et al. |
| 2013/0079232 | A1 | 3/2013 | Kain et al. |
| 2013/0171621 | A1 | 7/2013 | Luo et al. |
| 2013/0244884 | A1 | 9/2013 | Jacobson et al. |
| 2013/0261019 | A1 | 10/2013 | Lin et al. |
| 2013/0302801 | A1 | 11/2013 | Asbury et al. |
| 2013/0338042 | A1 | 12/2013 | Shen et al. |
| 2014/0066318 | A1 | 3/2014 | Frisen et al. |
| 2014/0121118 | A1 | 5/2014 | Warner |
| 2014/0270435 | A1 | 9/2014 | Dunn |
| 2014/0274731 | A1 | 9/2014 | Raymond et al. |
| 2014/0323330 | A1 | 10/2014 | Glezer et al. |
| 2014/0342921 | A1 | 11/2014 | Weiner |
| 2014/0378350 | A1 | 12/2014 | Hindson et al. |
| 2015/0000854 | A1 | 1/2015 | Gann-Fetter et al. |
| 2015/0292988 | A1 | 10/2015 | Bharadwaj et al. |
| 2015/0344942 | A1 | 12/2015 | Frisen et al. |
| 2016/0019337 | A1 | 1/2016 | Roberts et al. |
| 2016/0024576 | A1 | 1/2016 | Chee |
| 2016/0041159 | A1 | 2/2016 | Labaer et al. |
| 2016/0060687 | A1 | 3/2016 | Zhu et al. |
| 2016/0108458 | A1 | 4/2016 | Frei et al. |
| 2016/0122817 | A1 | 5/2016 | Jarosz et al. |
| 2016/0138091 | A1 | 5/2016 | Chee et al. |
| 2016/0145677 | A1 | 5/2016 | Chee et al. |
| 2016/0194692 | A1 | 7/2016 | Gore et al. |
| 2016/0201125 | A1 | 7/2016 | Samuels et al. |
| 2016/0253584 | A1 | 9/2016 | Fodor et al. |
| 2016/0289740 | A1 | 10/2016 | Fu et al. |
| 2016/0298180 | A1 | 10/2016 | Chee |
| 2016/0305856 | A1 | 10/2016 | Boyden et al. |
| 2016/0312276 | A1 | 10/2016 | Fu et al. |
| 2016/0333403 | A1 | 11/2016 | Chee |
| 2016/0376642 | A1 | 12/2016 | Landegren et al. |
| 2017/0009278 | A1 | 1/2017 | Söderberg et al. |
| 2017/0016053 | A1 | 1/2017 | Beechem et al. |
| 2017/0029875 | A1 | 2/2017 | Zhang et al. |
| 2017/0058339 | A1 | 3/2017 | Chee |
| 2017/0058340 | A1 | 3/2017 | Chee |
| 2017/0058345 | A1 | 3/2017 | Chee |
| 2017/0067096 | A1 | 3/2017 | Wassie et al. |
| 2017/0088881 | A1 | 3/2017 | Chee |
| 2017/0089811 | A1 | 3/2017 | Tillberg et al. |
| 2017/0159109 | A1 | 6/2017 | Zheng et al. |
| 2017/0166962 | A1 | 6/2017 | van Eijk et al. |
| 2017/0220733 | A1 | 8/2017 | Zhuang et al. |
| 2017/0233722 | A1 | 8/2017 | Seelig et al. |
| 2017/0241911 | A1 | 8/2017 | Rockel et al. |
| 2017/0283860 | A1 | 10/2017 | Kool et al. |
| 2017/0335297 | A1 | 11/2017 | Ha et al. |
| 2017/0335410 | A1 | 11/2017 | Driscoll et al. |
| 2017/0342405 | A1 | 11/2017 | Fu et al. |
| 2017/0349940 | A1 | 12/2017 | Morin et al. |
| 2018/0051322 | A1 | 2/2018 | Church et al. |
| 2018/0057873 | A1 | 3/2018 | Zhou et al. |
| 2018/0080019 | A1 | 3/2018 | Blainey et al. |
| 2018/0088112 | A1 | 3/2018 | Fan et al. |
| 2018/0094316 | A1 | 4/2018 | Oliphant et al. |
| 2018/0112261 | A1 | 4/2018 | Van Driel et al. |
| 2018/0127817 | A1 | 5/2018 | Borchert et al. |
| 2018/0163265 | A1 | 6/2018 | Zhang et al. |
| 2018/0179591 | A1 | 6/2018 | van Eijk |
| 2018/0201925 | A1 | 7/2018 | Steemers et al. |
| 2018/0201980 | A1 | 7/2018 | Chee et al. |
| 2018/0208967 | A1 | 7/2018 | Larman et al. |
| 2018/0216161 | A1 | 8/2018 | Chen et al. |
| 2018/0216162 | A1 | 8/2018 | Belhocine et al. |
| 2018/0237864 | A1 | 8/2018 | Imler et al. |
| 2018/0245142 | A1 | 8/2018 | So et al. |
| 2018/0247017 | A1 | 8/2018 | van Eijk et al. |
| 2018/0291427 | A1 | 10/2018 | Edelman |
| 2018/0291439 | A1 | 10/2018 | van Eijk et al. |
| 2018/0305681 | A1 | 10/2018 | Jovanovich et al. |
| 2018/0312822 | A1 | 11/2018 | Lee et al. |
| 2018/0320226 | A1 | 11/2018 | Church et al. |
| 2018/0334670 | A1 | 11/2018 | Bharadwaj et al. |
| 2019/0055594 | A1 | 2/2019 | Samusik et al. |
| 2019/0064173 | A1 | 2/2019 | Bharadwaj et al. |
| 2019/0071656 | A1 | 3/2019 | Chang et al. |
| 2019/0085383 | A1 | 3/2019 | Church et al. |
| 2019/0119735 | A1 | 4/2019 | Deisseroth et al. |
| 2019/0135774 | A1 | 5/2019 | Orbai |
| 2019/0145982 | A1 | 5/2019 | Chee et al. |
| 2019/0161796 | A1 | 5/2019 | Hauling et al. |
| 2019/0177777 | A1 | 6/2019 | Chee |
| 2019/0177778 | A1 | 6/2019 | Chee |
| 2019/0177789 | A1 | 6/2019 | Hindson et al. |

(56) References Cited

U.S. PATENT DOCUMENTS

| | | | |
|---|---|---|---|
| 2019/0177800 | A1 | 6/2019 | Boutet et al. |
| 2019/0194709 | A1 | 6/2019 | Church et al. |
| 2019/0203275 | A1 | 7/2019 | Frisen et al. |
| 2019/0218276 | A1 | 7/2019 | Regev et al. |
| 2019/0218608 | A1 | 7/2019 | Daugharthy et al. |
| 2019/0233878 | A1 | 8/2019 | Delaney et al. |
| 2019/0233880 | A1 | 8/2019 | Mir |
| 2019/0249226 | A1 | 8/2019 | Bent et al. |
| 2019/0262831 | A1 | 8/2019 | West et al. |
| 2019/0264268 | A1 | 8/2019 | Frisen et al. |
| 2019/0271028 | A1 | 9/2019 | Khafizov et al. |
| 2019/0271030 | A1 | 9/2019 | Chee |
| 2019/0271031 | A1 | 9/2019 | Chee |
| 2019/0300943 | A1 | 10/2019 | Chee et al. |
| 2019/0300944 | A1 | 10/2019 | Chee et al. |
| 2019/0300945 | A1 | 10/2019 | Chee et al. |
| 2019/0309353 | A1 | 10/2019 | Chee |
| 2019/0309354 | A1 | 10/2019 | Chee |
| 2019/0309355 | A1 | 10/2019 | Chee |
| 2019/0323071 | A1 | 10/2019 | Chee |
| 2019/0323088 | A1 | 10/2019 | Boutet et al. |
| 2019/0330617 | A1 | 10/2019 | Church et al. |
| 2019/0338353 | A1 | 11/2019 | Belgrader et al. |
| 2019/0360034 | A1 | 11/2019 | Zhou et al. |
| 2019/0360043 | A1 | 11/2019 | Pham et al. |
| 2019/0367969 | A1 | 12/2019 | Belhocine et al. |
| 2019/0367982 | A1 | 12/2019 | Belhocine et al. |
| 2019/0367997 | A1 | 12/2019 | Bent et al. |
| 2020/0002763 | A1 | 1/2020 | Belgrader et al. |
| 2020/0010891 | A1 | 1/2020 | Beechem et al. |
| 2020/0024641 | A1 | 1/2020 | Nolan et al. |
| 2020/0040376 | A1 | 2/2020 | Russel et al. |
| 2020/0047010 | A1 | 2/2020 | Lee et al. |
| 2020/0048690 | A1 | 2/2020 | Chee |
| 2020/0063191 | A1 | 2/2020 | Kennedy-Darling et al. |
| 2020/0063195 | A1 | 2/2020 | Chee |
| 2020/0063196 | A1 | 2/2020 | Chee |
| 2020/0071751 | A1 | 3/2020 | Daugharthy et al. |
| 2020/0080136 | A1 | 3/2020 | Zhang et al. |
| 2020/0109443 | A1 | 4/2020 | Chee |
| 2020/0123597 | A1 | 4/2020 | Daniel |
| 2020/0131570 | A1 | 4/2020 | Berti et al. |
| 2020/0140920 | A1 | 5/2020 | Pierce et al. |
| 2020/0173985 | A1 | 6/2020 | Dong et al. |
| 2020/0199565 | A1 | 6/2020 | Chen et al. |
| 2020/0199572 | A1 | 6/2020 | Kuersten et al. |
| 2020/0224244 | A1 | 7/2020 | Nilsson et al. |
| 2020/0239874 | A1 | 7/2020 | Mikkelsen |
| 2020/0239946 | A1 | 7/2020 | Dewal |
| 2020/0256867 | A1 | 8/2020 | Hennek et al. |
| 2020/0277663 | A1 | 9/2020 | Iyer |
| 2020/0277664 | A1 | 9/2020 | Frenz |
| 2020/0283852 | A1 | 9/2020 | Oliphant et al. |
| 2020/0299757 | A1 | 9/2020 | Chee et al. |
| 2020/0325531 | A1 | 10/2020 | Chee |
| 2020/0362398 | A1 | 11/2020 | Kishi et al. |
| 2020/0370095 | A1 | 11/2020 | Farmer et al. |
| 2020/0399687 | A1 | 12/2020 | Frisen et al. |
| 2020/0407781 | A1 | 12/2020 | Schnall-Levin |
| 2021/0010068 | A1 | 1/2021 | Chee et al. |
| 2021/0010070 | A1 | 1/2021 | Schnall-Levin et al. |
| 2021/0017587 | A1 | 1/2021 | Cai et al. |
| 2021/0095331 | A1 | 4/2021 | Fan et al. |
| 2021/0115504 | A1 | 4/2021 | Cai et al. |
| 2021/0123040 | A1 | 4/2021 | Macosko et al. |
| 2021/0130881 | A1 | 5/2021 | Cox |
| 2021/0140982 | A1 | 5/2021 | Uytingco et al. |
| 2021/0150707 | A1 | 5/2021 | Weisenfeld et al. |
| 2021/0155982 | A1 | 5/2021 | Yin et al. |
| 2021/0158522 | A1 | 5/2021 | Weisenfeld et al. |
| 2021/0172007 | A1 | 6/2021 | Chee et al. |
| 2021/0189475 | A1 | 6/2021 | Tentori et al. |
| 2021/0190770 | A1 | 6/2021 | Delaney et al. |
| 2021/0198741 | A1 | 7/2021 | Williams |
| 2021/0199660 | A1 | 7/2021 | Williams et al. |
| 2021/0207202 | A1 | 7/2021 | Chee |
| 2021/0214785 | A1 | 7/2021 | Stoeckius |
| 2021/0222235 | A1 | 7/2021 | Chee |
| 2021/0222241 | A1 | 7/2021 | Bharadwaj |
| 2021/0222242 | A1 | 7/2021 | Ramachandran Iyer |
| 2021/0222253 | A1 | 7/2021 | Uytingco |
| 2021/0223227 | A1 | 7/2021 | Stoeckius |
| 2021/0230584 | A1 | 7/2021 | Mikkelsen et al. |
| 2021/0230681 | A1 | 7/2021 | Patterson et al. |
| 2021/0230692 | A1 | 7/2021 | Daugharthy et al. |
| 2021/0237022 | A1 | 8/2021 | Bava |
| 2021/0238581 | A1 | 8/2021 | Mikkelsen et al. |
| 2021/0238664 | A1 | 8/2021 | Bava et al. |
| 2021/0238675 | A1 | 8/2021 | Bava |
| 2021/0238680 | A1 | 8/2021 | Bava |
| 2021/0246492 | A1 | 8/2021 | Song et al. |
| 2021/0247316 | A1 | 8/2021 | Bava |
| 2021/0255175 | A1 | 8/2021 | Chee et al. |
| 2021/0262018 | A1 | 8/2021 | Bava et al. |
| 2021/0262019 | A1 | 8/2021 | Alvarado Martinez et al. |
| 2021/0269864 | A1 | 9/2021 | Chee |
| 2021/0270822 | A1 | 9/2021 | Chee |
| 2021/0277460 | A1 | 9/2021 | Bava |
| 2021/0285036 | A1 | 9/2021 | Yin et al. |
| 2021/0285046 | A1 | 9/2021 | Chell et al. |
| 2021/0292748 | A1 | 9/2021 | Frisen et al. |
| 2021/0292822 | A1 | 9/2021 | Frisen et al. |
| 2021/0317510 | A1 | 10/2021 | Chee et al. |
| 2021/0317524 | A1 | 10/2021 | Lucero et al. |
| 2021/0324457 | A1 | 10/2021 | Ramachandran Iyer et al. |
| 2021/0332424 | A1 | 10/2021 | Schnall-Levin |
| 2021/0332425 | A1 | 10/2021 | Pfeiffer et al. |
| 2021/0348221 | A1 | 11/2021 | Chell et al. |
| 2022/0002791 | A1 | 1/2022 | Frisen et al. |
| 2022/0003755 | A1 | 1/2022 | Chee |
| 2022/0010367 | A1 | 1/2022 | Ramachandran Iyer et al. |
| 2022/0017951 | A1 | 1/2022 | Ramachandran Iyer et al. |
| 2022/0025446 | A1 | 1/2022 | Shah |
| 2022/0025447 | A1 | 1/2022 | Tentori et al. |
| 2022/0033888 | A1 | 2/2022 | Schnall-Levin et al. |
| 2022/0049293 | A1 | 2/2022 | Frenz et al. |
| 2022/0064630 | A1 | 3/2022 | Bent et al. |
| 2022/0081728 | A1 | 3/2022 | Williams |
| 2022/0090058 | A1 | 3/2022 | Frisen et al. |
| 2022/0090175 | A1 | 3/2022 | Uytingco et al. |
| 2022/0098576 | A1 | 3/2022 | Dadhwal |
| 2022/0098661 | A1 | 3/2022 | Chew et al. |
| 2022/0106632 | A1 | 4/2022 | Galonska et al. |
| 2022/0106633 | A1 | 4/2022 | Engblom et al. |
| 2022/0112486 | A1 | 4/2022 | Ramachandran Iyer et al. |
| 2022/0112545 | A1 | 4/2022 | Chee |
| 2022/0119869 | A1 | 4/2022 | Ramachandran Iyer et al. |
| 2022/0127659 | A1 | 4/2022 | Frisen et al. |
| 2022/0127666 | A1 | 4/2022 | Katiraee et al. |
| 2022/0127672 | A1 | 4/2022 | Stoeckius |
| 2022/0145361 | A1 | 5/2022 | Frenz et al. |
| 2022/0154255 | A1 | 5/2022 | Chee et al. |
| 2022/0170083 | A1 | 6/2022 | Khaled et al. |
| 2022/0195422 | A1 | 6/2022 | Gallant et al. |
| 2022/0195505 | A1 | 6/2022 | Frisen et al. |
| 2022/0196644 | A1 | 6/2022 | Chee |
| 2022/0213526 | A1 | 7/2022 | Frisen et al. |
| 2022/0220544 | A1 | 7/2022 | Ach et al. |
| 2022/0241780 | A1 | 8/2022 | Tentori et al. |
| 2022/0267844 | A1 | 8/2022 | Ramachandran Iyer et al. |
| 2022/0282329 | A1 | 9/2022 | Chell et al. |
| 2022/0290217 | A1 | 9/2022 | Frenz et al. |
| 2022/0290219 | A1 | 9/2022 | Chee |
| 2022/0298560 | A1 | 9/2022 | Frisen et al. |
| 2022/0325325 | A1 | 10/2022 | Chee et al. |
| 2022/0326251 | A1 | 10/2022 | Uytingco et al. |
| 2022/0333171 | A1 | 10/2022 | Chee |
| 2022/0333191 | A1 | 10/2022 | Mikkelsen et al. |
| 2022/0333192 | A1 | 10/2022 | Uytingco |
| 2022/0333195 | A1 | 10/2022 | Schnall-Levin et al. |
| 2022/0334031 | A1 | 10/2022 | Delaney et al. |
| 2022/0348905 | A1 | 11/2022 | Dadhwal |
| 2022/0348992 | A1 | 11/2022 | Stoeckius et al. |
| 2022/0356464 | A1 | 11/2022 | Kim et al. |

(56) References Cited

U.S. PATENT DOCUMENTS

2022/0364163 A1 11/2022 Stahl et al.
2022/0389491 A1 12/2022 Chee
2022/0389503 A1 12/2022 Mikkelsen et al.
2022/0389504 A1 12/2022 Chew et al.
2022/0403455 A1 12/2022 Ramachandran Iyer et al.
2022/0404245 A1 12/2022 Chell et al.
2023/0002812 A1 1/2023 Stoeckius et al.
2023/0014008 A1 1/2023 Shastry
2023/0017773 A1 1/2023 Kim et al.
2023/0031305 A1 2/2023 Hernandez Neuta et al.
2023/0033960 A1 2/2023 Gallant et al.
2023/0034039 A1 2/2023 Shahjamali
2023/0034216 A1 2/2023 Bava
2023/0040363 A1 2/2023 Chee
2023/0042088 A1 2/2023 Chee
2023/0042817 A1 2/2023 Mignardi
2023/0047782 A1 2/2023 Tentori et al.
2023/0056549 A1 2/2023 Dadhwal
2023/0064372 A1 3/2023 Chell et al.
2023/0069046 A1 3/2023 Chew et al.
2023/0077364 A1 3/2023 Patterson et al.
2023/0080543 A1 3/2023 Katiraee et al.
2023/0081381 A1 3/2023 Chew et al.
2023/0100497 A1 3/2023 Frisen et al.
2023/0107023 A1 4/2023 Chee
2023/0111225 A1 4/2023 Chew et al.
2023/0113230 A1 4/2023 Kim et al.
2023/0126825 A1 4/2023 Nagendran et al.
2023/0129552 A1 4/2023 Ramachandran Iyer
2023/0135010 A1 5/2023 Tentori et al.
2023/0143569 A1 5/2023 Iyer et al.
2023/0145575 A1 5/2023 Gallant et al.
2023/0147726 A1 5/2023 Hadrup et al.
2023/0151412 A1 5/2023 Chee
2023/0159994 A1 5/2023 Chee
2023/0159995 A1 5/2023 Iyer et al.
2023/0160008 A1 5/2023 Chell et al.
2023/0175045 A1 6/2023 Katsori et al.
2023/0183684 A1 6/2023 Gallant et al.
2023/0183785 A1 6/2023 Frisen et al.
2023/0194469 A1 6/2023 Tentori et al.
2023/0194470 A1 6/2023 Kim et al.
2023/0203478 A1 6/2023 Kim et al.
2023/0212650 A1 7/2023 Chew et al.
2023/0212655 A1 7/2023 Chee
2023/0212656 A1 7/2023 Chow et al.
2023/0220368 A1 7/2023 Kim
2023/0220454 A1 7/2023 Bent et al.
2023/0220455 A1 7/2023 Galonska et al.
2023/0227811 A1 7/2023 Dadhwal
2023/0228762 A1 7/2023 Uytingco et al.
2023/0242973 A1 8/2023 Frisen et al.
2023/0242976 A1 8/2023 Tentori et al.
2023/0265488 A1 8/2023 Gohil et al.
2023/0265489 A1 8/2023 Uytingco et al.
2023/0265491 A1 8/2023 Tentori et al.
2023/0267625 A1 8/2023 Tentori et al.
2023/0279474 A1 9/2023 Katiraee
2023/0279477 A1 9/2023 Kvastad et al.
2023/0279481 A1 9/2023 Marrache et al.
2023/0287399 A1 9/2023 Gallant et al.
2023/0287475 A1 9/2023 Chell et al.
2023/0287481 A1 9/2023 Katsori et al.
2023/0295699 A1 9/2023 Sukovich et al.
2023/0295722 A1 9/2023 Bharadwaj
2023/0304072 A1 9/2023 Gohil et al.
2023/0304074 A1 9/2023 Chee et al.
2023/0304078 A1 9/2023 Frisen et al.
2023/0313279 A1 10/2023 Giacomello et al.
2023/0323340 A1 10/2023 Dadhwal
2023/0323434 A1 10/2023 Yin et al.
2023/0323436 A1 10/2023 Chee
2023/0323447 A1 10/2023 Schnall-Levin et al.
2023/0323453 A1 10/2023 Stoeckius
2023/0332138 A1 10/2023 Kim et al.
2023/0332211 A1 10/2023 Chee
2023/0332212 A1 10/2023 Chew et al.
2023/0332227 A1 10/2023 Ramachandran Iyer
2023/0332247 A1 10/2023 Singh et al.
2023/0351619 A1 11/2023 Tentori et al.
2023/0358733 A1 11/2023 Chee
2023/0366008 A1 11/2023 Chew et al.
2023/0383285 A1 11/2023 Kim et al.
2023/0383344 A1 11/2023 Stoeckius
2023/0392204 A1 12/2023 Chell et al.
2023/0393071 A1 12/2023 Bava
2023/0407404 A1 12/2023 Baumgartner et al.
2023/0416807 A1 12/2023 Chee
2023/0416808 A1 12/2023 Sukovich et al.
2023/0416850 A1 12/2023 Singh et al.
2024/0002931 A1 1/2024 Bava
2024/0011081 A1 1/2024 Chee
2024/0011090 A1 1/2024 Chew et al.
2024/0018572 A1 1/2024 Mignardi
2024/0018575 A1 1/2024 Gallant et al.
2024/0018589 A1 1/2024 Schnall-Levin et al.
2024/0026445 A1 1/2024 Ramachandran Iyer et al.
2024/0033743 A1 2/2024 Tentori et al.
2024/0035937 A1 2/2024 Cox et al.
2024/0043908 A1 2/2024 Chew et al.
2024/0043925 A1 2/2024 Bent et al.
2024/0052343 A1 2/2024 Gallant et al.
2024/0053351 A1 2/2024 Uytingco et al.
2024/0060115 A1 2/2024 Chee et al.
2024/0067953 A1 2/2024 Mikkelsen et al.
2024/0068016 A1 2/2024 Frisen et al.
2024/0068017 A1 2/2024 Lundeberg et al.
2024/0076723 A1 3/2024 Mignardi
2024/0080346 A1 3/2024 Engblom et al.
2024/0084365 A1 3/2024 Frisen et al.
2024/0084366 A1 3/2024 Chee
2024/0084383 A1 3/2024 Ramachandran Iyer et al.
2024/0093274 A1 3/2024 Frisen et al.
2024/0093290 A1 3/2024 Stahl et al.
2024/0110228 A1 4/2024 Uytingco et al.
2024/0124933 A1 4/2024 Chell et al.
2024/0125772 A1 4/2024 Delaney et al.
2024/0141327 A1 5/2024 Kim et al.
2024/0158838 A1 5/2024 Alvarado Martinez et al.
2024/0175080 A1 5/2024 Galonska et al.
2024/0182968 A1 6/2024 Bava
2024/0191286 A1 6/2024 Boutet et al.
2024/0200121 A1 6/2024 Boutet
2024/0209425 A1 6/2024 Yin et al.
2024/0218427 A1 7/2024 Sukovich et al.
2024/0218432 A1 7/2024 Mielinis
2024/0219701 A1 7/2024 Tentori et al.
2024/0253036 A1 8/2024 Kim et al.
2024/0263218 A1 8/2024 Katiraee et al.
2024/0271190 A1 8/2024 Stoeckius et al.
2024/0271195 A1 8/2024 Mikhaiel et al.
2024/0279712 A1 8/2024 Fan et al.
2024/0279747 A1 8/2024 Williams
2024/0287600 A1 8/2024 Iyer et al.
2024/0294971 A1 9/2024 Galonska
2024/0294974 A1 9/2024 Galonska et al.
2024/0294975 A1 9/2024 Lin et al.
2024/0301488 A1 9/2024 Stoeckius
2024/0301489 A1 9/2024 Chew et al.
2024/0360494 A1 10/2024 Costa et al.
2024/0368711 A1 11/2024 Giacomello et al.
2024/0377297 A1 11/2024 Cox et al.
2024/0385088 A1 11/2024 Kim et al.
2024/0392349 A1 11/2024 Frisen et al.
2024/0392351 A1 11/2024 Chee
2024/0392352 A1 11/2024 Stahl et al.
2024/0392353 A1 11/2024 Engblom et al.
2024/0401109 A1 12/2024 Kim et al.
2024/0401117 A1 12/2024 Bava
2024/0401118 A1 12/2024 Tentori et al.
2024/0404301 A1 12/2024 Li et al.
2024/0408593 A1 12/2024 Kim et al.
2024/0416315 A1 12/2024 Bava
2024/0417783 A1 12/2024 Chew et al.

(56) References Cited

U.S. PATENT DOCUMENTS

| | | | |
|---|---|---|---|
| 2024/0417784 | A1 | 12/2024 | Sukovich et al. |
| 2025/0002980 | A1 | 1/2025 | Tentori et al. |
| 2025/0002982 | A1 | 1/2025 | Stoeckius et al. |
| 2025/0003956 | A1 | 1/2025 | Delaney et al. |
| 2025/0019749 | A1 | 1/2025 | Katiraee et al. |
| 2025/0066762 | A1 | 2/2025 | Man et al. |
| 2025/0066770 | A1 | 2/2025 | Costa |
| 2025/0073719 | A1 | 3/2025 | Cox et al. |
| 2025/0075261 | A1 | 3/2025 | Kim |
| 2025/0101501 | A1 | 3/2025 | Chee |
| 2025/0101502 | A1 | 3/2025 | Chee |
| 2025/0101504 | A1 | 3/2025 | Nagendran et al. |
| 2025/0122564 | A1 | 4/2025 | Mignardi et al. |
| 2025/0122565 | A1 | 4/2025 | Schnall-Levin et al. |
| 2025/0129412 | A1 | 4/2025 | Uytingco et al. |
| 2025/0129421 | A1 | 4/2025 | Schnall-Levin et al. |
| 2025/0137043 | A1 | 5/2025 | Tentori |
| 2025/0145984 | A1 | 5/2025 | Ma et al. |
| 2025/0146057 | A1 | 5/2025 | Schnall-Levin et al. |
| 2025/0146058 | A1 | 5/2025 | Tentori |
| 2025/0146071 | A1 | 5/2025 | Schnall-Levin et al. |
| 2025/0146072 | A1 | 5/2025 | Schnall-Levin et al. |
| 2025/0154565 | A1 | 5/2025 | Chee |
| 2025/0154566 | A1 | 5/2025 | Chee |
| 2025/0154567 | A1 | 5/2025 | Chee |
| 2025/0154568 | A1 | 5/2025 | Frisen et al. |
| 2025/0154569 | A1 | 5/2025 | Stoeckius et al. |
| 2025/0154571 | A1 | 5/2025 | Ramachandran Iyer et al. |
| 2025/0154588 | A1 | 5/2025 | Ramachandran Iyer et al. |
| 2025/0155446 | A1 | 5/2025 | Uytingco et al. |
| 2025/0163501 | A1 | 5/2025 | Singh et al. |
| 2025/0163509 | A1 | 5/2025 | Daugharthy et al. |
| 2025/0171833 | A1 | 5/2025 | Frisen et al. |
| 2025/0171848 | A1 | 5/2025 | Chell et al. |
| 2025/0179475 | A1 | 6/2025 | Borgstrom et al. |
| 2025/0182305 | A1 | 6/2025 | Tentori et al. |
| 2025/0182503 | A1 | 6/2025 | Li et al. |
| 2025/0188526 | A1 | 6/2025 | Sukovich et al. |
| 2025/0189483 | A1 | 6/2025 | Kim et al. |
| 2025/0197847 | A1 | 6/2025 | Kim et al. |
| 2025/0197938 | A1 | 6/2025 | Bjorninen |
| 2025/0207125 | A1 | 6/2025 | Gupta et al. |
| 2025/0207182 | A1 | 6/2025 | Chee |
| 2025/0207183 | A1 | 6/2025 | Chee |
| 2025/0207195 | A1 | 6/2025 | Chell et al. |
| 2025/0208115 | A1 | 6/2025 | Bent |
| 2025/0215482 | A1 | 7/2025 | Mignardi et al. |
| 2025/0215484 | A1 | 7/2025 | Ramachandran Iyer et al. |
| 2025/0216300 | A1 | 7/2025 | Delaney et al. |
| 2025/0216303 | A1 | 7/2025 | Cox et al. |
| 2025/0223633 | A1 | 7/2025 | Frenz et al. |
| 2025/0230487 | A1 | 7/2025 | Chee et al. |
| 2025/0230498 | A1 | 7/2025 | Katiraee |
| 2025/0250621 | A1 | 8/2025 | Galonska et al. |
| 2025/0250632 | A1 | 8/2025 | Mignardi et al. |
| 2025/0257393 | A1 | 8/2025 | Katiraee et al. |
| 2025/0263791 | A1 | 8/2025 | Bava |
| 2025/0264411 | A1 | 8/2025 | Bava |
| 2025/0283154 | A1 | 9/2025 | Iyer et al. |
| 2025/0283157 | A1 | 9/2025 | Uytingco et al. |
| 2025/0297308 | A1 | 9/2025 | Tentori |
| 2025/0313890 | A1 | 10/2025 | Lundeberg et al. |
| 2025/0313892 | A1 | 10/2025 | Stoeckius |
| 2025/0340932 | A1 | 11/2025 | Chee |
| 2025/0340933 | A1 | 11/2025 | Giacomello et al. |
| 2025/0354931 | A1 | 11/2025 | Shah et al. |
| 2025/0369037 | A1 | 12/2025 | Gupta |
| 2025/0376676 | A1 | 12/2025 | Kim et al. |
| 2025/0376719 | A1 | 12/2025 | Shah |
| 2025/0382665 | A1 | 12/2025 | Frenz et al. |
| 2026/0002202 | A1 | 1/2026 | Schnall-Levin et al. |
| 2026/0009784 | A1 | 1/2026 | Stoeckius |
| 2026/0015653 | A1 | 1/2026 | Chew et al. |
| 2026/0022419 | A1 | 1/2026 | Bent et al. |
| 2026/0035740 | A1 | 2/2026 | Chee |
| 2026/0049349 | A1 | 2/2026 | Gallant et al. |
| 2026/0055443 | A1 | 2/2026 | Tentori et al. |
| 2026/0071262 | A1 | 3/2026 | Yin et al. |
| 2026/0103754 | A1 | 4/2026 | Schnall-Levin et al. |
| 2026/0117286 | A1 | 4/2026 | Katiraee et al. |
| 2026/0117289 | A1 | 4/2026 | Kim |
| 2026/0117298 | A1 | 4/2026 | Doddridge |
| 2026/0117299 | A1 | 4/2026 | Kim et al. |
| 2026/0117302 | A1 | 4/2026 | Chell et al. |
| 2026/0124615 | A1 | 5/2026 | Kim et al. |
| 2026/0132449 | A1 | 5/2026 | Galonska et al. |
| 2026/0132451 | A1 | 5/2026 | Ramachandran Iyer et al. |
| 2026/0146280 | A1 | 5/2026 | Kuhnemund et al. |
| 2026/0176690 | A1 | 6/2026 | Schnall-Levin et al. |
| 2026/0185146 | A1 | 7/2026 | Tentori et al. |
| 2026/0185147 | A1 | 7/2026 | Tentori et al. |
| 2026/0201453 | A1 | 7/2026 | Schnall-Levin et al. |
| 2026/0209833 | A1 | 7/2026 | Katiraee |
| 2026/0242851 | A1 | 8/2026 | Mikhaiel et al. |

FOREIGN PATENT DOCUMENTS

| | | |
|---|---|---|
| CN | 1537953 | 10/2004 |
| CN | 1680604 | 10/2005 |
| CN | 1749752 | 3/2006 |
| CN | 1898398 | 1/2007 |
| CN | 101142325 | 3/2008 |
| CN | 101221182 | 7/2008 |
| CN | 101522915 | 9/2009 |
| CN | 107849606 | 3/2018 |
| CN | 108949924 | 12/2018 |
| EP | 1782737 | 5/2007 |
| EP | 1910562 | 4/2008 |
| EP | 1923471 | 5/2008 |
| EP | 1929039 | 6/2008 |
| EP | 2002017 | 12/2008 |
| EP | 2130913 | 12/2009 |
| EP | 2292788 | 3/2011 |
| EP | 2302070 | 3/2011 |
| EP | 2580351 | 4/2013 |
| EP | 2881465 | 6/2015 |
| EP | 3013984 | 5/2016 |
| EP | 3207134 | 7/2019 |
| EP | 3511423 | 7/2019 |
| EP | 3541956 | 9/2019 |
| GB | 2520765 | 6/2015 |
| JP | 2007-014297 | 1/2007 |
| JP | 2007-074967 | 3/2007 |
| JP | 2009-036694 | 2/2009 |
| WO | WO 1989/010977 | 11/1989 |
| WO | WO 1991/006678 | 5/1991 |
| WO | WO 1993/004199 | 3/1993 |
| WO | WO 1995/023875 | 9/1995 |
| WO | WO 1995/025116 | 9/1995 |
| WO | WO 1995/035505 | 12/1995 |
| WO | WO 1997/031256 | 8/1997 |
| WO | WO 1998/044151 | 10/1998 |
| WO | WO 2000/017390 | 3/2000 |
| WO | WO 2000/063437 | 10/2000 |
| WO | WO 2001/006012 | 1/2001 |
| WO | WO 2001/009363 | 2/2001 |
| WO | WO 2001/012862 | 2/2001 |
| WO | WO 2001/042796 | 6/2001 |
| WO | WO 2001/046402 | 6/2001 |
| WO | WO 2001/059161 | 8/2001 |
| WO | WO 2001/090415 | 11/2001 |
| WO | WO 2001/096608 | 12/2001 |
| WO | WO 2002/040874 | 5/2002 |
| WO | WO 2002/059355 | 8/2002 |
| WO | WO 2002/059364 | 8/2002 |
| WO | WO 2002/077283 | 10/2002 |
| WO | WO 2003/002979 | 1/2003 |
| WO | WO 2003/008538 | 1/2003 |
| WO | WO 2003/010176 | 2/2003 |
| WO | WO 2003/102233 | 12/2003 |
| WO | WO 2004/015080 | 2/2004 |
| WO | WO 2004/067759 | 8/2004 |
| WO | WO 2004/081225 | 9/2004 |
| WO | WO 2005/007814 | 1/2005 |

(56) References Cited

FOREIGN PATENT DOCUMENTS

| | | |
|---|---|---|
| WO | WO 2005/010145 | 2/2005 |
| WO | WO 2005/026387 | 3/2005 |
| WO | WO 2005/042759 | 5/2005 |
| WO | WO 2005/113804 | 12/2005 |
| WO | WO 2006/020515 | 2/2006 |
| WO | WO 2006/124771 | 11/2006 |
| WO | WO 2006/137733 | 12/2006 |
| WO | WO 2007/037678 | 4/2007 |
| WO | WO 2007/041689 | 4/2007 |
| WO | WO 2007/060599 | 5/2007 |
| WO | WO 2007/073171 | 6/2007 |
| WO | WO 2007/076726 | 7/2007 |
| WO | WO 2007/139766 | 12/2007 |
| WO | WO 2007/145612 | 12/2007 |
| WO | WO 2008/069906 | 6/2008 |
| WO | WO 2008/075086 | 6/2008 |
| WO | WO 2008/093098 | 8/2008 |
| WO | WO 2009/032167 | 3/2009 |
| WO | WO 2009/036525 | 3/2009 |
| WO | WO 2009/137521 | 11/2009 |
| WO | WO 2009/152928 | 12/2009 |
| WO | WO 2010/019826 | 2/2010 |
| WO | WO 2010/027870 | 3/2010 |
| WO | WO 2010/088517 | 8/2010 |
| WO | WO 2010/126614 | 11/2010 |
| WO | WO 2010/127186 | 11/2010 |
| WO | WO 2011/008502 | 1/2011 |
| WO | WO 2011/062933 | 5/2011 |
| WO | WO 2011/068088 | 6/2011 |
| WO | WO 2011/127006 | 10/2011 |
| WO | WO 2011/155833 | 12/2011 |
| WO | WO 2012/049316 | 4/2012 |
| WO | WO 2012/061832 | 5/2012 |
| WO | WO 2012/071428 | 5/2012 |
| WO | WO 2012/129242 | 9/2012 |
| WO | WO 2012/159089 | 11/2012 |
| WO | WO 2013/022807 | 2/2013 |
| WO | WO 2013/123442 | 8/2013 |
| WO | WO 2013/131962 | 9/2013 |
| WO | WO 2013/138510 | 9/2013 |
| WO | WO 2013/142389 | 9/2013 |
| WO | WO 2013/150082 | 10/2013 |
| WO | WO 2013/150083 | 10/2013 |
| WO | WO 2013/192292 | 12/2013 |
| WO | WO 2014/044724 | 3/2014 |
| WO | WO 2014/060483 | 4/2014 |
| WO | WO 2014/066179 | 5/2014 |
| WO | WO 2014/071361 | 5/2014 |
| WO | WO 2014/130576 | 8/2014 |
| WO | WO 2014/144713 | 9/2014 |
| WO | WO 2014/152397 | 9/2014 |
| WO | WO 2014/210223 | 12/2014 |
| WO | WO 2014/210353 | 12/2014 |
| WO | WO 2015/031691 | 3/2015 |
| WO | WO 2015/057319 | 4/2015 |
| WO | WO 2015/069374 | 5/2015 |
| WO | WO 2015/094861 | 6/2015 |
| WO | WO 2015/122967 | 8/2015 |
| WO | WO 2015/161173 | 10/2015 |
| WO | WO 2016/077763 | 5/2016 |
| WO | WO 2016/100196 | 6/2016 |
| WO | WO 2016/138496 | 9/2016 |
| WO | WO 2016/138500 | 9/2016 |
| WO | WO 2016/162309 | 10/2016 |
| WO | WO 2016/166128 | 10/2016 |
| WO | WO 2016/168825 | 10/2016 |
| WO | WO 2016/172362 | 10/2016 |
| WO | WO 2017/019456 | 2/2017 |
| WO | WO 2017/019481 | 2/2017 |
| WO | WO 2017/044993 | 3/2017 |
| WO | WO 2017/075293 | 5/2017 |
| WO | WO 2017/096158 | 7/2017 |
| WO | WO 2017/143155 | 8/2017 |
| WO | WO 2017/156336 | 9/2017 |
| WO | WO 2017/184984 | 10/2017 |
| WO | WO 2017/192633 | 11/2017 |
| WO | WO 2018/023068 | 2/2018 |
| WO | WO 2018/026873 | 2/2018 |
| WO | WO 2018/045181 | 3/2018 |
| WO | WO 2018/064640 | 4/2018 |
| WO | WO 2018/085599 | 5/2018 |
| WO | WO 2018/089550 | 5/2018 |
| WO | WO 2018/091676 | 5/2018 |
| WO | WO 2018/136397 | 7/2018 |
| WO | WO 2018/136856 | 7/2018 |
| WO | WO 2018/144582 | 8/2018 |
| WO | WO 2018/175779 | 9/2018 |
| WO | WO 2018/209398 | 11/2018 |
| WO | WO 2018/217862 | 11/2018 |
| WO | WO 2019/023214 | 1/2019 |
| WO | WO 2019/032760 | 2/2019 |
| WO | WO 2019/068880 | 4/2019 |
| WO | WO 2019/089836 | 5/2019 |
| WO | WO 2019/089851 | 5/2019 |
| WO | WO 2019/113457 | 6/2019 |
| WO | WO 2019/126313 | 6/2019 |
| WO | WO 2019/140201 | 7/2019 |
| WO | WO 2019/165318 | 8/2019 |
| WO | WO 2019/213254 | 11/2019 |
| WO | WO 2019/213294 | 11/2019 |
| WO | WO 2019/222523 | 11/2019 |
| WO | WO 2019/241290 | 12/2019 |
| WO | WO 2020/028194 | 2/2020 |
| WO | WO 2020/041148 | 2/2020 |
| WO | WO 2020/047002 | 3/2020 |
| WO | WO 2020/047010 | 3/2020 |
| WO | WO 2020/053655 | 3/2020 |
| WO | WO 2020/056381 | 3/2020 |
| WO | WO 2020/061064 | 3/2020 |
| WO | WO 2020/061066 | 3/2020 |
| WO | WO 2020/061108 | 3/2020 |
| WO | WO 2020/076979 | 4/2020 |
| WO | WO 2020/099640 | 5/2020 |
| WO | WO 2020/112604 | 6/2020 |
| WO | WO 2020/117914 | 6/2020 |
| WO | WO 2020/123301 | 6/2020 |
| WO | WO 2020/123305 | 6/2020 |
| WO | WO 2020/123309 | 6/2020 |
| WO | WO 2020/123311 | 6/2020 |
| WO | WO 2020/123316 | 6/2020 |
| WO | WO 2020/123317 | 6/2020 |
| WO | WO 2020/123318 | 6/2020 |
| WO | WO 2020/123319 | 6/2020 |
| WO | WO 2020/123320 | 7/2020 |
| WO | WO 2020/160044 | 8/2020 |
| WO | WO 2020/167862 | 8/2020 |
| WO | WO 2020/176788 | 9/2020 |
| WO | WO 2020/176882 | 9/2020 |
| WO | WO 2020/190509 | 9/2020 |
| WO | WO 2020/198071 | 10/2020 |
| WO | WO 2020/206285 | 10/2020 |
| WO | WO 2020/240025 | 12/2020 |
| WO | WO 2020/243579 | 12/2020 |
| WO | WO 2020/254519 | 12/2020 |
| WO | WO 2021/041974 | 3/2021 |
| WO | WO 2021/067246 | 4/2021 |
| WO | WO 2021/067514 | 4/2021 |
| WO | WO 2021/091611 | 5/2021 |
| WO | WO 2021/092433 | 5/2021 |
| WO | WO 2021/097255 | 5/2021 |
| WO | WO 2021/102003 | 5/2021 |
| WO | WO 2021/102005 | 5/2021 |
| WO | WO 2021/102039 | 5/2021 |
| WO | WO 2021/116715 | 6/2021 |
| WO | WO 2021/119320 | 6/2021 |
| WO | WO 2021/133842 | 7/2021 |
| WO | WO 2021/133845 | 7/2021 |
| WO | WO 2021/133849 | 7/2021 |
| WO | WO 2021/142233 | 7/2021 |
| WO | WO 2021/168261 | 8/2021 |
| WO | WO 2021/168278 | 8/2021 |
| WO | WO 2021/207610 | 10/2021 |
| WO | WO 2021/216708 | 10/2021 |
| WO | WO 2021/225900 | 11/2021 |

(56) References Cited

FOREIGN PATENT DOCUMENTS

| | | |
|---|---|---|
| WO | WO 2021/236625 | 11/2021 |
| WO | WO 2021/236929 | 11/2021 |
| WO | WO 2021/237056 | 11/2021 |
| WO | WO 2021/237087 | 11/2021 |
| WO | WO 2021/242834 | 12/2021 |
| WO | WO 2021/247543 | 12/2021 |
| WO | WO 2021/247568 | 12/2021 |
| WO | WO 2021/247593 | 12/2021 |
| WO | WO 2021/252499 | 12/2021 |
| WO | WO 2021/252576 | 12/2021 |
| WO | WO 2021/252591 | 12/2021 |
| WO | WO 2021/252747 | 12/2021 |
| WO | WO 2021/263111 | 12/2021 |
| WO | WO 2022/025965 | 2/2022 |
| WO | WO 2022/032195 | 2/2022 |
| WO | WO 2022/060798 | 3/2022 |
| WO | WO 2022/060953 | 3/2022 |
| WO | WO 2022/061150 | 3/2022 |
| WO | WO 2022/061152 | 3/2022 |
| WO | WO 2022/087273 | 4/2022 |
| WO | WO 2022/099037 | 5/2022 |
| WO | WO 2022/103712 | 5/2022 |
| WO | WO 2022/109181 | 5/2022 |
| WO | WO 2011/019964 | 6/2022 |
| WO | WO 2022/132645 | 6/2022 |
| WO | WO 2022/140028 | 6/2022 |
| WO | WO 2022/147005 | 7/2022 |
| WO | WO 2022/147296 | 7/2022 |
| WO | WO 2022/164615 | 8/2022 |
| WO | WO 2022/178267 | 8/2022 |
| WO | WO 2022/198068 | 9/2022 |
| WO | WO 2022/212269 | 10/2022 |
| WO | WO 2022/221425 | 10/2022 |
| WO | WO 2022/226057 | 10/2022 |
| WO | WO 2022/236054 | 11/2022 |
| WO | WO 2022/243303 | 11/2022 |
| WO | WO 2022/226372 | 12/2022 |
| WO | WO 2022/256503 | 12/2022 |
| WO | WO 2022/271820 | 12/2022 |
| WO | WO 2023/287765 | 1/2023 |
| WO | WO 2023/018799 | 2/2023 |
| WO | WO 2023/034489 | 3/2023 |
| WO | WO 2023/034739 | 3/2023 |
| WO | WO 2023/044071 | 3/2023 |
| WO | WO 2023/076345 | 5/2023 |
| WO | WO 2023/086880 | 5/2023 |
| WO | WO 2023/102118 | 6/2023 |
| WO | WO 2023/122033 | 6/2023 |
| WO | WO 2023/130019 | 7/2023 |
| WO | WO 2023/147355 | 8/2023 |
| WO | WO 2023/150098 | 8/2023 |
| WO | WO 2023/150163 | 8/2023 |
| WO | WO 2023/150171 | 8/2023 |
| WO | WO 2023/150763 | 8/2023 |
| WO | WO 2023/215552 | 11/2023 |
| WO | WO 2023/225519 | 11/2023 |
| WO | WO 2023/229988 | 11/2023 |
| WO | WO 2023/250077 | 12/2023 |
| WO | WO 2024/015578 | 1/2024 |
| WO | WO 2024/035844 | 2/2024 |
| WO | WO 2024/081212 | 4/2024 |
| WO | WO 2024/086167 | 4/2024 |
| WO | WO 2024/086776 | 4/2024 |
| WO | WO 2024/102809 | 5/2024 |
| WO | WO 2024/137826 | 6/2024 |
| WO | WO 2024/145224 | 7/2024 |
| WO | WO 2024/145441 | 7/2024 |
| WO | WO 2024/145445 | 7/2024 |
| WO | WO 2024/145491 | 7/2024 |
| WO | WO 2024/206603 | 10/2024 |
| WO | WO 2024/220882 | 10/2024 |
| WO | WO 2024/238900 | 11/2024 |
| WO | WO 2024/254316 | 12/2024 |
| WO | WO 2025/029605 | 2/2025 |
| WO | WO 2025/029627 | 2/2025 |
| WO | WO 2025/043076 | 2/2025 |
| WO | WO 2025/072119 | 4/2025 |
| WO | WO 2025/090912 | 5/2025 |
| WO | WO 2025/096581 | 5/2025 |
| WO | WO 2025/101864 | 5/2025 |

OTHER PUBLICATIONS

Deng et al., "Spatial-ATAC-seq: spatially resolved chromatin accessibility profiling of tissues at genome scale and cellular level," bioRxiv, Jun. 7, 2021, retrieved from URL <https://www.biorxiv.org/content/10.1101/2021.06.06.447244v1>, 49 pages (Preprint).

Hong et al., "Cell Microarray Technologies for High-Throughput Cell-Based Biosensors," Sensors (Basel), Jun. 5, 2017, 17(6):1293.

Stickels et al., "Highly sensitive spatial transcriptomics at near-cellular resolution with Slide-seqV2," Nat Biotechnol., Mar. 2021, 39(3):313-319, 28 pages (Author Manuscript).

Kishi et al., "Light-Seq: light-directed in situ barcoding of biomolecules in fixed cells and tissues for spatially indexed sequencing," Nature Methods, Oct. 10, 2022, 19(11):1393-1402.

10xGenomics.com, [online], "Visium Spatial Gene Expression Reagent Kits—Tissue Optimization—User Guide," Feb. 2022, retrieved on Mar. 29, 2024, retrieved from URL<https://cdn.10xgenomics.com/image/upload/v1660261286/support-documents/CG000238_VisiumSpatialTissueOptimizationUserGuide_RevE.pdf>, 46 pages.

Asp et al., "A spatiotemporal organ-wide gene expression and cell atlas of the developing human heart," Cell, Dec. 12, 2019, 179(7):1647-1660.

Kuhn et al., "A novel, high-performance random array platform for quantitative gene expression profiling," Genome Res, 2004, 14:2347-2356.

PCT International Preliminary Report on Patentability in International Appln. No. PCT/US2022/039956, dated Feb. 22, 2024, 9 pages.

10xGenomics.com, [online], "Visium Spatial Gene Expression Reagent Kits—User Guide," Jan. 2022, retrieved on Jun. 27, 2024, retrieved from URL<https://web.archive.org/web/20230326192142/https://www.10xgenomics.com/support/spatial-gene-expression-fresh-frozen/documentation/steps/library-construction/visium-spatial-gene-expression-reagent-kits-user-guide>, 71 pages.

[No Author Listed], "Chromium Next GEM Single Cell 3' Reagent Kits v3.1—User Guide," 10x Genomics, Document No. CG000204, Nov. 2019, 58 pages.

[No Author Listed], "Chromium Next GEM Single Cell 3' Reagent Kits v3.1 (Dual Index)—User Guide," 10x Genomics, Mar. 2021, Document No. CG000315, 61 pages.

[No Author Listed], "HuSNP Mapping Assay User's Manual," Affymetrix Part No. 90094 (Affymetrix, Santa Clara, Calif), GeneChip, 2000, 104 pages.

[No Author Listed], "Microarray technologies have excellent possibilities in genomics-related researches," Science Tools From Amersham Pharmacia Biotech, 1998, 3(4): 8 pages (with English Translation).

[No Author Listed], "ProseekR Multiplex 96×96 User Manual," Olink Proteomics, Olink Bioscience, Uppsala, Sweden, 2017, 20 pages.

10xGenomics.com, [online], "Visium Spatial Gene Expression Reagent Kits—Tissue Optimization—User Guide," Jul. 2020, retrieved on May 25, 2021, retrieved from URL<https://assets.ctfassets.net/an68im79xiti/5UJrN0cH17rEk0UXwd19It/e54d99fb08a8f1500aba503005a04a56/CG000238_VisiumSpatialTissueOptimizationUserGuide_RevD.pdf>, 42 pages.

10xGenomics.com, [online], "Visium Spatial Gene Expression Reagent Kits—Tissue Optimization," Nov. 2019, retrieved on Jan. 25, 2022, retrieved from URL<https://assets.ctfassets.net/an68im79xiti/4q03w6959AJFxffSw5lee9/6a2ac61cf6388a72564eeb96bc294967/CG000238_VisiumSpatialTissueOptimizationUserGuide_Rev_A.pdf>, 46 pages.

10xGenomics.com, [online], "Visium Spatial Gene Expression Reagent Kits—Tissue Optimization," Oct. 2020, retrieved on Dec. 28, 2021, retrieved from URL<https://assets.ctfassets.net/an68im79xiti/

(56) References Cited

OTHER PUBLICATIONS

5UJrN0cH17rEk0UXwd19It/e54d99fb08a8f1500aba503005a04a56/CG000238_VisiumSpatialTissueOptimizationUserGuide_RevD.pdf>, 43 pages.
10xGenomics.com, [online], "Visium Spatial Gene Expression Reagent Kits—User Guide," Jun. 2020, retrieved on May 25, 2021, retrieved from URL<https://assets.ctfassets.net/an68im79xiti/3GGIfH3RWpd1bFVhalpexR/8baa08d9007157592b65b2cdc7130990/CG000239_VisiumSpatialGeneExpression_UserGuide_RevD.pdf>, 69 pages.
10xGenomics.com, [online], "Visium Spatial Gene Expression Reagent Kits—User Guide," Oct. 2020, retrieved on Dec. 28, 2021, retrieved from URL<https://assets.ctfassets.net/an68im79xiti/3GGIfH3RWpd1bFVhalpexR/8baa08d9007157592b65b2cdc7130990/CG000239_VisiumSpatialGeneExpression_UserGuide_RevD.pdf>, 70 pages.
Adessi et al., "Solid phase DNA amplification: characterisation of primer attachment and amplification mechanisms," Nucl. Acids Res., 2000, 28(20):E87, 8 pages.
Adiconis et al., "Comparative analysis of RNA sequencing methods for degraded or low-input samples," Nat Methods, Jul. 2013, 10(7):623-9.
Affymetrix, "GeneChip Human Genome U133 Set," retrieved from the Internet: on the World Wide Web at affymetrix.com/support/technical/datasheets/hgu133_datasheet.pdf, retrieved on Feb. 26, 2003, 2 pages.
Affymetrix, "Human Genome U95Av2," Internet Citation, retrieved from the internet: on the World Wide Web affymetrix.com, retrieved on Oct. 2, 2002, 1 page.
Alam, "Proximity Ligation Assay (PLA)," Curr Protoc Immunol., Nov. 2018, 123(1):e58, 8 pages.
Albretsen et al., "Applications of magnetic beads with covalently attached oligonucleotides in hybridization: Isolation and detection of specific measles virus mRNA from a crude cell lysate," Anal. Biochem., 1990, 189(1):40-50.
Allawi et al., "Thermodynamics and NMR of Internal G.T Mismatches in DNA," Biochemistry, 1996, 36(34):10581-10594.
Amidzadeh et al., "Assessment of different permeabilization methods of minimizing damage to the adherent cells for detection of intracellular RNA by flow cytometry," Avicenna J Med Biotechnol., Jan. 2014, 6(1):38-46.
Andresen et al., "Helicase-dependent amplification: use in OnChip amplification and potential for point-of-care diagnostics," Expert Rev Mol Diagn., Oct. 2009, 9(7):645-650.
Appella, "Non-natural nucleic acids for synthetic biology," Current Opinion in Chemical Biology, Dec. 2009, 13(5-6): 687-696.
Aran et al., "xCell: digitally portraying the tissue cellular heterogeneity landscape," Genome Biol., Nov. 2017, 18(1):220, 14 pages.
Archer et al., "Selective and flexible depletion of problematic sequences from RNA-seq libraries at the cDNA stage," BMC Genomics, May 2014, 15(1):401, 9 pages.
Armani et al., "2D-PCR: a method of mapping DNA in tissue sections," Lab Chip, 2009, 9(24):3526-34.
Arslan et al., "Engineering of a superhelicase through conformational control (Supplementary Materials)," Science, Apr. 17, 2015, 348(6232):344-347, 18 pages.
Arslan et al., "Engineering of a superhelicase through conformational control," Science, Apr. 17, 2015, 348(6232):344-347.
Asp et al., "Spatially Resolved Transcriptomes—Next Generation Tools for Tissue Exploration," Bioessays, Oct. 2020, 42(10):e1900221, 16 pages.
Atkinson et al., "An Updated Protocol for High Throughput Plant Tissue Sectioning," Front Plant Sci, 2017, 8:1721, 8 pages.
Atkinson, "Overview of Translation: Lecture Manuscript," U of Texas, 2000, DD, pp. 6.1-6.8.
Bains et al., "A novel method for nucleic acid sequence determination," Journal of Theoretical Biology, 1988, 135(3), 303-7.
Balakrishnan et al., "Flap endonuclease 1," Annu Rev Biochem., Jun. 2013, 82:119-138.
Baner et al., "Signal amplification of padlock probes by rolling circle replication," Nucleic Acids Res., 1998, 26(22):5073-5078.
Barnes, "PCR amplification of up to 35-kb DNA with high fidelity and high yield from lambda bacteriophage templates," Proc. Natl. Acad. Sci USA, 1994, 91(6):2216-2220.
Barnett et al., "ATAC-Me Captures Prolonged DNA Methylation of Dynamic Chromatin Accessibility Loci during Cell Fate Transitions," Mol Cell., Mar. 2020, 77(6):1350-1364.e6.
Bartosovic et al., "Single-cell CUT&Tag profiles histone modifications and transcription factors in complex tissues," Nat Biotechnol., Jul. 2021, 39(7):825-835, Abstract.
Baugh et al., "Quantitative analysis of mRNA amplification by in vitro transcription," Nucleic Acids Res., 2001, 29(5):e29, 9 pages.
Beattie et al., "Advances in genosensor research," Clin Chem., May 1995, 41(5):700-6.
Beechem et al., "High-Plex Spatially Resolved RNA and Protein Detection Using Digital Spatial Profiling: A Technology Designed for Immuno-oncology Biomarker Discovery and Translational Research," Methods Mol Biol, 2020, Chapter 25, 2055:563-583.
Belaghzal et al., "Hi-C 2.0: An Optimized Hi-C Procedure for High-Resolution Genome-Wide Mapping of Chromosome Conformation," Methods, Jul. 1, 2017, 123:56-65, 20 pages.
Bell, "A simple way to treat PCR products prior to sequencing using ExoSAP-IT," Biotechniques, 2008, 44(6):834, 1 page.
Belton et al., "Hi-C: A comprehensive technique to capture the conformation of genomes," Methods, Nov. 2012, 58(3):268-276, 16 pages.
Bentley et al., "Accurate whole human genome sequencing using reversible terminator chemistry," Nature, 2008, 456(7218):53-59.
Bentzen et al., "Large-scale detection of antigen-specific T cells using peptide-MHC-I multimers labeled with DNA barcodes," Nat Biotechnol., Oct. 2016, 34(10):1037-1045, 12 pages.
Bergenstråhle et al., "Seamless integration of image and molecular analysis for spatial transcriptomics workflows," BMC Genomics, Jul. 2020, 21(1):482, 7 pages.
Berger et al., "Universal bases for hybridization, replication and chain termination," Nucleic Acid Res., Aug. 2000, 28(15):2911-2914.
Bibikova et al., "Quantitative gene expression profiling in formalin-fixed paraffin-embedded tissues using universal bead arrays," The American Journal of Pathology, Nov. 1, 2004, 165(5):1799-1807.
Birney et al., "Identification and analysis of functional elements in 1% of the human genome by the ENCODE pilot project," Nature, 2007, 447(7146):799-816.
Blair et al., "Microarray temperature optimization using hybridization kinetics," Methods Mol Biol., 2009, 529:171-96.
Blanchard et al., "High-density oligonucleotide arrays," Biosensors & Bioelectronics, 1996, 11(6-7):687-690.
Blanco et al., "A practical approach to FRET-based PNA fluorescence in situ hybridization," Methods, Dec. 2010, 52(4):343-51.
Blokzijl et al., "Profiling protein expression and interactions: proximity ligation as a tool for personalized medicine," J Intern. Med., 2010, 268(3):232-245.
Blow, "Tissue Issues," Nature, 2007, 448(7156):959-962.
Bolotin et al., "MiXCR: software for comprehensive adaptive immunity profiling," Nat Methods., May 2015, 12(5):380-1.
Borm et al., "High throughput human embryo spatial transcriptome mapping by surface transfer of tissue RNA," Abstracts Selected Talks, Single Cell Genomics mtg, (SCG2019), 2019, 1 pages (Abstract Only).
Boulé et al., "Terminal deoxynucleotidyl transferase indiscriminately incorporates ribonucleotides and deoxyribonucleotides," J Biol Chem., Aug. 2001, 276(33):31388-93.
Brandon et al., "Mitochondrial mutations in cancer," Oncogene, 2006, 25(34):4647-4662.
Brenner et al., "Gene expression analysis by massively parallel signature sequencing (MPSS) on microbead arrays," Nat. Biotech., 2000, 18(6):630-634.
Brenner et al., "In vitro cloning of complex mixtures of DNA on microbeads: physical separation of differentially expressed cDNAs," Proc. Natl. Acad. Sci. USA, 2000, 97(4):1665-1670.

(56) References Cited

OTHER PUBLICATIONS

Brow, "35—The Cleavase I enzyme for mutation and polymorphism scanning," PCR Applications Protocols for Functional Genomics, 1999, pp. 537-550.
Brown et al., "Retroviral integration: structure of the initial covalent product and its precursor, and a role for the viral IN protein," Proc Natl Acad Sci USA, Apr. 1989, 86(8):2525-9.
Buenrostro et al., "Transposition of native chromatin for multimodal regulatory analysis and personal epigenomics," Nat Methods, Dec. 2013, 10(12):1213-1218.
Bullard et al., "Direct comparison of nick-joining activity of the nucleic acid ligases from bacteriophage T4," Biochem. J. 2006, 398(1):135-144.
Bunt et al., "FRET from single to multiplexed signaling events," Biophys Rev. Apr. 2017, 9(2): 119-129.
Burgess, "A space for transcriptomics," Nature Reviews Genetics, 2016, 17(8):436-7.
Burgess, "Finding structure in gene expression," Nature Reviews Genetics, 2018, 19(5):249, 1 page.
Burgess, "Spatial transcriptomics coming of age," Nat Rev Genet., Jun. 2019, 20(6):317, 1 page.
Caliari et al., "A practical guide to hydrogels for cell culture," Nat Methods., Apr. 2016, 13(5):405-14.
Cha et al., "Specificity, efficiency, and fidelity of PCR," Genome Res., 1993, 3(3):S18-29.
Chandra et al., "Cell-free synthesis-based protein microarrays and their applications," Proteomics, 2009, 5(6):717-30.
Chatterjee et al., "Mitochondrial DNA mutations in human cancer. Oncogene," 2006, 25(34):4663-4674.
Chen et al. "Arrayed profiling of multiple glycans on whole living cell surfaces." Analytical chemistry, Oct. 15, 2013, 85(22):11153-11158.
Chen et al., "DNA hybridization detection in a microfluidic Channel using two fluorescently labelled nucleic acid probes," Biosensors and Bioelectronics, 2008, 23(12):1878-1882.
Chen et al., "Efficient in situ barcode sequencing using padlock probe-based BaristaSeq," Nucleic Acids Res., 2018, 46(4): e22, 11 pages.
Chen et al., "Expansion microscopy," Science, 2015, 347(6221):543-548.
Chen et al., "Large field of view-spatially resolved transcriptomics at nanoscale resolution," bioRxiv, Jan. 19, 2021, retrieved from URL <https://www.biorxiv.org/node/1751045.abstract>, 37 pages.
Chen et al., "Nanoscale imaging of RNA with expansion microscopy," Nat Methods, Aug. 2016, 13(8):679-84.
Chen et al., "Parallel single nucleotide polymorphism genotyping by surface invasive cleavage with universal detection," Anal Chem., Apr. 2005, 77(8):2400-5.
Chen et al., "RNA imaging. Spatially resolved, highly multiplexed RNA profiling in single cells," Science, Apr. 2015, 348(6233):aaa6090, 21 pages.
Chen et al., "Spatial Transcriptomics and In Situ Sequencing to Study Alzheimer's Disease," Cell, Aug. 2020, 182(4):976-991.
Chen et al., "µCB-seq: microfluidic cell barcoding and sequencing for high-resolution imaging and sequencing of single cells," Lab Chip, Nov. 2020, 20(21):3899-3913.
Chester et al., "Dimethyl sulfoxide-mediated primer Tm reduction: a method for analyzing the role of renaturation temperature in the polymerase chain reaction," Anal Biochem, Mar. 1993, 209(2):284-90.
Cho et al., "Seq-Scope: Submicrometer-resolution spatial transcriptomics for single cell and subcellular studies," bioRxiv, Jan. 27, 2021, retrieved from URL <https://www.biorxiv.org/node/1754517.abstract>, 50 pages.
Choi et al., "Multiplexed detection of mRNA using porosity-tuned hydrogel microparticles," Analytical chemistry, Sep. 28, 2012, 84(21):9370-9378.
Chrisey et al., "Covalent attachment of synthetic DNA to self-assembled monolayer films," Nucleic Acids Res., Aug. 1996, 24(15):3031-9.
Ciaccio et al., "Systems analysis of EGF receptor signaling dynamics with microwestern arrays," Nat Methods, Feb. 2010, 7(2):148-55.
Codeluppi et al., "Spatial organization of the somatosensory cortex revealed by osmFISH," Nature Methods, Nov. 2018, 15:932-935.
Constantine et al., "Use of genechip high-density oligonucleotide arrays for gene expression monitoring," Life Science News, Amersham Life Science, 1998, pp. 11-14.
Corces et al., "An improved ATAC-seq protocol reduces background and enables interrogation of frozen tissues," Nat. Methods, 2017, 14(10):959-962.
Credle et al., "Multiplexed analysis of fixed tissue RNA using Ligation in situ Hybridization," Nucleic Acids Research, 2017, 45(14):e128, 9 pages.
Crosetto et al., "Spatially resolved transcriptomics and beyond," Nature Review Genetics, 2015, 16(1):57-66.
Cruz et al., "Methylation in cell-free DNA for early cancer detection," Ann Oncol., Jun. 2018, 29(6):1351-1353.
Cujec et al., "Selection of v-Abl tyrosine kinase substrate sequences from randomized peptide and cellular proteomic libraries using mRNA display," Chemistry and Biology, 2002, 9(2):253-264.
Czarnik, "Encoding methods for combinatorial chemistry," Curr Opin Chem Biol., Jun. 1997, 1(1):60-6.
Dahl et al., "Circle-to-circle amplification for precise and sensitive DNA analysis," Proc. Natl. Acad. Sci., 2004, 101(13):4548-4553.
Dalma-Weiszhausz et al., "The affymetrix GeneChip platform: an overview," Methods Enzymol., 2006, 410:3-28.
Darmanis et al., "ProteinSeq: High-Performance Proteomic Analyses by Proximity, Ligation and Next Generation Sequencing," PLos One, 2011, 6(9):e25583, 10 pages.
Daubendiek et al., "Rolling-Circle RNA Synthesis: Circular Oligonucleotides as Efficient Substrates for T7 RNA Polymerase," J. Am. Chem. Soc, 1995, 117(29):7818-7819.
Davies et al., "How best to identify chromosomal interactions: a comparison of approaches," Nat. Methods, 2017, 14(2):125-134.
Deamer et al., "Characterization of nucleic acids by Nanopore analysis," Acc Chem Res., Oct. 2002, 35(10):817-25.
Dean et al., "Comprehensive human genome amplification using multiple displacement amplification," Proc Natl. Acad. Sci. USA, 2002, 99(8):5261-66.
Dean et al., "Rapid Amplification Of Plasmid And Phage DNA Using Phi29 DNA Polymerase And Multiply-Primed Rolling Circle Amplification," Genome Research, Jun. 2001, 11:1095-1099.
Deng et al., "Spatial Epigenome Sequencing at Tissue Scale and Cellular Level," BioRxiv, Mar. 2021, 40 pages.
Doshi et al., "In vitro nanobody discovery for integral membrane protein targets," Scientific Reports, Oct. 4, 2014, 4:6760, 8 pages.
Dressman et al., "Transforming single DNA molecules into fluorescent magnetic particles for detection and enumeration of genetic variations," Proc. Natl. Acad. Sci. USA, 2003, 100(15):8817-8822.
Drmanac et al., "CoolMPS™: Advanced massively parallel sequencing using antibodies specific to each natural nucleobase," BioRxiv, 2020, 19 pages.
Druley et al., "Quantification of rare allelic variants from pooled genomic DNA," Nat. Methods, 2009, 6(4):263-65.
Duncan et al., "Affinity chromatography of a sequence-specific DNA binding protein using Teflon-linked oligonucleotides," Anal. Biochem., 1988, 169(1):104-108.
Eberwine, "Amplification of mRNA populations using aRNA generated from immobilized oligo(dT)-T7 primed cDNA," BioTechniques, 1996, 20(4):584-91.
Eguiluz et al., "Multitissue array review: a chronological description of tissue array techniques, applications and procedures," Pathology Research and Practice, 2006, 202(8):561-568.
Eldridge et al., "An in vitro selection strategy for conferring protease resistance to ligand binding peptides," Protein Eng Des Sel., 2009, 22(11):691-698.
Ellington et al., "Antibody-based protein multiplex platforms: technical and operational challenges," Clin Chem, 2010, 56(2):186-193.
Eng et al., "Profiling the transcriptome with RNA SPOTs," Nat Methods., 2017, 14(12):1153-1155.

(56) References Cited

OTHER PUBLICATIONS

Eng et al., "Transcriptome-scale super-resolved imaging in tissues by RNA seqFISH+," Nature, Apr. 2019, 568(7751):235-239, 37 pages.
Ergin et al., "Proteomic Analysis of PAXgene-Fixed Tissues," J Proteome Res., 2010, 9(10):5188-96.
Ertsey et al., "Coverslip Mounted-Immersion Cycled in Situ RT-PCR for the Localization of mRNA in Tissue Sections," Biotechniques, 1998, 24(1):92-100.
Evers et al., "The effect of formaldehyde fixation on RNA: optimization of formaldehyde adduct removal," J Mol Diagn., May 2011, 13(3):282-8.
Fan et al., "A versatile assay for high-throughput gene expression profiling on universal array matrices," Genome Research, May 1, 2004, 14(5):878-885.
Fan et al., "Illumina Universal Bead Arrays," Methods in Enzymology, 2006, 410:57-73.
Faruqi et al., "High-throughput genotyping of single nucleotide polymorphisms with rolling circle amplification," BMC Genomics, Aug. 2001, 2:4, 10 pages.
Fire et al., "Rolling replication of short DNA circles," Proc. Natl. Acad. Sci., 1995, 92(10):4641-4645.
Fiskin et al., "Single-cell multimodal profiling of proteins and chromatin accessibility using PHAGE-ATAC," bioRxiv, posted Oct. 20, 2020, 63 pages.
Flanigon et al., "Multiplex protein detection with DNA readout via mass spectrometry," N. Biotechnol., 2013, 30(2):153-158.
Fluidigm, "Equivalence of Imaging Mass Cytometry and Immunofluorescence on FFPE Tissue Sections," White Paper, 2017, 12 pages.
Fodor et al., "Light-directed, spatially addressable parallel chemical synthesis," Science, 1995, 251(4995):767-773.
Forster et al., "A human gut bacterial genome and culture collection for improved metagenomic analyses," Nature Biotechnology, 2019, 37(2):186-192.
Frese et al., "Formylglycine aldehyde Tag—protein engineering through a novel post-translational modification," ChemBioChem., 2009, 10(3):425-27.
Fu et al., "Continuous Polony Gels for Tissue Mapping with High Resolution and RNA Capture Efficiency," bioRxiv, 2021, 20 pages.
Fu et al., "Counting individual DNA molecules by the stochastic attachment of diverse labels," PNAS, 2011, 108(22):9026-9031.
Fu et al., "Repeat subtraction-mediated sequence capture from a complex genome," Plant J., Jun. 2010, 62(5):898-909.
Fullwood et al., "Next-generation DNA sequencing of paired-end tags (PET) for transcriptome and genome analyses," Genome Res., 2009, 19(4):521-532.
Ganguli et al., "Pixelated spatial gene expression analysis from tissue," Nat Commun., Jan. 2018, 9(1):202, 9 pages.
Gansauge et al., "Single-stranded DNA library preparation from highly degraded DNA using T4 DNA ligase," Nucleic Acids Res., Jun. 2017, 45(10):e79, 10 pages.
Gao et al., "A highly homogeneous expansion microscopy polymer composed of tetrahedron-like monomers," bioRxiv, Oct. 22, 2019, 23 pages (Preprint).
Gao et al., "Q&A: Expansion microscopy," BMC Biology, 15:50, 9 pages, 2017.
Gene@arrays[online], BeadArray Technology, available on or before Feb. 14, 2015, via Internet Archive: Wayback Machine URL <https://web.archive.org/web/20150214084616/http://genearrays.com/services/microarrays/illumina/beadarray-technology/>, [retrieved on Jan. 30, 2020], 3 pages.
Gerard et al., "Excess dNTPs minimize RNA hydrolysis during reverse transcription," Biotechniques, Nov. 2002, 33(5):984, 986, 988, 990.
Gilar et al., "Study of phosphorothioate-modified oligonucleotide resistance to 3'-exonuclease using capillary electrophoresis," J Chromatogr B Biomed Sci Appl., Aug. 28, 1998, 714(1):13-20.
Gill et al., "Nucleic acid isothermal amplification technologies: a review," Nucleosides Nucleotides Nucleic Acids, Mar. 2008, 27(3):224-43.
Glass et al., "SIMPLE: a sequential immunoperoxidase labeling and erasing method," J. Histochem. Cytochem., Oct. 2009, 57(10):899-905.
Gloor, "Gene targeting in *Drosophila*," Methods Mol Biol., 2004, 260:97-114.
Gnanapragasam, "Unlocking the molecular archive: the emerging use of formalin-fixed paraffin-embedded tissue for biomarker research in urological cancer," BJU International, 2009, 105(2):274-278.
Goh et al., "Highly Specific Multiplexed RNA Imaging In Tissues With Split-FISH," Nat Methods, Jun. 15, 2020, 17(7):689-693, 21 pages.
Goldkorn et al., "A simple and efficient enzymatic method for covalent attachment of DNA to cellulose. Application for hybridization-restriction analysis and for in vitro synthesis of DNA probes," Nucleic Acids Res., 1986, 14(22):9171-9191.
Goldmeyer et al., "Development of a novel one-tube isothermal reverse transcription thermophilic helicase-dependent amplification platform for rapid RNA detection," Journal of Molecular Diagnostics, American Society for Investigative Pathology and the Association for Molecular Pathology, Nov. 1, 2007, 9(5):639-644.
Goransson et al., "A single molecule array for digital targeted molecular analyses," Nucleic Acids Res., Nov. 25, 2009, 37(1):e7, 9 pages.
Goryshin et al., "Tn5 in vitro transposition," J Biol Chem., Mar. 1998, 273(13):7367-74.
Gracia Villacampa et al., "Genome-wide Spatial Expression Profiling in FFPE Tissues," bioRxiv, 2020, pp. 38 pages.
Grokhovsky, "Specificity of DNA cleavage by ultrasound," Molecular Biology, 2006, 40(2):276-283.
Grünweller et al., "Locked Nucleic Acid Oligonucleotides," BioDrugs, Jul. 2007, 21(4): 235-243.
Gu et al., "Multiplex single-molecule interaction profiling of DNA-barcoded proteins," Nature, Sep. 21, 2014, 515:554-557.
Gu et al., "Protein tag-mediated conjugation of oligonucleotides to recombinant affinity binders for proximity ligation," N Biotechnol., 2013, 30(2):144-152.
Gunderson et al., "Decoding randomly ordered DNA arrays," Genome Research, 2004, 14(5):870-877.
Guo et al., "Direct fluorescence analysis of genetic polymorphisms by hybridization with oligonucleotide arrays on glass supports," Nucleic Acids Res., Dec. 1994, 22(24):5456-65.
Gupta et al., "Single-cell isoform RNA sequencing characterizes isoforms in thousands of cerebellar cells," Nature Biotechnol., Oct. 2018, 36:1197-1202.
Hacisuleyman et al., "ModiBodies: A computational method for modifying nanobodies to improve their antigen binding affinity and specificity," bioRxiv, Journal of Biological Physics, posted Oct. 28, 2019, 20 pages.
Hadrup et al., "Parallel detection of antigen-specific T-cell responses by multidimensional encoding of MHC multimers," Nat. Methods., Jul. 2009, 6(7), 520-526.
Hafner et al., "Identification of microRNAs and other small regulatory RNAs using cDNA library sequencing," Methods, Jan. 2008, 44(1):3-12.
Hahnke et al., "Striptease on glass: validation of an improved stripping procedure for in situ microarrays," J Biotechnol., Jan. 2007, 128(1):1-13.
Hamaguchi et al., "Direct reverse transcription-PCR on oligo(dT)-immobilized polypropylene microplates after capturing total mRNA from crude cell lysates," Clin Chem., Nov. 1998, 44(11):2256-63.
Hamers-Casterman et al., "Naturally occurring antibodies devoid of light chains," Nature, 1993, 363:446-448 (Abstract Only).
Hanauer et al., "Separation of nanoparticles by gel electrophoresis according to size and shape," Nano Lett., Sep. 2007, 7(9):2881-5.
Hardenbol et al., "Highly multiplexed molecular inversion probe genotyping: over 10,000 targeted SNPs genotyped in a single tube assay," Genome Res., Feb. 2005, 15(2):269-75.
Hardenbol et al., "Multiplexed genotyping with sequence-tagged molecular inversion probes," Nature Biotechnol., Jun. 2003, 21(6):673-678.

(56) References Cited

OTHER PUBLICATIONS

Harmansa et al., "Protein binders and their applications in developmental biology," Development, Jan. 26, 2018, 145(2):dev148874, 13 pages.
Hayes et al., "Electrophoresis of proteins and nucleic acids: I-Theory," BMJ, Sep. 1989, 299(6703):843-6.
He et al., "In situ synthesis of protein arrays," Current Opinion in Biotechnology, 2008, 19(1):4-9.
He et al., "Printing protein arrays from DNA arrays," Nature Methods, 2008, 5(2):175-77.
He et al., "Ribosome display: Cell-free protein display technology," Briefings in Functional Genomics and Proteomics, Jul. 2002, 204-212.
He, "Cell-free protein synthesis: applications in proteomics and biotechnology," New Biotechnology, 2008, 25(2-3):126-132.
Healy, "Nanopore-based single-molecule DNA analysis," Nanomedicine (Lond), Aug. 2007, 2(4):459-81.
Hejatko et al., "In situ hybridization technique for mRNA detection in whole mount *Arabidopsis* samples," Nature Protocols, 2006, 1(4):1939-1946.
Hessner et al., "Genotyping of factor V G1691A (Leiden) without the use of PCR by invasive cleavage of oligonucleotide probes," Clin Chem., Aug. 2000, 46(8 Pt 1):1051-6.
Hiatt et al., "Parallel, tag-directed assembly of locally derived short sequence reads," Nature Methods, 2010, 7(2):119-25.
Ho et al., "Bacteriophage T4 RNA ligase 2 (gp24.1) exemplifies a family of RNA ligases found in all phylogenetic domains," PNAS, Oct. 2002, 99(20):12709-14.
Ho et al., "Characterization of an ATP-Dependent DNA Ligase Encoded by Chlorella Virus PBCV-1," Journal of Virology, Mar. 1997, 71(3):1931-1937.
Hobro et al, "An evaluation of fixation methods: Spatial and compositional cellular changes observed by Raman imaging," Vibrational Spectroscopy, Jul. 2017, 91:31-45.
Hoffman et al., "Formaldehyde crosslinking: a tool for the study of chromatin complexes," J Biol Chem., Oct. 2015, 290(44):26404-11.
Howell et al., "iFRET: An Improved Fluorescence System for DNA-Melting Analysis," Genome Research, 2002, 12:1401-1407.
Hsuih et al., "Novel, Ligation-Dependent PCR Assay for Detection of Hepatitis C Virus in Serum," Journal of Clinical Microbiology, Mar. 1996, 34(3):501-507.
Hu et al., "High reproducibility using sodium hydroxide-stripped long oligonucleotide DNA microarrays," Biotechniques, Jan. 2005, 38(1):121-4.
Huang et al., "RNA Display Methods for Discovery of Bioactive Macrocycles," Chemical Reviews, Nov. 5, 2018, 119(17):10360-10391.
Hughes et al., "Microfluidic Western blotting," PNAS, Dec. 2012, 109(52):21450-21455.
Hycultbiotech.com, [online], "Immunohistochemistry, Paraffin" Apr. 2010, retrieved on Apr. 16, 2020, retrieved from URL<https://www.hycultbiotech.com/media/wysiwyg/Protocol_Immunohistochemistry_Paraffin_2.pdf>, 3 pages.
Ichikawa et al., "In vitro transposition of transposon Tn3," J Biol. Chem., Nov. 1990, 265(31):18829-32, Abstract.
Illumina.com [online], "Ribo-ZeroR rRNA Removal Kit Reference Guide," Aug. 2016, retrieved on Apr. 26, 2022, retrieved from URL<https://jp.support.illumina.com/content/dam/illumina-support/documents/documentation/chemistry_documentation/ribosomal-depletion/ribo-zero/ribo-zero-reference-guide-15066012-02.pdf>, 36 pages.
Jamur et al., "Permeabilization of cell membranes.," Method Mol. Biol., 2010, 588:63-66.
Jemt et al., "An automated approach to prepare tissue-derived spatially barcoded RNA-sequencing libraries," Scientific Reports, 2016, 6:37137, 10 pages.
Jensen et al., "Zinc fixation preserves flow cytometry scatter and fluorescence parameters and allows simultaneous analysis of DNA content and synthesis, and intracellular and surface epitopes," Cytometry A., Aug. 2010, 77(8):798-804.
Jucá et al., "Effect of dimethyl sulfoxide on reverse transcriptase activity," Braz. J. Med. Biol. Res., Mar. 1995, 28(3):285-90.
Kalantari et al., "Deparaffinization of formalin-fixed paraffin-embedded tissue blocks using hot water instead of xylene," Anal Biochem., Aug. 2016, 507:71-3.
Kap et al., "Histological assessment of PAXgene tissue fixation and stabilization reagents," PLoS One, 2011, 6:e27704, 10 pages.
Kapteyn et al., "Incorporation of non-natural nucleotides into template-switching oligonucleotides reduces background and improves cDNA synthesis from very small RNA samples," BMC Genomics, Jul. 2010, 11:413, 9 pages.
Karmakar et al., "Organocatalytic removal of formaldehyde adducts from RNA and DNA bases," Nature Chemistry, Aug. 3, 2015, 7(9):752-758.
Kaya-Okur et al., "CUT&Tag for efficient epigenomic profiling of small samples and single cells," Apr. 2019, 10(1):1930, 10 pages.
Ke et al., "In situ sequencing for RNA analysis in preserved tissue and cells," Nat Methods., Sep. 2013, Supplementary Materials, 29 pages.
Kennedy-Darling et al., "Measuring the Formaldehyde Protein-DNA Cross-Link Reversal Rate," Analytical Chemistry, 2014, 86(12):5678-5681.
Kent et al., "Polymerase $\theta$ is a robust terminal transferase that oscillates between three different mechanisms during end-joining" Elife, Jun. 2016, 5:e13740, 25 pages.
Kirby et al., "Cryptic plasmids of *Mycobacterium avium*: Tn552 to the rescue," Mol Microbiol., Jan. 2002, 43(1):173-86.
Kleckner et al., "Tn10 and IS10 transposition and chromosome rearrangements: mechanism and regulation in vivo and in vitro," Curr Top Microbiol Immunol., 1996, 204:49-82.
Korbel et al., "Paired-end mapping reveals extensive structural variation in the human genome," Science, 2007, 318(5849):420-426.
Kozlov et al., "A highly scalable peptide-based assay system for proteomics," PLoS ONE, 2012, 7(6):e37441, 10 pages.
Kozlov et al., "A method for rapid protease substrate evaluation and optimization," Comb Chem High Throughput Screen, 2006, 9(6):481-87.
Kristensen et al., "High-Throughput Methods for Detection of Genetic Variation," BioTechniques, Feb. 2001, 30(2):318-332.
Krzywkowski et al., "Chimeric padlock and iLock probes for increased efficiency of targeted RNA detection," RNA, Jan. 2019, 25(1):82-89.
Krzywkowski et al., "Fidelity of RNA templated end-joining by Chlorella virus DNA ligase and a novel iLock assay with improved direct RNA detection accuracy," Nucleic Acids Research, Oct. 2017, 45(18):e161, 9 pages.
Kumar et al., "Template-directed oligonucleotide strand ligation, covalent intramolecular DNA circularization and catenation using click chemistry," J Am Chem Soc, May 2007, 129(21):6859-64.
Kurz et al., "cDNA—protein fusions: covalent protein-gene conjugates for the in vitro selection of peptides and proteins," ChemBioChem., 2001, 2(9):666-72.
Kwok, "High-throughput genotyping assay approaches," Pharmocogenomics, Feb. 2000, 1(1):95-100.
Lage et al., "Whole genome analysis of genetic alterations in small DNA samples using hyperbranched strand displacement amplification and array-CGH," Genome Research, 2003, 13(2):294-307.
Lahiani et al., "Enabling Histopathological Annotations on Immunofluorescent Images through Virtualization of Hematoxylin and Eosin," J Pathol Inform., Feb. 2018, 9:1, 8 pages.
Lampe et al., "A purified mariner transposase is sufficient to mediate transposition in vitro," EMBO J., Oct. 1996, 15(19):5470-9.
Landegren et al., "A Ligase-Mediated Gene Detection Technique," Science, 1988, 241(4869):1077-1080.
Landegren et al., "Reading bits of genetic information: methods for single-nucleotide polymorphism analysis," Genome Res., Aug. 1998, 8(8):769-76.
Langdale et al., "A rapid method of gene detection using DNA bound to Sephacryl," Gene, 1985, 36(3):201-210.
Larman et al., "Sensitive, multiplex and direct quantification of RNA sequences using a modified RASL assay," Nucleic Acids Research, 2014, 42(14):9146-9157.

(56) References Cited

OTHER PUBLICATIONS

Lee et al., "Fluorescent in situ sequencing (FISSEQ) of RNA for gene expression profiling in intact cells and tissues," Nature Protocols, 2015, 10(3):442-458.
Lee et al., "Improving the efficiency of genomic loci capture using oligonucleotide arrays for high throughput resequencing," BMC Genomics, Dec. 2009, 10:646, 12 pages.
Leriche et al., "Cleavable linkers in chemical biology," Bioorganic & Medicinal Chemistry, 2012, 20:571-582.
Li et al., "A new GSH-responsive prodrug of 5-aminolevulinic acid for photodiagnosis and photodynamic therapy of tumors," European Journal of Medicinal Chemistry, Nov. 2019, 181:111583, 9 pages.
Li et al., "A photocleavable fluorescent nucleotide for DNA sequencing and analysis," Proc. Natl. Acad. Sci., 2003, 100(2):414-419.
Li et al., "An activity-dependent proximity ligation platform for spatially resolved quantification of active enzymes in single cells," Nat Commun, Nov. 2017, 8(1):1775, 12 pages.
Li et al., "RASL-seq for Massively Parallel and Quantitative Analysis of Gene Expression," Curr Protoc Mol Biol., Apr. 2012, 4(13):1-10.
Li et al., "Review: a comprehensive summary of a decade development of the recombinase polymerase amplification," Analyst, Dec. 2018, 144(1):31-67.
Lin et al., "Highly multiplexed imaging of single cells using a high-throughput cyclic immunofluorescence method," Nat Commun., Sep. 2015, 6:8390, 7 pages.
Linnarsson, "Recent advances in DNA sequencing methods—general principles of sample preparation," Experimental Cell Research, 2010, 316(8):1339-1343.
Liu et al., "High-Spatial-Resolution Multi-Omics Atlas Sequencing of Mouse Embryos via Deterministic Barcoding in Tissue," BioRxiv, 2019, 55 pages.
Liu et al., "High-Spatial-Resolution Multi-Omics Sequencing via Deterministic Barcoding in Tissue," Cell, Nov. 13, 2020, 183(6):1665-1681, 36 pages.
Liu et al., "Spatial transcriptome sequencing of FFPE tissues at cellular level," bioRxiv 788992, Oct. 14, 2020, 39 pages.
Lizardi et al., "Mutation detection and single-molecule counting using isothermal rolling-circle amplification," Nat. Genet., 1998, 19(3):225-232.
Lou et al., "A review of room temperature storage of biospecimen tissue and nucleic acids for anatomic pathology laboratories and biorepositories," Clin Biochem., Mar. 2014, 47(4-5):267-73.
Lovatt et al., "Transcriptome in vivo analysis (TIVA) of spatially defined single cells in live tissue," Nature Methods, 2013, 11(2):190-196.
Lund et al., "Assessment of methods for covalent binding of nucleic acids to magnetic beads, Dynabeads, and the characteristics of the bound nucleic acids in hybridization reactions," Nucleic Acids Res., 1988, 16(22):10861-80.
Lundberg et al., "High-fidelity amplification using a thermostable DNA polymerase isolated from Pyrococcus furiosus," Gene, 1991, 108(1):1-6.
Lundberg et al., "Homogeneous antibody-based proximity extension assays provide sensitive and specific detection of low-abundant proteins in human blood," Nucleic Acids Res., 2011, 39(15):e102, 8 pages.
Lundberg et al., "Multiplexed homogeneous proximity ligation assays for high-throughput protein biomarker research in serological material," Mol Cell Proteomics, 2011, 10(4):M110.004978, 11 pages.
Lundin et al., "Increased throughput by parallelization of library preparation for massive sequencing," PLoS One, Apr. 2010, 5(4):e10029, 7 pages.
Lyamichev et al., "Invader assay for SNP genotyping," Methods Mol Biol., 2003, 212:229-40.
Lyamichev et al., "Polymorphism identification and quantitative detection of genomic DNA by invasive cleavage of oligonucleotide probes," Nat Biotechnol., Mar. 1999, 17(3):292-6.
Lyck et al., "Immunohistochemical markers for quantitative studies of neurons and glia in human neocortex," J Histochem Cytochem, 2008, 56(3):201-21.
Lykidis et al., "Novel zinc-based fixative for high quality DNA, RNA and protein analysis," Nucleic Acids Res., Jun. 2007, 35(12):e85, 10 pages.
Ma et al., "Isothermal amplification method for next-generation sequencing," PNAS, Aug. 12, 2013, 110(35):14320-14323.
MacBeath et al., "Printing proteins as microarrays for high-throughput function determination," Science, Sep. 2000, 289(5485):1760-1763.
MacIntyre, "Unmasking antigens for immunohistochemistry.," Br J Biomed Sci., 2001, 58(3):190-6.
Mamedov et al., "Preparing unbiased T-cell receptor and antibody cDNA libraries for the deep next generation sequencing profiling," Frontiers in Immunol., Dec. 23, 2013, 4(456):1-10.
Marx, "Method of the Year: spatially resolved transcriptomics," Nature Methods, 2021, 18(1):9-14.
Mathieson et al., "A Critical Evaluation of the PAXgene Tissue Fixation System: Morphology, Immunohistochemistry, Molecular Biology, and Proteomics," Am J Clin Pathol., Jul. 8, 2016, 146(1):25-40.
McCloskey et al., "Encoding PCR products with batch-stamps and barcodes," Biochem. Genet., 2007, 45(11-12):761-767.
Meers et al., "Improved CUT&RUN chromatin profiling tools," Elife, Jun. 2019, 8:e46314, 16 pages.
Merritt et al., "Multiplex digital spatial profiling of proteins and RNA in fixed tissue," Nat Biotechnol, May 2020, 38(5):586-599.
Metzker, "Sequencing technologies—the next generation," Nature Reviews Genetics, 2010, 11(1):31-46.
Miele et al., "Mapping cis- and trans-chromatin interaction networks using chromosome conformation capture (3C)," Methods Mol Biol., 2009, 464:105-21.
Mignardi et al., "Oligonucleotide gap-fill ligation for mutation detection and sequencing in situ," Nucleic Acids Research, Aug. 3, 2015, 43(22):e151, 12 pages.
Miller et al., "Basic concepts of microarrays and potential applications in clinical microbiology," Clinical Microbiology Reviews, 2009, 22(4):611-633.
Miller et al., "Chapter 11—Solid and Suspension Microarrays for Microbial Diagnostics," Methods in Microbiology, 2015, 42:395-431.
Miner et al., "Molecular barcodes detect redundancy and contamination in hairpin-bisulfite PCR," Nucleic Acids Res., Sep. 2004, 32(17):e135, 4 pages.
Mishra et al., "Three-dimensional genome architecture and emerging technologies: looping in disease," Genome Medicine, 2017, 9(1):87, 14 pages.
Mitra et al., "Digital genotyping and haplotyping with polymerase colonies," Proc. Natl. Acad. Sci. USA, May 2003, 100(10):5926-5931.
Miura et al., "Highly efficient single-stranded DNA ligation technique improves low-input whole-genome bisulfite sequencing by post-bisulfite adaptor tagging," Nucleic Acids Res., Sep. 2019, 47(15):e85, 10 pages.
Mizusawa et al., "A bacteriophage lambda vector for cloning with BamHI and Sau3A," Gene, 1982, 20(3):317-322.
Mohsen et al., "The Discovery of Rolling Circle Amplification and Rolling Circle Transcription," Acc Chem Res., Nov. 15, 2016, 49(11):2540-2550, 25 pages.
Morlan et al., "Selective depletion of rRNA enables whole transcriptome profiling of archival fixed tissue," PLoS One, Aug. 2012, 7(8):e42882, 8 pages.
Motea et al., "Terminal deoxynucleotidyl transferase: the story of a misguided DNA polymerase," Biochim Biophys Acta., May 2010, 1804(5):1151-66.
Mulder et al., "CapTCR-seq: hybrid capture for T-cell receptor repertoire profiling," Blood Advances, Dec. 2018, 2(23):3506-3514.
Nadji et al., "Immunohistochemistry of tissue prepared by a molecular-friendly fixation and processing system," Appl Immunohistochem Mol Morphol., Sep. 2005, 13(3):277-82.

(56) References Cited

OTHER PUBLICATIONS

Nallur et al., "Signal amplification by rolling circle amplification on DNA microarrays," Nucleic Acids Res., Dec. 1, 2001, 29(23):e118, 9 pages.
Nam et al., "Nanoparticle-Based Bio-Bar Codes for the Ultrasensitive Detection of Proteins," Science, Sep. 26, 2003, 301(5641):1884-1886.
Nandakumar et al., "How an RNA Ligase Discriminates RNA versus DNA Damage," Molecular Cell, 2004, 16:211-221.
Nandakumar et al., "RNA Substrate Specificity and Structure-guided Mutational Analysis of Bacteriophage T4 RNA Ligase 2," Journal of Biological Chemistry, Jul. 2004, 279(30):31337-31347.
Ncbi.nlm.nih.gov, [online], "Molecular Inversion Probe Assay," available on or before Oct. 14, 2014, via Internet Archive: Wayback Machine URL<https://web.archive.org/web/20141014124037/https://www.ncbi.nlm.nih.gov/probe/docs/techmip/>, retrieved on Jun. 16, 2021, retrieved from URL<https://www.ncbi.nlm.nih.gov/probe/docs/techmip/>, 2 pages.
Ng et al., "Gene identification signature (GIS) analysis for transcriptome characterization and genome annotation," Nature Methods, 2005, 2(2):105-111.
Nichols et al., "RNA Ligases," Curr Protoc Mol Biol., Oct. 2008, 84(1):3.15.1-3.15.4.
Niedringhaus et al., "Landscape of next-generation sequencing technologies," Anal Chem., Jun. 2011, 83(12):4327-41.
Nikiforov et al., "The use of 96-well polystyrene plates for DNA hybridization-based assays: an evaluation of different approaches to oligonucleotide immobilization," Anal Biochem, May 1995, 227(1):201-9.
Niklas et al., "Selective permeabilization for the high-throughput measurement of compartmented enzyme activities in mammalian cells," Anal Biochem, Sep. 2011, 416(2):218-27.
Nilsson et al., "RNA-templated DNA ligation for transcript analysis," Nucleic Acids Res., Jan. 2001, 29(2):578-81.
Nowak, "Entering the Postgenome Era," Science, 1995, 270(5235):368-71.
Ohtsubo et al., "Bacterial insertion sequences," Curr Top Microbiol Immunol., 1996, 204:1-26.
Oksuz et al., "Systematic evaluation of chromosome conformation capture assays," Nature Methods, Sep. 2021, 18:1046-1055.
Olivier, "The Invader assay for SNP genotyping," Mutat. Res., Jun. 2005, 573(1-2):103-110.
Orenstein et al., "γPNA FRET Pair Miniprobes for Quantitative Fluorescent In Situ Hybridization to Telomeric DNA in Cells and Tissue," Molecules, Dec. 2, 2017, 22(12):2117, 15 pages.
Ozsolak et al., "Digital transcriptome profiling from attomole-level RNA samples," Genome Res., Apr. 2010, 20(4):519-25.
Pandey et al., "Inhibition of terminal deoxynucleotidyl transferase by adenine dinucleotides. Unique inhibitory action of Ap5A," FEBS Lett., Mar. 1987, 213(1):204-8.
Park et al., "Single cell trapping in larger microwells capable of supporting cell spreading and proliferation," Microfluid Nanofluid, 2010, 8:263-268.
Passow et al., "RNAlater and flash freezing storage methods nonrandomly influence observed gene expression in RNAseq experiments," bioRxiv, Jul. 2018, 28 pages.
PCT International Search Report and Written Opinion in International Appln. No. PCT/US2022/039956, dated Dec. 6, 2022, 17 pages.
Pellestor et al., "The peptide nucleic acids (PNAs), powerful tools for molecular genetics and cytogenetics," Eur J Hum Genet., Sep. 2004, 12(9):694-700.
Pemov et al., "DNA analysis with multiplex microarray-enhanced PCR," Nucl. Acids Res., Jan. 2005, 33(2):e11, 9 pages.
Penno et al., "Stimulation of reverse transcriptase generated cDNAs with specific indels by template RNA structure: retrotransposon, dNTP balance, RT-reagent usage," Nucleic Acids Res., Sep. 2017, 45(17):10143-10155.
Perler et al., "Intervening sequences in an Archaea DNA polymerase gene," Proc Natl Acad Sci USA, Jun. 1992, 89(12):5577-5581.
Perocchi et al., "Antisense artifacts in transcriptome microarray experiments are resolved by actinomycin D," Nucleic Acids Res., 2007, 35(19):e128, 7 pages.
Petterson et al., "Generations of sequencing technologies," Genomics, 2009, 93(2):105-111.
Picelli et al., "Full-length RNA-seq from single cells using Smart-seq2," Nat Protoc, Jan. 2014, 9(1):171-81.
Picelli et al., "Tn5 transposase and tagmentation procedures for massively scaled sequencing projects," Genome Res., Dec. 2014, 24(12):2033-40.
Piepenburg et al., "DNA detection using recombination proteins," PLoS Biol., Jul. 2006, 4(7):e204, 7 pages.
Plasterk, "The Tcl/mariner transposon family," Curr Top Microbiol Immunol., 1996, 204:125-43.
Plongthongkum et al., "Advances in the profiling of DNA modifications: cytosine methylation and beyond," Nature Reviews Genetics, Aug. 2014, 15(10):647-661.
Polsky-Cynkin et al., "Use of DNA immobilized on plastic and agarose supports to detect DNA by sandwich hybridization," Clin. Chem., 1985, 31(9):1438-1443.
Porreca et al., "Polony DNA sequencing," Curr Protoc Mol Biol., Nov. 2006, Chapter 7, Unit 7.8, pp. 7.8.1-7.8.22.
U.S. Appl. No. 61/267,363, filed Dec. 7, 2009, 33 pages.
Qiu et al., "Combination probes with intercalating anchors and proximal fluorophores for DNA and RNA detection," Nucleic Acids Research, Sep. 2016, 44(17):e138, 12 pages.
Raab et al., "Human tRNA genes function as chromatin insulators," EMBO J., Jan. 2012, 31(2):330-50.
Raj et al., "Imaging individual mRNA molecules using multiple singly labeled probes," Nature Methods, Oct. 2008, 5(10):877-879, 9 pages.
Ranki et al., "Sandwich hybridization as a convenient method for the detection of nucleic acids in crude samples," Gene, 1983, 21(1-2):77-85.
Redmond et al., "Single-cell TCRseq: paired recovery of entire T-cell alpha and beta chain transcripts in T-cell receptors from single-cell RNAseq," Genome Med, 2016, 8:80, 12 pages.
Reinartz et al., "Massively parallel signature sequencing (MPSS) as a tool for in-depth quantitative gene expression profiling in all organisms," Brief Funct Genomic Proteomic, Feb. 2002, 1(1):95-104.
Reznikoff, "Tn5 as a model for understanding DNA transposition," Mol Microbiol., Mar. 2003, 47(5):1199-206.
Ristic et al., "Detection of Protein-Protein Interactions and Post-translational Modifications Using the Proximity Ligation Assay: Application to the Study of the SUMO Pathway," Methods Mol. Biol., 2016, 1449:279-90.
Rodriques et al., "Slide-seq: A scalable technology for measuring genome-wide expression at high spatial resolution," Science, 2019, 363(6434):1463-1467.
Rohland et al., "Partial uracil-DNA-glycosylase treatment for screening of ancient DNA," Phil. Trans. R. Soc. B, Jan. 19, 2015, 370(1660): 20130624, 11 pages.
Ronaghi et al., "A sequencing method based on real-time pyrophosphate," Science, Jul. 1998, 281(5375):363-365.
Ronaghi et al., "Real-time DNA sequencing using detection of pyrophosphate release," Analytical Biochemistry, Nov. 1996, 242(1):84-89.
Ronaghi, "Pyrosequencing sheds light on DNA sequencing," Genome Res, Jan. 2001, 11(1):3-11.
Roy et al., "Assessing long-distance RNA sequence connectivity via RNA-templated DNA-DNA ligation," eLife, 2015, 4:e03700, 21 pages.
Salmén et al., "Barcoded solid-phase RNA capture for Spatial Transcriptomics profiling in mammalian tissue sections," Nature Protocols, Oct. 2018, 13(11):2501-2534.
Saxonov et al., "10x Genomics, Mastering Biology to Advance Human Health," PowerPoint, 10x, 2020, 41 pages.
Schena et al., "Quantitative monitoring of gene expression patterns with a complementary DNA microarray," Science, Oct. 1995, 270(5235):467-470.

(56) References Cited

OTHER PUBLICATIONS

Schmidl et al., "ChIPmentation: fast, robust, low-input ChIP-seq for histones and transcription factors," Nature Methods, Oct. 2015, 12:963-965.
Schouten et al., "Relative quantification of 40 nucleic acid sequences by multiplex ligation-dependent probe amplification," Nucleic Acids Res., Jun. 2002, 30(12):e57, 13 pages.
Schweitzer et al., "Immunoassays with rolling circle DNA amplification: A versatile platform for ultrasensitive antigen detection," Proc. Natl Acad. Sci. USA, May 22, 2000, 97:10113-119.
Schweitzer et al., "Multiplexed protein profiling on microarrays by rolling-circle amplification," Nature Biotechnology, Apr. 2002, 20(4):359-365.
Schwers et al., "A high-sensitivity, medium-density, and target amplification-free planar waveguide microarray system for gene expression analysis of formalin-fixed and paraffin-embedded tissue," Clin. Chem., Nov. 2009, 55(11):1995-2003.
Shalon et al., "A DNA microarray system for analyzing complex DNA samples using two-color fluorescent probe hybridization," Genome Res., Jul. 1996, 6(7):639-45.
Shelbourne et al., "Fast copper-free click DNA ligation by the ring-strain promoted alkyne-azide cycloaddition reaction," Chem. Commun., 2011, 47(22):6257-6259.
Shendure et al., "Accurate multiplex polony sequencing of an evolved bacterial genome," Science, 2005, 309(5741):1728-1732.
Simonis et al., "Nuclear organization of active and inactive chromatin domains uncovered by chromosome conformation capture-on-chip (4C)," Nat Genet., Nov. 2006, 38(11):1348-54.
Singh et al., "High-throughput targeted long-read single cell sequencing reveals the clonal and transcriptional landscape of lymphocytes," Nat Commun., Jul. 2019, 10(1):3120, 13 pages.
Skene et al., "An efficient targeted nuclease strategy for high-resolution mapping of DNA binding sites," Elife, Jan. 2017, 6:e21856, 35 pages.
Slomovic et al., "Addition of poly(A) and poly(A)-rich tails during RNA degradation in the cytoplasm of human cells," Proc Natl Acad Sci USA, Apr. 2010, 107(16):7407-12.
Sountoulidis et al., "SCRINSHOT, a spatial method for single-cell resolution mapping of cell states in tissue sections," PLoS Biol., Nov. 2020, 18(11):e3000675, 32 pages.
Spiess et al., "A highly efficient method for long-chain cDNA synthesis using trehalose and betaine," Anal. Biochem., Feb. 2002, 301(2):168-74.
Spitale et al., "Structural imprints in vivo decode RNA regulatory mechanisms," Nature, 2015, 519(7544):486-90.
Stahl et al., "Visualization and analysis of gene expression in tissue sections by spatial transcriptomics," Science, Jul. 2016, 353(6294):78-82.
Stahl et al., "Visualization and analysis of gene expression in tissue sections by spatial transcriptomics," Supplementary Materials, Science, Jul. 2016, 353(6294):78-82, 41 pages.
Stimpson et al., "Real-time detection of DNA hybridization and melting on oligonucleotide arrays by using optical wave guides," Proc Natl Acad Sci USA, Jul. 1995, 92(14):6379-83.
Stoddart et al., "Single-nucleotide discrimination in immobilized DNA oligonucleotides with a biological nanopore," PNAS USA., May 2009, 106(19):7702-7707.
Stoeckius et al., "Cell Hashing with barcoded antibodies enables multiplexing and doublet detection for single cell genomics," Genome Biology, Dec. 19, 2018, 19: 224, 12 pages.
Stoeckius et al., "Simultaneous epitope and transcriptome measurement in single cells," Nature Methods, Jul. 31, 2017, 14(9):865-868.
Strell et al., "Placing RNA in context and space—methods for spatially resolved transcriptomics," The FEBS Journal, 2019, 286(8):1468-1481.
Stroh et al., "Quantum dots spectrally distinguish multiple species within the tumor milieu in vivo," Nat Med., Jun. 2005, 11(6):678-82.
Su et al., "Restriction enzyme selection dictates detection range sensitivity in chromatin conformation capture-based variant-to-gene mapping approaches," bioRxiv, Dec. 15, 2020, 22 pages.
Sun et al., "Statistical Analysis of Spatial Expression Pattern for Spatially Resolved Transcriptomic Studies," Nature Methods, Jan. 27, 2020, 17(2): 193-200.
Sutherland et al., "Utility of formaldehyde cross-linking and mass spectrometry in the study of protein-protein interactions," J. Mass Spectrom., Jun. 2008, 43(6):699-715.
Svensson et al., "SpatialDE: identification of spatially variable genes," Nature Methods, May 2018, 15:343-346, 15 pages.
Takei et al., "Integrated Spatial Genomics Reveals Global Architecture Of Single Nuclei," Nature, Jan. 27, 2021, 590(7845):344-350, 53 pages.
Taylor et al., "Mitochondrial DNA mutations in human disease," Nature Reviews Genetics, May 2005, 6(5):389-402.
Tentori et al., "Detection of Isoforms Differing by a Single Charge Unit in Individual Cells," Chem. Int. Ed., 2016, 55(40):12431-5.
Tian et al., "Antigen peptide-based immunosensors for rapid detection of antibodies and antigens," Anal Chem, 2009, 81(13):5218-5225.
Tijssen et al., "Overview of principles of hybridization and the strategy of nucleic acid assays" in Techniques in Biochemistry and Molecular Biology—Hybridization with Nucleic Acid Probes, 1993, 24(Chapter 2), 65 pages.
Tolbert et al., "New methods for proteomic research: preparation of proteins with N-terminal cysteines for labeling and conjugation," Angewandte Chemie International Edition, Jun. 2002, 41(12):2171-4.
Toubanaki et al., "Dry-reagent disposable biosensor for visual genotyping of single nucleotide polymorphisms by oligonucleotide ligation reaction: application to pharmacogenetic analysis," Hum Mutat., Aug. 2008, 29(8):1071-8.
Trejo et al., "Extraction-free whole transcriptome gene expression analysis of FFPE sections and histology-directed subareas of tissue," PLoS ONE, Feb. 2019, 14(2):e0212031, 22 pages.
Tu et al., "TCR sequencing paired with massively parallel 3' RNA-seq reveals clonotypic T cell signatures," Nature Immunology, Dec. 2019, 20(12):1692-1699.
Twyman et al., "Techniques Patents for SNP Genotyping," Pharmacogenomics, Jan. 2003, 4(1):67-79.
Ueno et al., "cDNA Display: Rapid Stabilitzation of mRNA Display," Antibody-Drug Conjugates, Methods in Molecular Biology, Jan. 2012, pp. 113-135.
Ulery et al., "Biomedical Applications of Biodegradable Polymers," J Polym Sci B Polym Phys., Jun. 2011, 49(12):832-864.
U.S. Appl. No. 60/416,118 Fan et al., Multiplex Nucleic Acid Analysis Using Archived or Fixed Samples, filed Oct. 3, 2002, 22 pages.
Van Gelder et al., "Amplified RNA synthesized from limited quantities of heterogeneous cDNA," Proc. Natl. Acad. Sci. USA, 1990, 87(5):1663-1667.
Vandenbroucke et al., "Quantification of splice variants using real-time PCR," Nucleic Acids Research, 2001, 29(13):e68, 7 pages.
Vandernoot et al., "cDNA normalization by hydroxyapatite chromatography to enrich transcriptome diversity in RNA-seq applications," Biotechniques, Dec. 2012, 53(6):373-80.
Vasiliskov et al., "Fabrication of microarray of gel-immobilized compounds on a chip by copolymerization," Biotechniques, Sep. 1999, 27(3):592-606.
Vázquez Bernat et al., "High-Quality Library Preparation for NGS-Based Immunoglobulin Germline Gene Inference and Repertoire Expression Analysis," Front Immunol., Apr. 2019, 10:660, 12 pages.
Velculescu et al., "Serial analysis of gene expression," Science, Oct. 1995, 270(5235):484-7.
Vickovic et al., "High-definition spatial transcriptomics for in situ tissue profiling," Nat Methods, Oct. 2019, 16(10):987-990.
Vickovic et al., "SM-Omics: An automated Platform for High-Throughput Spatial Multi-Omics," bioRxiv, Oct. 2020, 40 pages.
Vincent et al., "Helicase-dependent isothermal DNA amplification," EMBO Rep., Aug. 2004, 5(8):795-800.

(56) References Cited

OTHER PUBLICATIONS

Viollet et al., "T4 RNA ligase 2 truncated active site mutants: improved tools for RNA analysis," BMC Biotechnol., Jul. 2011, 11:72, 14 pages.
Vogelstein et al., "Digital PCR," Proceedings of the National Academy of Sciences, Aug. 1999, 96(16):9236-9241.
Waichman et al., "Functional immobilization and patterning of proteins by an enzymatic transfer reaction," Analytical chemistry, 2010, 82(4):1478-85.
Walker et al., "Strand displacement amplification—an isothermal, in vitro DNA amplification technique," Nucleic Acids Research, 1992, 20(7):1691-1696.
Wang et al., "Concentration gradient generation methods based on microfluidic systems," RSC Adv., 2017, 7:29966-29984.
Wang et al., "High-fidelity mRNA amplification for gene profiling," Nature Biotechnology, Apr. 2000, 18(4):457-459.
Wang et al., "Imaging-based pooled CRISPR screening reveals regulators of IncRNA localization," Proc Natl Acad Sci USA, May 2019, 116(22):10842-10851.
Wang et al., "Optimization of Process Conditions for Infected Animal Tissues by Alkaline Hydrolysis Technology," Procedia Environmental Sciences, 2016, 31:366-374.
Wang et al., "Tagmentation-based whole-genome bisulfite sequencing," Nature Protocols, Oct. 2013, 8(10):2022-2032.
Wang, "RNA amplification for successful gene profiling analysis," J Transl Med., Jul. 2005, 3:28, 11 pages.
Weinreich et al., "Evidence that the cis Preference of the Tn5 Transposase is Caused by Nonproductive Multimerization," Genes and Development, Oct. 1994, 8(19):2363-2374.
Wiedmann et al., "Ligase chain reaction (LCR)—overview and applications," PCR Methods Appl., Feb. 1994, 3(4):S51-64.
Wilson et al., "New transposon delivery plasmids for insertional mutagenesis in Bacillus anthracis," J Microbiol Methods, Dec. 2007, 71(3):332-5.
Wohnhaas et al., "DMSO cryopreservation is the method of choice to preserve cells for droplet-based single-cell RNA sequencing," Scientific Reports, Jul. 2019, 9(1):10699, 14 pages.
Wolf et al., "Rapid hybridization kinetics of DNA attached to submicron latex particles," Nucleic Acids Res, 1987, 15(7):2911-2926.
Wong et al., "Direct Site-Selective Covalent Protein Immobilization Catalyzed by a Phosphopantetheinyl Transferase," J. Am. Chem Soc, 2008, 130(37):12456-64.
Worthington et al., "Cloning of random oligonucleotides to create single-insert plasmid libraries," Anal Biochem, 2001, 294(2):169-175.
Wu et al., "Detection DNA Point Mutation with Rolling-Circle Amplification Chip," IEEE, 2010 4th International Conference on Bioinformatics and Biomedical Engineering, Jun. 2010, 4 pages.
Wu et al., "RollFISH achieves robust quantification of single-molecule RNA biomarkers in paraffin-embedded tumor tissue samples," Commun Biol., Nov. 2018, 1:209, 8 pages.
Xia et al., "Spatial transcriptome profiling by MERFISH reveals subcellular RNA compartmentalization and cell cycle-dependent gene expression", Proceedings of the National Academy of Sciences, Sep. 2019, 116(39):19490-19499.
Yasukawa et al., "Effects of organic solvents on the reverse transcription reaction catalyzed by reverse transcriptases from avian myeloblastosis virus and Moloney murine leukemia virus," Biosci Biotechnol Biochem., 2010, 74(9):1925-30.
Yeakley et al., "A trichostatin A expression signature identified by TempO-Seq targeted whole transcriptome profiling," PLoS One, May 2017, 12(5):e0178302, 22 pages.
Yeakley et al., "Profiling alternative splicing on fiber-optic arrays," Nature biotechnology, 2002, 20:353-358.
Yershov et al., "DNA analysis and diagnostics on oligonucleotide microchips," Proc. Natl. Acad. Sci. USA, May 1996, 93(10):4913-4918.
Yin et al., "Genetically encoded short peptide tag for versatile protein labeling by Sfp phosphopantetheinyl transferase," PNAS, 2005, 102(44):15815-20.
Zahra et al., "Assessment of Different Permeabilization Methods of Minimizing Damage to the Adherent Cells for Detection of Intracellular RNA by Flow Cytometry," Avicenna Journal of Medical Biotechnology, Jan. 1, 2014, 6(1):38-46.
Zhang et al., "Archaeal RNA ligase from Thermoccocus kodakarensis for template dependent ligation," RNA Biol., Jan. 2017, 14(1):36-44.
Zhang et al., "Assembling DNA through Affinity Binding to Achieve Ultrasensitive Protein Detection," Angew Chem Int Ed Engl., 2013, 52(41):10698-705.
Zhang et al., "Binding-induced DNA assembly and its application to yoctomole detection of proteins," Anal Chem, 2012, 84(2):877-884.
Zhang et al., "Genome-wide open chromatin regions and their effects on the regulation of silk protein genes in Bombyx mori," Sci Rep., Oct. 2017, 7(1):12919, 9 pages.
Zhang et al., "Multiplex ligation-dependent probe amplification (MLPA) for ultrasensitive multiplexed microRNA detection using ribonucleotide-modified DNA probes†," Chem. Commun., 2013, 49:10013-10015.
Zhao et al., "Isothermal Amplification of Nucleic Acids," Chemical Reviews, Nov. 2015, 115(22):12491-12545.
Zheng et al., "Origins of human mitochondrial point mutations as DNA polymerase gamma-mediated errors," Mutat. Res., 2006, 599(1-2):11-20.
Zhou et al., "Genetically encoded short peptide tags for orthogonal protein labeling by Sfp and AcpS phosphopantetheinyl transferases," ACS Chemical Biol., 2007, 2(5):337-346.
Zhu et al., "Reverse transcriptase template switching: a SMART approach for full-length cDNA library construction," Biotechniques, Apr. 2001, 30(4):892-897.

METHODS, COMPOSITIONS, AND SYSTEMS FOR IDENTIFYING ANTIGEN-BINDING MOLECULES

CROSS-REFERENCE TO RELATED APPLICATIONS

This application is a National Stage Application under 35 U.S.C. § 371 and claims the benefit of International Application No. PCT/US2022/039956, filed Aug. 10, 2022, which claims priority to U.S. Provisional Patent Application No. 63/232,386, filed on Aug. 12, 2021. The content of that application is incorporated herein by reference in its entirety.

BACKGROUND

Cells within a tissue have differences in cell morphology and/or function due to varied analyte levels (e.g., gene and/or protein expression) within the different cells. The specific position of a cell within a tissue (e.g., the cell's position relative to neighboring cells or the cell's position relative to the tissue microenvironment) can affect, e.g., the cell's morphology, differentiation, fate, viability, proliferation, behavior, signaling, and cross-talk with other cells in the tissue.

Spatial heterogeneity has been previously studied using techniques that typically provide data for a handful of analytes in the context of intact tissue or a portion of a tissue (e.g., tissue section), or provide significant analyte data from individual, single cells, but fails to provide information regarding the position of the single cells from the originating biological sample (e.g., tissue).

Therapeutic antibodies are an essential class of drugs which are widely used in the treatment of cancer, autoimmunity, inflammatory diseases, and/or for drug delivery to target antigens. Current antibody therapeutics discovery workflows typically involve (1) target assessment and validation, (2) screening preparation, (3) hit generation, screening, and lead selection. These classic workflows are limited in that a target of interest must generally be known prior to screening. Since there are few known targets, many antibody campaigns target the same limited number of existing drug targets, while novel targets are seldom explored. Furthermore, the screening process generally utilizes in vitro models or cell lines which do not accurately reflect the in vivo context, where targets can be embedded within a complex tissue environment. Furthermore, the screening processes are not typically suitable for identifying antibody therapeutics for personalized medicine. Therefore, a need remains for methods, compositions, and systems for improved antibody therapeutics discovery.

SUMMARY

The present disclosure features methods of generating an antigen-binding molecule/nucleic acid conjugate library, methods of displaying (e.g., ribosomal display, mRNA/cDNA display) antigen-binding molecules/nucleic acid libraries, methods of identifying antigen-binding molecules that selectively bind to antigens in a test biological sample and determining the location of the antigen in the test biological sample, and compositions and kits thereof.

Therapeutic antibodies are an essential class of drugs which are widely used in the treatment of cancer, autoimmunity, and inflammatory diseases, and/or for drug delivery to target antigens. Conventional antibodies (e.g., IgG) are large in size (e.g., about 150 kDa) and comprise two heavy and two light chains. Smaller, single-chain, antigen-binding molecules (e.g., about 15 kDa) can be attractive alternatives to conventional antibodies. In some examples, single-chain antibodies include scFv single-chain antibodies. In some examples, single-chain antibodies include single variable domain on a heavy chain (VHH) antibodies, also known as nanobodies. These single-chain antibodies are generally more stable, easier to generate large libraries, and easier to screen than conventional antibodies. Additionally, the single-chain antibodies can be screened via various display techniques. In some examples, the display technique is ribosomal display. In some examples, the display technique is mRNA/cDNA display. These screening techniques can also be performed in combination with a spatial array (e.g., an array comprising a plurality of capture probes, where a capture probe includes a spatial barcode and a capture domain). For example, single-chain antibodies can be displayed in an in vitro system, screened against a healthy biological sample (e.g., healthy tissue section), and the non-binding antibodies can be collected (e.g., washed off) the biological sample and screened against a diseased biological sample (e.g., a tumor sample). Non-binding antibodies can be removed from the diseased biological sample (e.g., washed off) and the remaining single-chain antibodies bound to an antigen present in the diseased can be captured on a spatial array as described herein and identified.

Provided herein are methods of generating an antigen-binding molecule/nucleic acid conjugate library, where an antigen-binding molecule/nucleic acid conjugate of the antigen-binding molecule/nucleic acid conjugate library includes an antigen binding molecule linked to a nucleic acid encoding the antigen-binding molecule, the method including: (a) providing a plurality of in vitro transcribed mRNAs, where an mRNA of the plurality of in vitro transcribed mRNAs includes in a 5' to 3' direction: (i) an analyte capture sequence that hybridizes to a capture domain of a capture probe, (ii) a sequence encoding the antigen-binding molecule, (iii) a primer binding sequence, (iv) a universal domain attached to a donor oligonucleotide, where the donor oligonucleotide includes a linker having a nucleotide sequence and a protein translation inhibitor; and (b) in vitro translating the plurality of in vitro transcribed mRNAs, thereby generating the antigen-binding molecule/nucleic acid conjugate library antigen-binding molecule mRNA.

In some embodiments, the method includes a prior step of attaching the donor oligonucleotide to the universal domain via ligation. In some embodiments, the ligation includes ligation with a splint oligonucleotide. In some embodiments, the splint oligonucleotide is substantially complementary to the linker of the donor oligonucleotide, or a portion thereof. In some embodiments, the splint oligonucleotide is substantially complementary to the universal domain, or a portion thereof.

In some embodiments, the ligating includes Y-ligation. In some embodiments, the linker of the donor oligonucleotide is substantially complementary to the universal domain, or a portion thereof. In some embodiments, the method includes ligating the 5' end of the donor oligonucleotide to the 3' end of the universal domain.

In some embodiments, the ligating includes a ligase. In some embodiments, the ligase is selected from the group consisting of T4 DNA ligase, T4 RNA ligase, PBCV-1 ligase and a Chlorella DNA ligase.

In some embodiments, the ligating includes ultra-violet (UV) light cross-linking. In some embodiments, the linker of the donor oligonucleotide is substantially complementary to the universal domain, or a portion thereof. In some embodiments, the 5' end of the linker includes a UV light photoreactive moiety. In some embodiments, the UV light photoreactive moiety includes psoralen.

In some embodiments, the linker of the donor oligonucleotide is substantially complementary to the universal domain, or a portion thereof.

In some embodiments, the protein translation inhibitor is non-covalently attached to the mRNA. In some embodiments, the protein translation inhibitor is covalently attached to the mRNA. In some embodiments, the protein translation inhibitor molecule is puromycin.

In some embodiments, the antigen-binding molecule includes a single-chain antigen-binding molecule. In some embodiments, the single-chain antigen binding molecule includes a single-chain variable fragment (scFv). In some embodiments, the single-chain antigen binding molecule includes a nanobody.

In some embodiments, the method includes generating a cDNA complementary to the mRNA to produce a double stranded DNA/RNA duplex.

In some embodiments, generating the cDNA includes reverse transcribing the mRNA. In some embodiments, reverse transcription includes use of a primer that hybridizes to the universal domain of the mRNA.

In some embodiments, the protein translation inhibitor does not include a stop codon.

Also provided herein are methods of identifying an antigen-binding molecule that selectively binds to an antigen in a biological sample, the method including: (a) providing an array including a plurality of capture probes, where a capture probe of the plurality includes (i) a spatial barcode and (ii) a capture domain; (b) contacting the biological sample with members of an antigen-binding molecule/nucleic acid conjugate library, where an antigen-binding molecule/nucleic acid conjugate of the library includes an antigen binding molecule linked to a nucleic acid encoding the antigen-binding molecule, and where the nucleic acid includes a cDNA/RNA duplex, where the RNA strand of the duplex includes: (i) a sequence complementary to the analyte capture sequence which binds a capture domain of a capture probe, (ii) a sequence encoding an antigen-binding molecule, (iii) a primer binding sequence, and (iv) a universal domain attached to a donor oligonucleotide, where the donor oligonucleotide includes a linker having a nucleotide sequence and a protein translation inhibitor, (c) removing one or more unbound antigen-binding molecule/nucleic acid conjugates from the biological sample; and (d) capturing one or more cDNAs of the antigen-binding molecule/nucleic acid conjugates onto one or more capture probes of the array, where an analyte capture sequence of the cDNA binds to the capture domain of the capture probe.

In some embodiments, the method includes determining (i) the sequence of the spatial barcode or a complement thereof, and (ii) all or a portion of the sequence of the cDNA, or a complement thereof. In some embodiments, the method includes using the determined sequences of (i) the sequence of the spatial barcode or a complement thereof and (ii) all or a portion of the sequence of the cDNA or a complement thereof to identify an antigen-binding molecule that selectively binds to an antigen in the biological sample and determine the location of the antigen in the biological sample. In some embodiments, the determining includes sequencing.

In some embodiments, step (c) is performed before (a), after (a), or after (b).

In some embodiments, the members of the antigen-binding molecule/nucleic acid conjugate library were selected by a prior step of contacting a control biological sample with the antigen-binding molecule/nucleic acid conjugate library, and selecting members of the library that did not bind to the control biological sample.

In some embodiments, the control biological sample is a healthy biological sample. In some embodiments, the biological sample includes one or more healthy regions and one or more disease regions. In some embodiments, the biological sample is a diseased biological sample. In some embodiments, the diseased biological sample is a tumorous biological sample.

In some embodiments, the method includes releasing the cDNA from the antigen-binding molecule/nucleic acid conjugate prior to the capturing step. In some embodiments, the releasing includes an RNase. In some embodiments, the RNase is selected from the group consisting of RNase A, RNase C, RNase H, or RNase I. In some embodiments, the releasing includes heat.

In some embodiments, the method includes permeabilizing the biological sample, the test biological sample, or both. In some embodiments, the method includes imaging the biological sample. In some embodiments, the method includes staining the biological sample. In some embodiments, the staining includes hematoxylin and eosin (H&E) staining.

In some embodiments, the array includes one or more features. In some embodiments, the one or more features includes a bead.

In some embodiments, the capture probe includes any one or more of: a cleavage domain, a unique molecular identifier (UMI), one or more functional domain, and combinations thereof.

In some embodiments, the antigen-binding molecule is a single-chain antigen-binding molecule. In some embodiments, the single-chain antigen-binding molecule includes a single-chain variable fragment (scFv). In some embodiments, the single-chain antigen-binding molecule includes a nanobody.

In some embodiments, the cDNA complementary to the nucleic acid of the antigen-binding molecule/nucleic acid conjugate is generated by reverse transcription.

In some embodiments, the method includes capturing a nucleic acid analyte or derivative thereof from the biological sample, where the nucleic acid analyte binds to the capture domain of the capture probe. In some embodiments, the nucleic acid analyte, or derivative thereof, includes DNA. In some embodiments, the nucleic acid analyte, or derivative thereof, includes RNA (e.g., mRNA).

In some embodiments, the method includes: (a) contacting a first probe and a second probe with the biological sample, where the first probe and the second probe each include one or more sequences that are substantially complementary to sequences of an analyte, and where the second probe includes a capture probe capture domain that is complementary to all or a portion of the capture domain; (b) hybridizing the first probe and the second probe to the analyte; (c) generating a ligation product by ligating the first probe and the second probe; (d) releasing the ligation product from the analyte; (e) hybridizing the ligation product to the capture domain; and (g) determining (i) all or part of the sequence of the ligation product bound to the capture domain, or a complement thereof, and (ii) all of the spatial barcode, or a complement thereof, and using the determined sequences of (i) and (ii) to identify the location of the analyte in the biological sample.

In some embodiments, the method includes identifying the antigen bound by the antigen-binding molecule/nucleic acid complex. In some embodiments, the identifying includes mass spectrometry. In some embodiments, the identifying includes determining differential gene expression patterns between the control biological sample and the test biological sample. In some embodiments, the identifying includes determining differential gene expression patterns within the biological sample.

In some embodiments, the biological sample is disposed on the spatial array including the plurality of capture probes. In some embodiments, the biological sample is disposed on the substrate.

In some embodiments, the method includes aligning the substrate with the spatial array, such that at least a portion of the biological sample is aligned with at least a portion of the spatial array.

Also provided herein are compositions including: an in vitro transcribed mRNA in a 5' to 3' direction: (i) a sequence complementary to an analyte capture sequence that hybridized to a capture domain of a capture probe, (ii) a sequence encoding an antigen-binding molecule, (iii) a primer binding sequence, and (iv) a universal sequence.

In some embodiments, the method includes a donor oligonucleotide attached to the universal sequence of the mRNA. In some embodiments, the donor oligonucleotide includes a linker having a sequence and a protein translation inhibitor. In some embodiments, the protein translation inhibitor includes a translation inhibitor molecule including puromycin.

In some embodiments, the donor oligonucleotide is attached the universal sequence of the mRNA with a splint oligonucleotide. In some embodiments, the splint oligonucleotide includes a substantially complementary sequence to the universal domain and a substantially complementary sequence to the linker of the donor oligonucleotide.

In some embodiments, the protein translation inhibitor does not include a stop codon.

Also provided herein are composition including: an antigen-binding molecule/nucleic acid conjugate including: (i) a sequence complementary to an analyte capture sequence, (ii) a sequence encoding an antigen-binding molecule, (iii) a primer binding sequence, (iv) a constant sequence; (v) a protein translation inhibitor molecule; and (vi) the antigen-binding molecule.

In some embodiments, the antigen-binding molecule includes a single-chain antigen binding molecule. In some embodiments, the single-chain antigen binding molecule includes an scFv. In some embodiments, the single-chain antigen binding molecule includes a nanobody.

In some embodiments, the composition includes a cDNA hybridized to the nucleic acid of the antigen-binding molecule/nucleic acid conjugate. In some embodiments, the cDNA is generated by reverse transcription.

Also provided herein are compositions including: (a) an array including a plurality of capture probes, where a capture probe includes: (i) a spatial barcode; and (ii) a capture domain; and b) a cDNA including in the 5' to 3' direction: (i) a sequence complementary to a universal domain; (ii) a sequence complementary to a primer binding site; (iii) a sequence complementary to a sequence encoding an antigen-binding molecule; and (iv) an analyte capture sequence, where the analyte capture sequence is bound to the capture domain of the capture probe.

Also provided herein are compositions including: an array including a plurality of capture probes, where a capture probe includes: (i) a spatial barcode; and (ii) a capture domain; and b) an extended cDNA product including in the 5' to 3' direction: (i) a sequence complementary to a universal domain; (ii) a sequence complementary to a primer binding site; (iii) a sequence complementary to a sequence encoding an antigen-binding molecule; (iv) an analyte capture sequence, where the analyte capture sequence is bound to the capture domain of the capture probe; (v) a sequence complementary the capture probe; and c) an extended capture probe including a sequence complementary to the cDNA using the cDNA as an extension template.

In some embodiments, the capture probe includes one or more functional domains, a UMI, a cleavage domain, and combinations thereof.

All publications, patents, and patent applications mentioned in this specification are herein incorporated by reference to the same extent as if each individual publication, patent, patent application, or item of information was specifically and individually indicated to be incorporated by reference. To the extent publications, patents, patent applications, and items of information incorporated by reference contradict the disclosure contained in the specification, the specification is intended to supersede and/or take precedence over any such contradictory material.

Where values are described in terms of ranges, it should be understood that the description includes the disclosure of all possible sub-ranges within such ranges, as well as specific numerical values that fall within such ranges irrespective of whether a specific numerical value or specific sub-range is expressly stated.

The term "each," when used in reference to a collection of items, is intended to identify an individual item in the collection but does not necessarily refer to every item in the collection, unless expressly stated otherwise, or unless the context of the usage clearly indicates otherwise.

Various embodiments of the features of this disclosure are described herein. However, it should be understood that such embodiments are provided merely by way of example, and numerous variations, changes, and substitutions can occur to those skilled in the art without departing from the scope of this disclosure. It should also be understood that various alternatives to the specific embodiments described herein are also within the scope of this disclosure.

DESCRIPTION OF DRAWINGS

The following drawings illustrate certain embodiments of the features and advantages of this disclosure. These embodiments are not intended to limit the scope of the appended claims in any manner. Like reference symbols in the drawings indicate like elements.

Figure 5A:
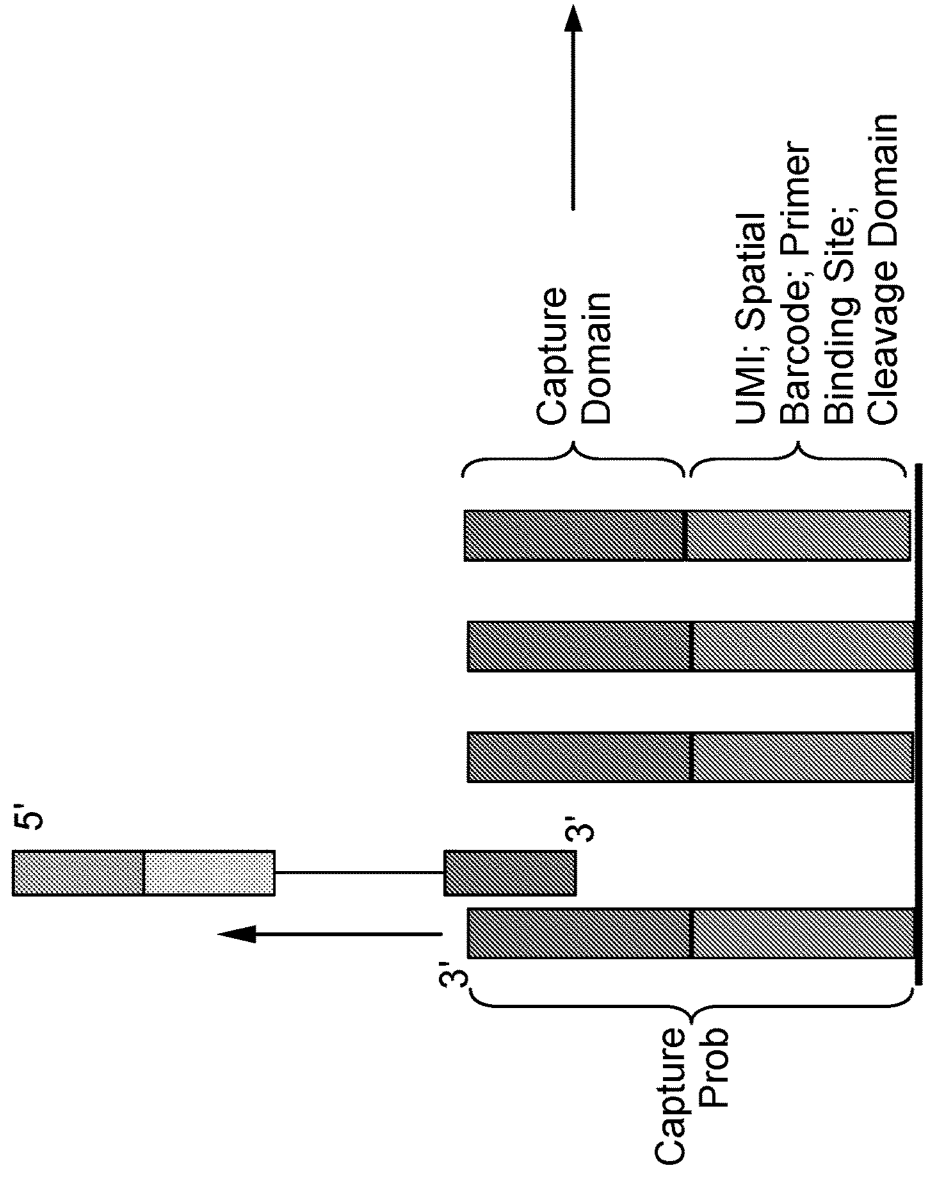
FIGS. 5A-B show a capture probe hybridized to the analyte capture sequence of the cDNA of the antigen-binding molecule/nucleic acid conjugate members (FIG.
Figure 5B:
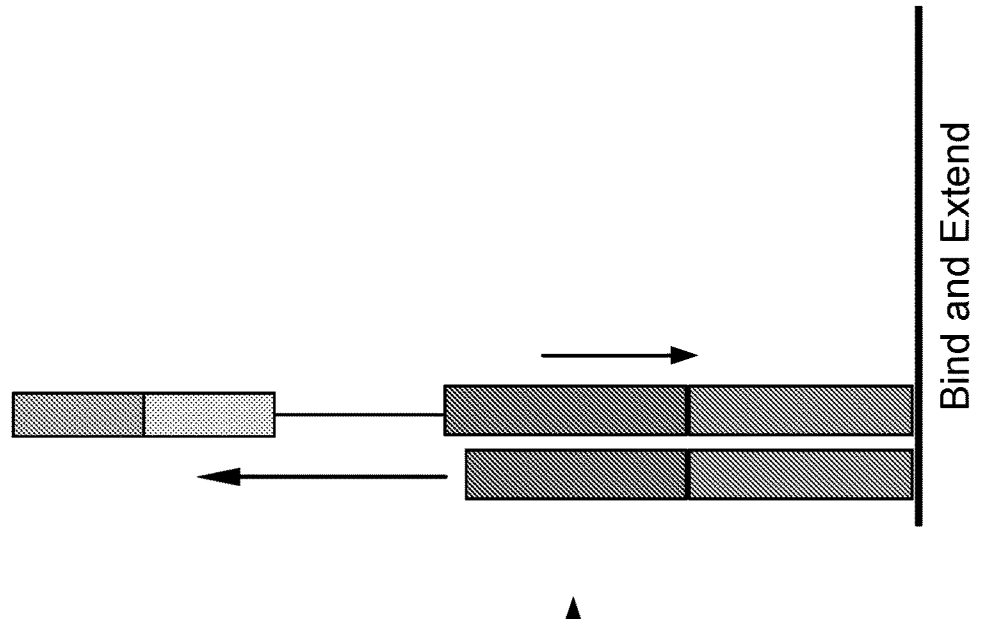

5A) and extension of the 3' end of the capture probe and the 3' end of the cDNA (FIG. 5B).

Figures 6A, 6B:
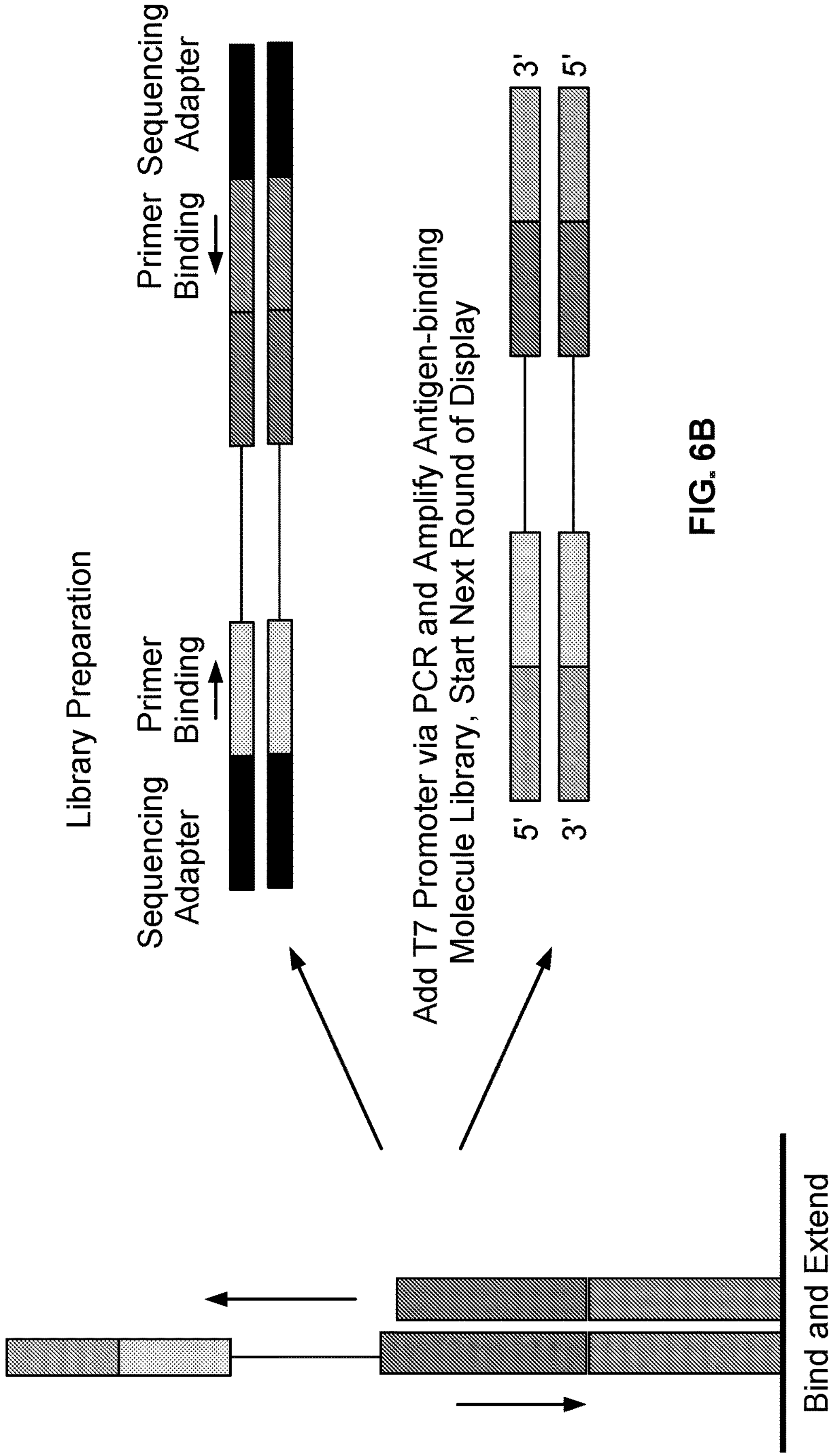

FIGS. 6A-B show extension of the 3' end of the capture probe and the 3' end of the cDNA (FIG. 6A) and the resulting nucleic acid library in FIG. 6B.

DETAILED DESCRIPTION

The present disclosure features methods of generating an antigen-binding molecule/nucleic acid conjugate library, methods of displaying (e.g., ribosomal display, mRNA/cDNA display) antigen-binding molecules/nucleic acid libraries, methods of identifying antigen-binding molecules that selectively bind to antigens in a test biological sample, and determining the location of the antigen in the test biological sample, and compositions and kits thereof.

Therapeutic antibodies are an essential class of drugs which are widely used in the treatment of cancer, autoimmunity, and inflammatory diseases, and/or for drug delivery to target antigens. Conventional antibodies (e.g., IgG) are large in size (e.g., about 150 kDa) and comprise two heavy and two light chains. Smaller, single-chain, antigen-binding molecules (e.g., about 15 kDa) can be attractive alternatives to conventional antibodies. In some examples, single-chain antibodies include scFv single-chain antibodies. In some examples, single-chain antibodies include VHH antibodies (e.g., nanobodies). These single-chain antibodies are generally more stable, easier to generate large libraries, and easier to screen than conventional antibodies. Additionally, the single-chain antibodies can be screened via various display techniques. In some examples, the display technique is ribosomal display. In some examples, the display technique is mRNA/cDNA display. These screening techniques can also be performed in combination with a spatial array (e.g., an array comprising a plurality of capture probes, where a capture probe comprises a spatial barcode and a capture domain). For example, single-chain antibodies can be displayed in an in vitro system, screened against a healthy biological sample (e.g., healthy tissue section), and the non-binding antibodies can be collected (e.g., washed off) the biological sample and screened against a diseased biological sample (e.g., a tumor sample). Non-binding antibodies can be removed from the diseased biological sample (e.g., washed off) and the remaining single-chain antibodies bound to an antigen present in the diseased can be captured on a spatial array as described herein and identified.

Spatial analysis methodologies and compositions described herein can provide a vast amount of analyte and/or expression data for a variety of analytes within a biological sample at high spatial resolution, while retaining native spatial context. Spatial analysis methods and compositions can include, e.g., the use of a capture probe including a spatial barcode (e.g., a nucleic acid sequence that provides information as to the location or position of an analyte within a cell or a tissue sample (e.g., mammalian cell or a mammalian tissue sample)) and a capture domain that is capable of binding to an analyte (e.g., a protein and/or a nucleic acid) produced by and/or present in a cell. Spatial analysis methods and compositions can also include the use of a capture probe having a capture domain that captures an intermediate agent for indirect detection of an analyte. For example, the intermediate agent can include a nucleic acid sequence (e.g., a barcode) associated with the intermediate agent. Detection of the intermediate agent is therefore indicative of the analyte in the cell or tissue sample.

Non-limiting aspects of spatial analysis methodologies and compositions are described in U.S. Pat. Nos. 10,774,374, 10,724,078, 10,480,022, 10,059,990, 10,041,949, 10,002,316, 9,879,313, 9,783,841, 9,727,810, 9,593,365, 8,951,726, 8,604,182, 7,709,198, U.S. Patent Application Publication Nos. 2020/239946, 2020/080136, 2020/0277663, 2020/024641, 2019/330617, 2019/264268, 2020/256867, 2020/224244, 2019/194709, 2019/161796, 2019/085383, 2019/055594, 2018/216161, 2018/051322, 2018/0245142, 2017/241911, 2017/089811, 2017/067096, 2017/029875, 2017/0016053, 2016/108458, 2015/000854, 2013/171621, WO 2018/091676, WO 2020/176788, Rodriques et al., Science 363(6434):1463-1467, 2019; Lee et al., Nat. Protoc. 10(3):442-458, 2015; Trejo et al., PLoS ONE 14(2): e0212031, 2019; Chen et al., Science 348(6233):aaa6090, 2015; Gao et al., BMC Biol. 15:50, 2017; and Gupta et al., Nature Biotechnol. 36:1197-1202, 2018; the Visium Spatial Gene Expression Reagent Kits User Guide (e.g., Rev C, dated June 2020), and/or the Visium Spatial Tissue Optimization Reagent Kits User Guide (e.g., Rev C, dated July 2020), both of which are available at the 10× Genomics Support Documentation website, and can be used herein in any combination. Further non-limiting aspects of spatial analysis methodologies and compositions are described herein.

Some general terminology that may be used in this disclosure can be found in Section (I)(b) of WO 2020/176788 and/or U.S. Patent Application Publication No. 2020/0277663. Typically, a "barcode" is a label, or identifier, that conveys or is capable of conveying information (e.g., information about an analyte in a sample, a bead, and/or a capture probe). A barcode can be part of an analyte, or independent of an analyte. A barcode can be attached to an analyte. A particular barcode can be unique relative to other barcodes. For the purpose of this disclosure, an "analyte" can include any biological substance, structure, moiety, or component to be analyzed. The term "target" can similarly refer to an analyte of interest.

Analytes can be broadly classified into one of two groups: nucleic acid analytes, and non-nucleic acid analytes. Examples of non-nucleic acid analytes include, but are not limited to, lipids, carbohydrates, peptides, proteins, glycoproteins (N-linked or O-linked), lipoproteins, phosphoproteins, specific phosphorylated or acetylated variants of proteins, amidation variants of proteins, hydroxylation variants of proteins, methylation variants of proteins, ubiquitylation variants of proteins, sulfation variants of proteins, viral proteins (e.g., viral capsid, viral envelope, viral coat, viral accessory, viral glycoproteins, viral spike, etc.), extracellular and intracellular proteins, antibodies, and antigen binding fragments. In some embodiments, the analyte(s) can be localized to subcellular location(s), including, for example, organelles, e.g., mitochondria, Golgi apparatus, endoplasmic reticulum, chloroplasts, endocytic vesicles, exocytic vesicles, vacuoles, lysosomes, etc. In some embodiments, analyte(s) can be peptides or proteins, including without limitation antibodies and enzymes. Additional examples of analytes can be found in Section (I)(c) of WO 2020/176788 and/or U.S. Patent Application Publication No. 2020/0277663. In some embodiments, an analyte can be detected indirectly, such as through detection of an intermediate agent, for example, a ligation product or an analyte capture agent (e.g., an oligonucleotide-conjugated antibody), such as those described herein.

A "biological sample" is typically obtained from the subject for analysis using any of a variety of techniques including, but not limited to, biopsy, surgery, and laser capture microscopy (LCM), and generally includes cells and/or other biological material from the subject. In some embodiments, a biological sample can be a tissue section. In some embodiments, a biological sample can be a fixed and/or stained biological sample (e.g., a fixed and/or stained tissue section). Non-limiting examples of stains include histological stains (e.g., hematoxylin and/or eosin) and immunological stains (e.g., fluorescent stains). In some embodiments, a biological sample (e.g., a fixed and/or stained biological sample) can be imaged. Biological samples are also described in Section (I)(d) of WO 2020/176788 and/or U.S. Patent Application Publication No. 2020/0277663.

In some embodiments, a biological sample is permeabilized with one or more permeabilization reagents. For example, permeabilization of a biological sample can facilitate analyte capture. Exemplary permeabilization agents and conditions are described in Section (I)(d)(ii)(13) or the Exemplary Embodiments Section of WO 2020/176788 and/or U.S. Patent Application Publication No. 2020/0277663.

Array-based spatial analysis methods involve the transfer of one or more analytes from a biological sample to an array of features on a substrate, where each feature is associated with a unique spatial location on the array. Subsequent analysis of the transferred analytes includes determining the identity of the analytes and the spatial location of the analytes within the biological sample. The spatial location of an analyte within the biological sample is determined based on the feature to which the analyte is bound (e.g., directly or indirectly) on the array, and the feature's relative spatial location within the array.

A "capture probe" refers to any molecule capable of capturing (directly or indirectly) and/or labelling an analyte (e.g., an analyte of interest) in a biological sample. In some embodiments, the capture probe is a nucleic acid or a polypeptide. In some embodiments, the capture probe includes a barcode (e.g., a spatial barcode and/or a unique molecular identifier (UMI)) and a capture domain). In some embodiments, a capture probe can include a cleavage domain and/or a functional domain (e.g., a primer-binding site, such as for next-generation sequencing (NGS)). See, e.g., Section (II)(b) (e.g., subsections (i)-(vi)) of WO 2020/176788 and/or U.S. Patent Application Publication No. 2020/0277663. Generation of capture probes can be achieved by any appropriate method, including those described in Section (II)(d)(ii) of WO 2020/176788 and/or U.S. Patent Application Publication No. 2020/0277663.

Figure 1:
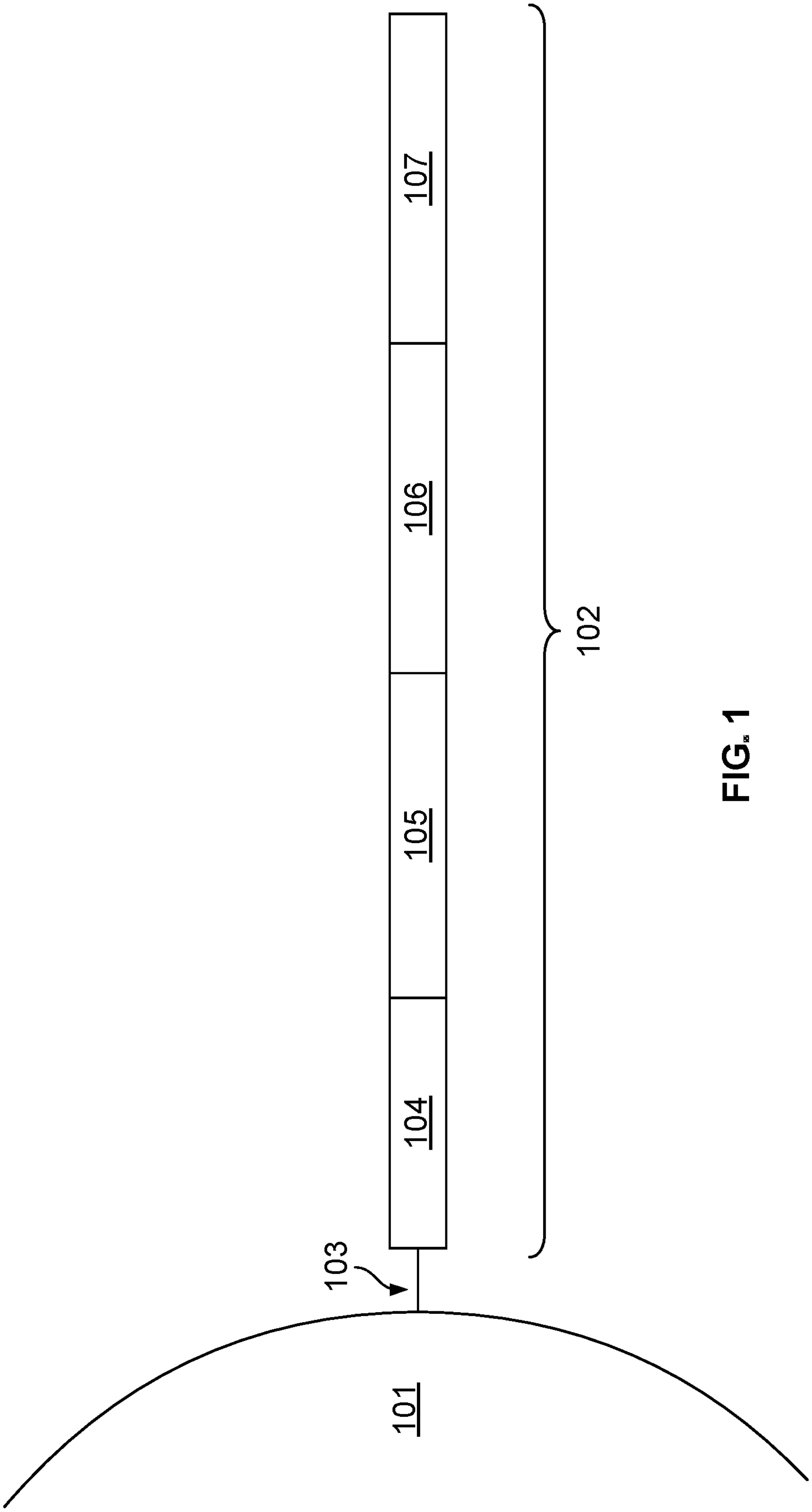
FIG. 1 is a schematic diagram showing an example of a barcoded capture probe, as described herein.

FIG. 1 is a schematic diagram showing an exemplary capture probe, as described herein. As shown, the capture probe 102 is optionally coupled to a feature 101 by a cleavage domain 103, such as a disulfide linker. The capture probe can include a functional sequence 104 that is useful for subsequent processing. The functional sequence 104 can include all or a part of sequencer specific flow cell attachment sequence (e.g., a P5 or P7 sequence), all or a part of a sequencing primer sequence, (e.g., a R1 primer binding site, a R2 primer binding site), or combinations thereof. The capture probe can also include a spatial barcode 105. The capture probe can also include a unique molecular identifier (UMI) sequence 106. While FIG. 1 shows the spatial barcode 105 as being located upstream (5') of UMI sequence 106, it is to be understood that capture probes wherein UMI sequence 106 is located upstream (5') of the spatial barcode 105 is also suitable for use in any of the methods described herein. The capture probe can also include a capture domain 107 to facilitate capture of a target analyte. In some embodiments, the capture probe comprises one or more additional functional sequences that can be located, for example between the spatial barcode 105 and the UMI sequence 106, between the UMI sequence 106 and the capture domain 107, or following the capture domain 107. The capture domain can have a sequence complementary to a sequence of a nucleic acid analyte. The capture domain can have a sequence complementary to a capture handle sequence present in an analyte capture agent. The capture domain can have a sequence complementary to a splint oligonucleotide. Such splint oligonucleotide, in addition to having a sequence complementary to a capture domain of a capture probe, can have a sequence of a nucleic acid analyte, and/or a capture handle sequence described herein.

The functional sequences can generally be selected for compatibility with any of a variety of different sequencing systems, e.g., Ion Torrent Proton or PGM, Illumina sequencing instruments, PacBio, Oxford Nanopore, etc., and the requirements thereof. In some embodiments, functional sequences can be selected for compatibility with non-commercialized sequencing systems. Examples of such sequencing systems and techniques, for which suitable functional sequences can be used, include (but are not limited to) Ion Torrent Proton or PGM sequencing, Illumina sequencing, PacBio SMRT sequencing, and Oxford Nanopore sequencing. Further, in some embodiments, functional sequences can be selected for compatibility with other sequencing systems, including non-commercialized sequencing systems.

In some embodiments, the spatial barcode 105 and functional sequences 104 is common to all of the probes attached to a given feature (e.g., a bead, a well, a spot on an array). In some embodiments, the UMI sequence 106 of a capture probe attached to a given feature is different from the UMI sequence of a different capture probe attached to the given feature.

In some embodiments, more than one analyte type (e.g., nucleic acids and proteins) from a biological sample can be detected (e.g., simultaneously or sequentially) using any appropriate multiplexing technique, such as those described in Section (IV) of WO 2020/176788 and/or U.S. Patent Application Publication No. 2020/0277663.

In some embodiments, detection of one or more analytes (e.g., protein analytes) can be performed using one or more analyte capture agents. As used herein, an "analyte capture agent" refers to an agent that interacts with an analyte (e.g., an analyte in a biological sample) and with a capture probe (e.g., a capture probe attached to a substrate or a feature) to identify the analyte. In some embodiments, the analyte capture agent includes: (i) an analyte binding moiety (e.g., that binds to an analyte), for example, an antibody or antigen-binding fragment thereof; (ii) analyte binding moiety barcode; and (iii) an analyte capture sequence. As used herein, the term "analyte binding moiety barcode" refers to a barcode that is associated with or otherwise identifies the analyte binding moiety. As used herein, the term "analyte capture sequence" refers to a region or moiety configured to hybridize to, bind to, couple to, or otherwise interact with a capture domain of a capture probe. In some cases, an analyte binding moiety barcode (or portion thereof) may be able to be removed (e.g., cleaved) from the analyte capture agent. Additional description of analyte capture agents can be found in Section (II)(b)(ix) of WO 2020/176788 and/or Section (II)(b)(viii) U.S. Patent Application Publication No. 2020/0277663.

There are at least two methods to associate a spatial barcode with one or more neighboring cells, such that the spatial barcode identifies the one or more cells, and/or contents of the one or more cells, as associated with a particular spatial location. One method is to promote analytes or analyte proxies (e.g., intermediate agents) out of a cell and towards a spatially-barcoded array (e.g., including spatially-barcoded capture probes). Another method is to cleave spatially-barcoded capture probes from an array and promote the spatially-barcoded capture probes towards and/or into or onto the biological sample.

In some cases, capture probes may be configured to prime, replicate, and consequently yield optionally barcoded extension products from a template (e.g., a DNA or RNA template, such as an analyte or an intermediate agent (e.g., a ligation product or an analyte capture agent), or a portion thereof), or derivatives thereof (see, e.g., Section (II)(b)(vii) of WO 2020/176788 and/or U.S. Patent Application Publication No. 2020/0277663 regarding extended capture probes). In some cases, capture probes may be configured to form ligation products with a template (e.g., a DNA or RNA template, such as an analyte or an intermediate agent, or portion thereof), thereby creating ligations products that serve as proxies for a template.

As used herein, an "extended capture probe" refers to a capture probe having additional nucleotides added to the terminus (e.g., 3' or 5' end) of the capture probe thereby extending the overall length of the capture probe. For example, an "extended 3' end" indicates additional nucleotides were added to the most 3' nucleotide of the capture probe to extend the length of the capture probe, for example, by polymerization reactions used to extend nucleic acid molecules including templated polymerization catalyzed by a polymerase (e.g., a DNA polymerase or a reverse transcriptase). In some embodiments, extending the capture probe includes adding to a 3' end of a capture probe a nucleic acid sequence that is complementary to a nucleic acid sequence of an analyte or intermediate agent specifically bound to the capture domain of the capture probe. In some embodiments, the capture probe is extended using reverse transcription. In some embodiments, the capture probe is extended using one or more DNA polymerases. The extended capture probes include the sequence of the capture probe and the sequence of the spatial barcode of the capture probe.

In some embodiments, extended capture probes are amplified (e.g., in bulk solution or on the array) to yield quantities that are sufficient for downstream analysis, e.g., via DNA sequencing. In some embodiments, extended capture probes (e.g., DNA molecules) act as templates for an amplification reaction (e.g., a polymerase chain reaction).

Additional variants of spatial analysis methods, including in some embodiments, an imaging step, are described in Section (II)(a) of WO 2020/176788 and/or U.S. Patent Application Publication No. 2020/0277663. Analysis of captured analytes (and/or intermediate agents or portions thereof), for example, including sample removal, extension of capture probes, sequencing (e.g., of a cleaved extended capture probe and/or a cDNA molecule complementary to an extended capture probe), sequencing on the array (e.g., using, for example, in situ hybridization or in situ ligation approaches), temporal analysis, and/or proximity capture, is described in Section (II)(g) of WO 2020/176788 and/or U.S. Patent Application Publication No. 2020/0277663. Some quality control measures are described in Section (II)(h) of WO 2020/176788 and/or U.S. Patent Application Publication No. 2020/0277663.

Spatial information can provide information of biological and/or medical importance. For example, the methods and compositions described herein can allow for: identification of one or more biomarkers (e.g., diagnostic, prognostic, and/or for determination of efficacy of a treatment) of a disease or disorder; identification of a candidate drug target for treatment of a disease or disorder; identification (e.g., diagnosis) of a subject as having a disease or disorder; identification of stage and/or prognosis of a disease or disorder in a subject; identification of a subject as having an increased likelihood of developing a disease or disorder; monitoring of progression of a disease or disorder in a subject; determination of efficacy of a treatment of a disease or disorder in a subject; identification of a patient subpopulation for which a treatment is effective for a disease or disorder; modification of a treatment of a subject with a disease or disorder; selection of a subject for participation in a clinical trial; and/or selection of a treatment for a subject with a disease or disorder.

Spatial information can provide information of biological importance. For example, the methods and compositions described herein can allow for: identification of transcriptome and/or proteome expression profiles (e.g., in healthy and/or diseased tissue); identification of multiple analyte types in close proximity (e.g., nearest neighbor analysis); determination of up-and/or down-regulated genes and/or proteins in diseased tissue; characterization of tumor microenvironments; characterization of tumor immune responses; characterization of cells types and their co-localization in tissue; and identification of genetic variants within tissues (e.g., based on gene and/or protein expression profiles associated with specific disease or disorder biomarkers).

Typically, for spatial array-based methods, a substrate functions as a support for direct or indirect attachment of capture probes to features of the array. A "feature" is an entity that acts as a support or repository for various molecular entities used in spatial analysis. In some embodiments, some or all of the features in an array are functionalized for analyte capture. Exemplary substrates are described in Section (II)(c) of WO 2020/176788 and/or U.S. Patent Application Publication No. 2020/0277663. Exemplary features and geometric attributes of an array can be found in Sections (II)(d)(i), (II)(d)(iii), and (II)(d)(iv) of WO 2020/176788 and/or U.S. Patent Application Publication No. 2020/0277663.

Generally, analytes and/or intermediate agents (or portions thereof) can be captured when contacting a biological sample with a substrate including capture probes (e.g., a substrate with capture probes embedded, spotted, printed, fabricated on the substrate, or a substrate with features (e.g., beads, wells) comprising capture probes). As used herein, "contact." "contacted," and/or "contacting," a biological sample with a substrate refers to any contact (e.g., direct or indirect) such that capture probes can interact (e.g., bind covalently or non-covalently (e.g., hybridize)) with analytes from the biological sample. Capture can be achieved actively (e.g., using electrophoresis) or passively (e.g., using diffusion). Analyte capture is further described in Section (II)(e) of WO 2020/176788 and/or U.S. Patent Application Publication No. 2020/0277663.

In some cases, spatial analysis can be performed by attaching and/or introducing a molecule (e.g., a peptide, a lipid, or a nucleic acid molecule) having a barcode (e.g., a spatial barcode) to a biological sample (e.g., to a cell in a biological sample). In some embodiments, a plurality of molecules (e.g., a plurality of nucleic acid molecules) having a plurality of barcodes (e.g., a plurality of spatial barcodes) are introduced to a biological sample (e.g., to a plurality of cells in a biological sample) for use in spatial analysis. In some embodiments, after attaching and/or introducing a molecule having a barcode to a biological sample, the biological sample can be physically separated (e.g., dissociated) into single cells or cell groups for analysis. Some such methods of spatial analysis are described in Section (III) of WO 2020/176788 and/or U.S. Patent Application Publication No. 2020/0277663.

In some cases, spatial analysis can be performed by detecting multiple oligonucleotides that hybridize to an analyte. In some instances, for example, spatial analysis can be performed using RNA-templated ligation (RTL). Methods of RTL have been described previously. See, e.g., Credle et al., *Nucleic Acids Res.* 2017 Aug. 21; 45(14):e128. Typically, RTL includes hybridization of two oligonucleotides to adjacent sequences on an analyte (e.g., an RNA molecule, such as an mRNA molecule). In some instances, the oligonucleotides are DNA molecules. In some instances, one of the oligonucleotides includes at least two ribonucleic acid bases at the 3' end and/or the other oligonucleotide includes a phosphorylated nucleotide at the 5' end. In some instances, one of the two oligonucleotides includes a capture domain (e.g., a poly(A) sequence, a non-homopolymeric sequence). After hybridization to the analyte, a ligase (e.g., Splint® ligase) ligates the two oligonucleotides together, creating a ligation product. In some instances, the two oligonucleotides hybridize to sequences that are not adjacent to one another. For example, hybridization of the two oligonucleotides creates a gap between the hybridized oligonucleotides. In some instances, a polymerase (e.g., a DNA polymerase) can extend one of the oligonucleotides prior to ligation. After ligation, the ligation product is released from the analyte. In some instances, the ligation product is released using an endonuclease (e.g., RNAse H). The released ligation product can then be captured by capture probes (e.g., instead of direct capture of an analyte) on an array, optionally amplified, and sequenced, thus determining the location and optionally the abundance of the analyte in the biological sample.

During analysis of spatial information, sequence information for a spatial barcode associated with an analyte is obtained, and the sequence information can be used to provide information about the spatial distribution of the analyte in the biological sample. Various methods can be used to obtain the spatial information. In some embodiments, specific capture probes and the analytes they capture are associated with specific locations in an array of features on a substrate. For example, specific spatial barcodes can be associated with specific array locations prior to array fabrication, and the sequences of the spatial barcodes can be stored (e.g., in a database) along with specific array location information, so that each spatial barcode uniquely maps to a particular array location.

Alternatively, specific spatial barcodes can be deposited at predetermined locations in an array of features during fabrication such that at each location, only one type of spatial barcode is present so that spatial barcodes are uniquely associated with a single feature of the array. Where necessary, the arrays can be decoded using any of the methods described herein so that spatial barcodes are uniquely associated with array feature locations, and this mapping can be stored as described above.

When sequence information is obtained for capture probes and/or analytes during analysis of spatial information, the locations of the capture probes and/or analytes can be determined by referring to the stored information that uniquely associates each spatial barcode with an array feature location. In this manner, specific capture probes and captured analytes are associated with specific locations in the array of features. Each array feature location represents a position relative to a coordinate reference point (e.g., an array location, a fiducial marker) for the array. Accordingly, each feature location has an "address" or location in the coordinate space of the array.

Some exemplary spatial analysis workflows are described in the Exemplary Embodiments section of WO 2020/176788 and/or U.S. Patent Application Publication No. 2020/0277663. See, for example, the Exemplary embodiment starting with "In some non-limiting examples of the workflows described herein, the sample can be immersed . . . " of WO 2020/176788 and/or U.S. Patent Application Publication No. 2020/0277663. See also, e.g., the Visium Spatial Gene Expression Reagent Kits User Guide (e.g., Rev C, dated June 2020), and/or the Visium Spatial Tissue Optimization Reagent Kits User Guide (e.g., Rev C, dated July 2020).

In some embodiments, spatial analysis can be performed using dedicated hardware and/or software, such as any of the systems described in Sections (II)(e)(ii) and/or (V) of WO 2020/176788 and/or U.S. Patent Application Publication No. 2020/0277663, or any of one or more of the devices or methods described in Sections Control Slide for Imaging, Methods of Using Control Slides and Substrates for, Systems of Using Control Slides and Substrates for Imaging, and/or Sample and Array Alignment Devices and Methods, Informational labels of WO 2020/123320.

Suitable systems for performing spatial analysis can include components such as a chamber (e.g., a flow cell or sealable, fluid-tight chamber) for containing a biological sample. The biological sample can be mounted for example, in a biological sample holder. One or more fluid chambers can be connected to the chamber and/or the sample holder via fluid conduits, and fluids can be delivered into the chamber and/or sample holder via fluidic pumps, vacuum sources, or other devices coupled to the fluid conduits that create a pressure gradient to drive fluid flow. One or more valves can also be connected to fluid conduits to regulate the flow of reagents from reservoirs to the chamber and/or sample holder.

The systems can optionally include a control unit that includes one or more electronic processors, an input interface, an output interface (such as a display), and a storage unit (e.g., a solid state storage medium such as, but not limited to, a magnetic, optical, or other solid state, persistent, writeable and/or re-writeable storage medium). The control unit can optionally be connected to one or more remote devices via a network. The control unit (and components thereof) can generally perform any of the steps and functions described herein. Where the system is connected to a remote device, the remote device (or devices) can perform any of the steps or features described herein. The systems can optionally include one or more detectors (e.g., CCD, CMOS) used to capture images. The systems can also optionally include one or more light sources (e.g., LED-based, diode-based, lasers) for illuminating a sample, a substrate with features, analytes from a biological sample captured on a substrate, and various control and calibration media.

The systems can optionally include software instructions encoded and/or implemented in one or more of tangible storage media and hardware components such as application specific integrated circuits. The software instructions, when executed by a control unit (and in particular, an electronic processor) or an integrated circuit, can cause the control unit, integrated circuit, or other component executing the software instructions to perform any of the method steps or functions described herein.

In some cases, the systems described herein can detect (e.g., register an image) the biological sample on the array. Exemplary methods to detect the biological sample on an array are described in PCT Application No. 2020/061064 and/or U.S. patent application Ser. No. 16/951,854.

Prior to transferring analytes from the biological sample to the array of features on the substrate, the biological sample can be aligned with the array. Alignment of a biological sample and an array of features including capture probes can facilitate spatial analysis, which can be used to detect differences in analyte presence and/or level within different positions in the biological sample, for example, to generate a three-dimensional map of the analyte presence and/or level. Exemplary methods to generate a two-and/or three-dimensional map of the analyte presence and/or level are described in PCT Application No. 2020/053655 and spatial analysis methods are generally described in WO 2020/061108 and/or U.S. patent application Ser. No. 16/951, 864.

In some cases, a map of analyte presence and/or level can be aligned to an image of a biological sample using one or more fiducial markers, e.g., objects placed in the field of view of an imaging system which appear in the image produced, as described in the Substrate Attributes Section, Control Slide for Imaging Section of WO 2020/123320, PCT Application No. 2020/061066, and/or U.S. patent application Ser. No. 16/951,843. Fiducial markers can be used as a point of reference or measurement scale for alignment (e.g., to align a sample and an array, to align two substrates, to determine a location of a sample or array on a substrate relative to a fiducial marker) and/or for quantitative measurements of sizes and/or distances.

Methods and Compositions Including Antigen-Binding Molecule Libraries and Uses Thereof The present disclosure features methods of generating an antigen-binding molecule/nucleic acid conjugate library, methods of displaying (e.g., ribosomal display, mRNA/cDNA display) antigen-binding molecules/nucleic acid libraries, methods of identifying antigen-binding molecules that selectively bind to antigens in a test biological sample and determining the location of the antigen in the test biological sample, and compositions and kits thereof.

Therapeutic antibodies are an essential class of drugs which are widely used in the treatment of cancer, autoimmunity, and inflammatory diseases, and/or for drug delivery to target antigens. Conventional antibodies (e.g., IgG) are large in size (e.g., about 150 kDa) and includes two heavy and two light chains. Additionally, in conventional antibody screening a target of interest generally needs to be known. However, since few targets are known, most antibody screens repeatedly test against the same existing drug targets and novel targets are seldom explored. Conventional antibody screening generally occurs in vitro on selected cell lines and may not recapitulate the in vivo context, where the target cells/peptides are embedded within a complex tissue environment and often the screening process is time intensive and offers little room for customization (e.g. by using patient biopsies).

Smaller, single-chain, antigen-binding molecules (e.g., about 15 kDa) can be attractive alternatives to conventional antibodies. In some examples, single-chain antibodies include scFv single-chain antibodies. In some examples, single-chain antibodies include VHH antibodies (e.g., nanobodies). These single-chain antibodies are generally more stable, easier to generate large libraries, and easier to screen than conventional antibodies. For example, single-chain antibody libraries can be generated with a diversity (e.g., different single-chain antibodies) of about $1\times10^6$ to about $1\times10^{15}$, about $1\times10^7$ to about $1\times10^{14}$, about $1\times10^8$ to about $1\times10^{13}$, or about $1\times10^9$ to about $1\times10^{12}$. The methods described herein can also identify novel targets in the context of a complex tissue environment in a rapid manner and can be screened against healthy and/or diseased tissues.

Additionally, the single-chain antibodies can be screened via various display techniques. In some examples, the display technique is ribosomal display. In some examples, the display technique is mRNA/cDNA display. In some examples, the display technique is yeast display. These screening techniques can also be performed in combination with a spatial array (e.g., an array including a plurality of capture probes, where a capture probe includes a spatial barcode and a capture domain). For example, single-chain antibodies can be displayed in an in vitro system, screened against a healthy biological sample (e.g., healthy tissue section), and the non-binding antibodies can be collected (e.g., washed off) the biological sample and screened against a diseased biological sample (e.g., a tumor sample). Non-binding antibodies can be removed from the diseased biological sample (e.g., washed off) and the remaining single-chain antibodies bound to an antigen present in the diseased biological sample can be captured on a spatial array as described herein and identified.

Thus, the present disclosure features methods of generating an antigen-binding molecule/nucleic acid conjugate library, where an antigen-binding molecule/nucleic acid conjugate of the antigen-binding molecule/nucleic acid conjugate library includes an antigen-binding molecule linked to a nucleic acid encoding the antigen-binding molecule, the method including: a) providing a plurality of mRNAs, wherein an mRNA of the plurality of mRNAs includes in a 5' to 3' direction: (i) an analyte capture sequence which binds a capture domain of a capture probe, or a reverse complement thereof, (ii) a sequence encoding the antigen-binding molecule, (iii) a primer binding sequence, (iv) a universal domain attached to a donor oligonucleotide, where the donor oligonucleotide includes a linker having a nucleotide sequence and a protein translation inhibitor; b) in vitro translating the plurality of mRNAs, thereby generating the antigen-binding molecule/nucleic acid conjugate library antigen-binding molecule mRNA.

The present disclosure also features methods of screening antigen-binding molecule/nucleic acid conjugates in a biological sample (e.g., a healthy biological sample, a diseased biological sample). Thus, provided herein are methods of identifying an antigen-binding molecule that selectively binds to an antigen in a biological sample, the method including: a) contacting the biological sample with members of an antigen-binding molecule/nucleic acid conjugate library, wherein an antigen-binding molecule/nucleic acid conjugate of the library includes an antigen-binding molecule linked to a nucleic acid encoding the antigen-binding molecule, and where the nucleic acid includes a cDNA/RNA duplex, wherein the RNA strand of the duplex includes: i) a sequence complementary to the analyte capture sequence which binds (e.g., hybridizes) a capture domain of a capture probe, ii) a sequence encoding an antigen-binding molecule, iii) a primer binding sequence, and iv) a universal domain attached to a donor oligonucleotide, where the donor oligonucleotide includes a linker having a nucleotide sequence and a protein translation inhibitor, b) removing one or more unbound antigen-binding molecule/nucleic acid conjugates from the biological sample c) contacting a biological sample with an array including a plurality of capture probes, where a capture probe of the plurality includes (i) a spatial barcode and (ii) a capture domain; and d) capturing one or more cDNAs of the antigen-binding molecule/nucleic acid conjugates onto one or more capture probes of the array, where an analyte capture sequence of the cDNA binds to the capture domain of the capture probe.

Single-Chain Antigen-Binding Molecule

As used herein a "single-chain antigen-binding molecule" includes single-chain antibodies, single-chain antigen-binding fragments, and single-chain antigen-binding fusion proteins. In some embodiments, a single-chain antigen-binding molecule is a nanobody. In some embodiments, a single-chain antigen-binding molecule is a single-chain variable fragment (scFv) fusion protein.

A "nanobody" (Nb), as used herein, can refer to a single domain antibody. Nanobodies can include VHH antibodies (single variable domain on a heavy chain antibody) and can be derived from naturally occurring heavy chain antibody. Nanobodies can be derived from heavy chain only antibodies as found in camelids (Hamers-Casterman et al., Naturally occurring antibodies devoid of light chains, *Nature,* 363, 446-448 (1993)). "Camelids" include old world camelids (e.g., *Camelus bactrianus, Camelus dromedarius*) and new world camelids, such as llamas (e.g., *Lama paccos, Lama glama, Lama guanicoe,* and *Lama vicugna*). The single variable domain heavy chain antibody can be referred to herein as a "nanobody" or a VHH antibody. It is noted that the term "nanobody," as used herein in its broadest sense, is not limited to a specific biological source or to a specific method of preparation. For example, the nanobodies hereof, and their associated nucleotide sequences, can generally be obtained: (1) by isolating the VHH domain of a naturally occurring heavy chain antibody; (2) by expression of a nucleotide sequence encoding a naturally occurring VHH domain; (3) by "humanization" of a naturally occurring VHH domain or by expression of a nucleic acid encoding such a humanized VHH domain; (4) by "camelization" of a naturally occurring VH domain from any animal species, and, in particular, from a mammalian species, such as from a human being, or by expression of a nucleic acid encoding such a camelized VH domain; (5) by "camelization" of a "domain antibody" or "Dab" as described in the art, or by expression of a nucleic acid encoding such a camelized VH domain; (6) by using synthetic or semi-synthetic techniques for preparing proteins, polypeptides or other amino acid sequences known per se; (7) by preparing a nucleic acid encoding a nanobody using techniques for nucleic acid synthesis known per se, followed by expression of the nucleic acid thus obtained; and/or (8) by any combination of one or more of the foregoing.

The small size and unique biophysical properties of nanobodies provide alternatives to conventional antibody fragments since they can recognize uncommon or hidden epitopes and can bind into cavities or active sites of protein targets.

Single-chain variable fragment antibodies (scFvs) are single-chain antigen-binding molecules (e.g., single-chain antigen-binding fusion proteins) that can be used in any of the methods described herein. Generally, an scFv is a fusion protein of the variable region of the heavy ($V_H$) and the light chain ($V_L$) of immunoglobulins, thus lacking the $F_C$ domain, and are usually connected with a short peptide linker of about 10 to about 25 amino acids. Generally, the linker can include a series of variants generated to optimize binding affinity and stability. Variations of scFv molecules have been engineered including paired scFvs that bind to one another through complementary regions to form bivalent molecules (diabodies), complementary scFvs themselves produced as a single chain (tandem scFvs or tascFvs), and bispecific tandem scFvs (bis-scFvs), as well as others.

Thus, in some embodiments, the antigen-binding molecule includes a single-chain antigen-binding molecule. In some embodiments, the single-chain antigen binding molecule includes a single-chain variable fragment (scFv). In some embodiments, the single-chain antigen binding molecule includes a nanobody. It will be appreciated by one skilled in the art that additional single-chain antigen molecules can also be used with any of the methods described herein.

Antigen-Binding Molecule Display Methods

Various display methods suitable for the methods disclosed herein include, but are not limited to, yeast display, phage display, ribosome display, and mRNA/cDNA display. Generally, there are advantages and disadvantages to each to these various display methods. For example, yeast and phage display are generally more commonly used, and include advantages such as full-length IgGs and post-translation modifications (e.g., glycosylation in yeast); however, library generation in these display methods tend to be more onerous. For example, yeast and phage display methods described herein, require the synthesized DNA libraries to be first cloned into a yeast or phage vector. Subsequently, the yeast or phage is lysed in order to release the cDNA library (e.g., plasmid including the DNA library). In some embodiments, the yeast or phage library is lysed at about the same time as the biological sample (e.g., tissue section) is permeabilized (see, e.g., Fiskin, E. et al., Single-cell multimodal profiling of proteins and chromatin accessibility using PHAGE-ATAC, bioRxiv preprint doi: https://doi.org/10.1101/2020.10.01.322420, (2021)). Additional methods such as ribosome display, discussed below, and mRNA/cDNA display include advantages such as rapidly generating large libraries and tethering translated proteins to their own mRNA.

mRNA/cDNA or mRNA display is a robust in vitro display technology that converts an unstable mRNA-protein fusion (mRNA display) to a stable mRNA/cDNA-protein fusion (e.g., cDNA display) where the cDNA is covalently linked to its encoded protein using a puromycin linker (Ueno and Nemoto, cDNA display: rapid stabilization of mRNA display, *Methods Mol Biol.,* 805:113-35 (2012), which is incorporated herein by reference in its entirety). Synthesis of an mRNA display library begins with synthesis of a DNA library. A DNA library for any protein or small peptide of interest (e.g., an antigen-binding molecule) can be synthesized by various methods, including solid-phase synthesis followed by PCR amplification. As an example, DNA libraries encoding sequences for nanobodies and associated display methods are described in Doshi, R., et al., In vitro nanobody discovery for integral membrane protein targets. *Sci Rep,* 4, 6760 (2014), which is incorporated herein by reference in its entirety. Generally, members of the DNA library have a transcription site (e.g., a T7 RNA polymerase transcription site, a T3 RNA polymerase transcription site, an SP6 RNA polymerase transcription site) and a ribosomal binding site at their 5' end. The promoter (e.g., a RNA promoter such as T7 RNA promoter, SP6 RNA promoter, T3 RNA promoter) allows large-scale in vitro transcription to transcribe the DNA library into an mRNA nucleic acid library with a polymerase (e.g., a T7 RNA polymerase, a T3 RNA polymerase, a SP6 RNA polymerase, etc.). Also, the ribosomal binding site in the 5'-untranslated region (5' UTR) can be designed according to the in vitro translation system to be used (e.g., prokaryotic or eukaryotic).

As such, mRNA display is a method for in vitro protein/peptide evolution to generate molecules that can bind to a desired target. For example, mRNA display can be used to generate a large library of antigen-binding molecules and screened for potential against healthy (e.g., control) and or diseased (e.g., tumorous) biological samples. The mRNA display method results in translated peptides or proteins that are associated with their mRNA via a puromycin linkage. Different methods of screening can be performed, including testing binding of the conjugate(s) to an immobilized target in a selection step, such as affinity chromatography. The mRNA-protein conjugates that bind can be reverse transcribed to cDNA and their sequence amplified via a polymerase chain reaction, resulting in a nucleotide sequence that encodes a peptide with high affinity for the molecule of interest.

Generally, puromycin is used in mRNA display to inhibit translation that results in an mRNA-protein (e.g., antigen-binding molecule/nucleic acid) conjugate. Puromycin is an analogue of the 3' end of a tyrosyl-transfer RNA (tRNA) where a portion of its structure mimics an adenosine molecule and another portion mimics a tyrosine molecule. As compared to the cleavable ester bond found in tyrosyl-tRNA, puromycin has a non-hydrolysable amide bond, and as a result, puromycin interferes (e.g., halts) translation and the conjugate molecule is released from the ribosome.

The present disclosure features display methods including yeast display, phage display, ribosomal display, and/or mRNA/cDNA display with single-chain antigen binding molecules. In some embodiments, the display construct includes an analyte capture sequence capable of binding a capture domain of a capture probe on a substrate. In embodiments utilizing mRNA/cDNA display, the cDNA of the mRNA/cDNA construct includes an analyte capture sequence capable of binding a capture domain of a capture probe on a substrate. In such embodiments, a biological sample (e.g., a tissue section) can be contacted with an array including a plurality of capture probes, where a capture probe of the plurality of capture probes includes: i) a spatial barcode and ii) a capture domain.

In some embodiments, after translation of the mRNA, the mRNA of the mRNA/protein complex is directly captured (e.g., without cDNA synthesis). Provided herein are methods of generating an antigen-binding molecule/nucleic acid conjugate library, where an antigen-binding molecule/nucleic acid conjugate of the antigen-binding molecule/nucleic acid conjugate library includes an antigen-binding molecule linked to a nucleic acid encoding the antigen-binding molecule, the method including: a) providing a plurality of in vitro transcribed mRNAs, wherein an mRNA of the plurality of in vitro transcribed mRNAs comprises in a 5' to 3' direction: (i) an analyte capture sequence that hybridizes to a capture domain of a capture probe, (ii) a sequence encoding the antigen-binding molecule, (iii) a primer binding sequence, (iv) a universal domain attached to a donor oligonucleotide, wherein the donor oligonucleotide comprises a linker having a nucleotide sequence and a protein translation inhibitor; and b) in vitro translating the plurality of in vitro transcribed mRNAs, thereby generating the antigen-binding molecule/nucleic acid conjugate library antigen-binding molecule mRNA.

The methods described herein allow identification of an antigen-binding molecule that selectively binds to an antigen in a biological sample (e.g., a tissue section) in its in vivo spatial context, whereas typical screening methods are performed for known targets and in in vitro or lysate samples.

mRNA display also generally includes the use of oligonucleotides or other linkers to provide flexibility and proper length for the puromycin to enter the A site of the ribosome. Generally, the linker between the 3' end of an mRNA and the puromycin has to be flexible and long enough to allow the puromycin to enter the A site upon translation of the last codon. In some embodiments, the linker includes a poly (A) sequence. In some embodiments, the linker includes a unique sequence. In some embodiments, the linker is at least 10 nucleotides, at least 15 nucleotides, at least 20 nucleotides, at least 25 nucleotides, at least 30 nucleotides, or at least 35 nucleotides.

As discussed above mRNA display can include the use of linkers, such as oligonucleotide linkers, conjugated to a protein translation inhibitor molecule, such as puromycin. In some embodiments, the methods described herein include a prior step of attaching the donor oligonucleotide to the universal domain via ligation. Various methods of attaching the donor oligonucleotide to the universal domain are known to a person skilled in the art, including for example, splint ligation, Y-ligation, ultraviolet light (UV) crosslinking, and the transcription-translation couple with association of puromycin linker (TRAP) system as described in Huang, Y., et al., RNA Display Methods for the Discovery of Bioactive Macrocycles, *Chem. Rev.,* 119, 10360-10391 (2019), the contents of which are incorporated herein by reference in its entirety.

In some embodiments, the ligation includes ligation via a splint oligonucleotide. In some embodiments, the splint oligonucleotide includes a sequence substantially complementary to the linker of the donor oligonucleotide, or a portion thereof. In some embodiments, the splint oligonucleotide includes a sequence substantially complementary to the universal domain, or a portion thereof. In some embodiments, the ligation includes ligation with a splint oligonucleotide. In some embodiments, the splint oligonucleotide includes a sequence substantially complementary to the linker of the donor oligonucleotide, or a portion thereof and includes a sequence substantially complementary to the universal domain, or a portion thereof.

In some embodiments, the ligating includes Y-ligation. In some embodiments, the linker of the donor oligonucleotide includes a sequence substantially complementary to the universal domain, or a portion thereof. In some embodiments, the method includes ligating the 5' end of the donor oligonucleotide to the 3' end of the universal domain.

In some embodiments, the ligating includes the use of a ligase. In some embodiments, the ligase includes T4 DNA ligase, T4 RNA ligase, Tth DNA ligase, Taq DNA ligase, *Thermococcus* sp. DNA ligase, Ampligase™, PBCV-1 DNA Ligase, Splint ligase, and a Chlorella virus DNA Ligase, and combinations thereof.

In some embodiments, ligating includes ultra-violet (UV) light cross-linking. In some embodiments, the linker of the donor oligonucleotide includes a sequence that is substantially complementary to the universal domain, or a portion thereof. In some embodiments, the 5' end of the linker includes a UV light photoreactive moiety. In some embodiments, the UV light photoreactive moiety includes psoralen.

In some embodiments, the linker of the donor oligonucleotide includes a sequence that is substantially complementary to the universal domain, or a portion thereof. In some embodiments, the protein translation inhibitor is non-covalently attached to the mRNA.

In some embodiments, the protein translation inhibitor is a protein translation inhibitor molecule. In some embodiments, the protein translation inhibitor molecule is covalently attached to the mRNA. In some embodiments, the protein translation inhibitor molecule is puromycin.

Additional methods of antigen-binding molecule display are known in the art including ribosomal display (see e.g., He and Taussing, Ribosome display: Cell-free protein display technology, *Briefings in Functional Genomics and Proteomics,* 204-212 (2002), the contents of which are incorporated herein by reference in its entirety). Generally, ribosomal display is a cell-free system for the in vitro selection of proteins and peptides from nucleic acid libraries. A fundamental feature of ribosomal display includes the principle of coupling individual translated proteins to their corresponding mRNA, through the formation of stable protein-ribosome-mRNA (PRM) complexes (e.g., antigen-binding molecule/nucleic acid conjugates). Coupling the protein (e.g., antigen-binding molecule) to its own mRNA permits the simultaneous isolation of a functional protein (e.g., antigen-binding molecule) through affinity for a ligand, such as an antigen, together with the encoding mRNA. The mRNA can then be converted (e.g., reverse transcribed) and amplified as DNA for further manipulation, including repeated cycles or protein expression.

Ribosomal display can display large antigen-binding molecule/nucleic acid libraries without the restriction of bacterial transformation. Another benefit of ribosomal display is that it can allow for generating toxic, proteolytically sensitive, and unstable proteins, and allows the incorporation of modified amino acids at defined positions. In combination with polymerase chain reaction (PCR)-based methods, mutations can be introduced efficiently into the selected DNA pool in subsequent cycles, leading to continuous DNA diversification and antigen-binding molecule selection (e.g., in vitro protein evolution). Both prokaryotic and eukaryotic ribosome display systems have been developed and each has its own distinctive features.

Generally, ribosomal display strategies include either (i) addition of antibiotics such as rifampicin and chloramphenicol (for prokaryotic ribosomes) or cycloheximide (for eukaryotic ribosomes) to halt translation at random times or (ii) deletion of the stop codon, typically recognized by release factors which trigger detachment of the polypeptide (e.g., antigen-binding molecule), to stall the ribosome at the end of the mRNA.

Thus, in some embodiments, the protein translation inhibitor does not include a stop codon. For example, the lack of a stop codon in the mRNA which includes a sequence encoding an antigen-binding molecule allows the antigen-binding molecule to be translated, but does not allow antigen-binding molecule to be released from the ribosome. The resulting complex is an antigen-binding molecule complexed with its own mRNA (e.g., antigen-binding molecule/nucleic acid complex) that can then be assayed (e.g., screened) for binding an antigen.

As described above in the various display methods (e.g., ribosome display, mRNA display) a complementary cDNA can be generated that encodes a protein or peptide (e.g., an antigen binding molecule of interest). Thus, in some embodiments, the methods described herein include generating a cDNA complementary to the mRNA (e.g., the nucleic acid of the antigen-binding molecule/nucleic acid conjugate) to produce a double stranded DNA/RNA duplex. In some embodiments, generating the cDNA includes reverse transcribing the mRNA. In some embodiments, reverse transcription includes the use of a primer that hybridizes to a universal domain of the mRNA.

Figures 2A, 2B, 2C:
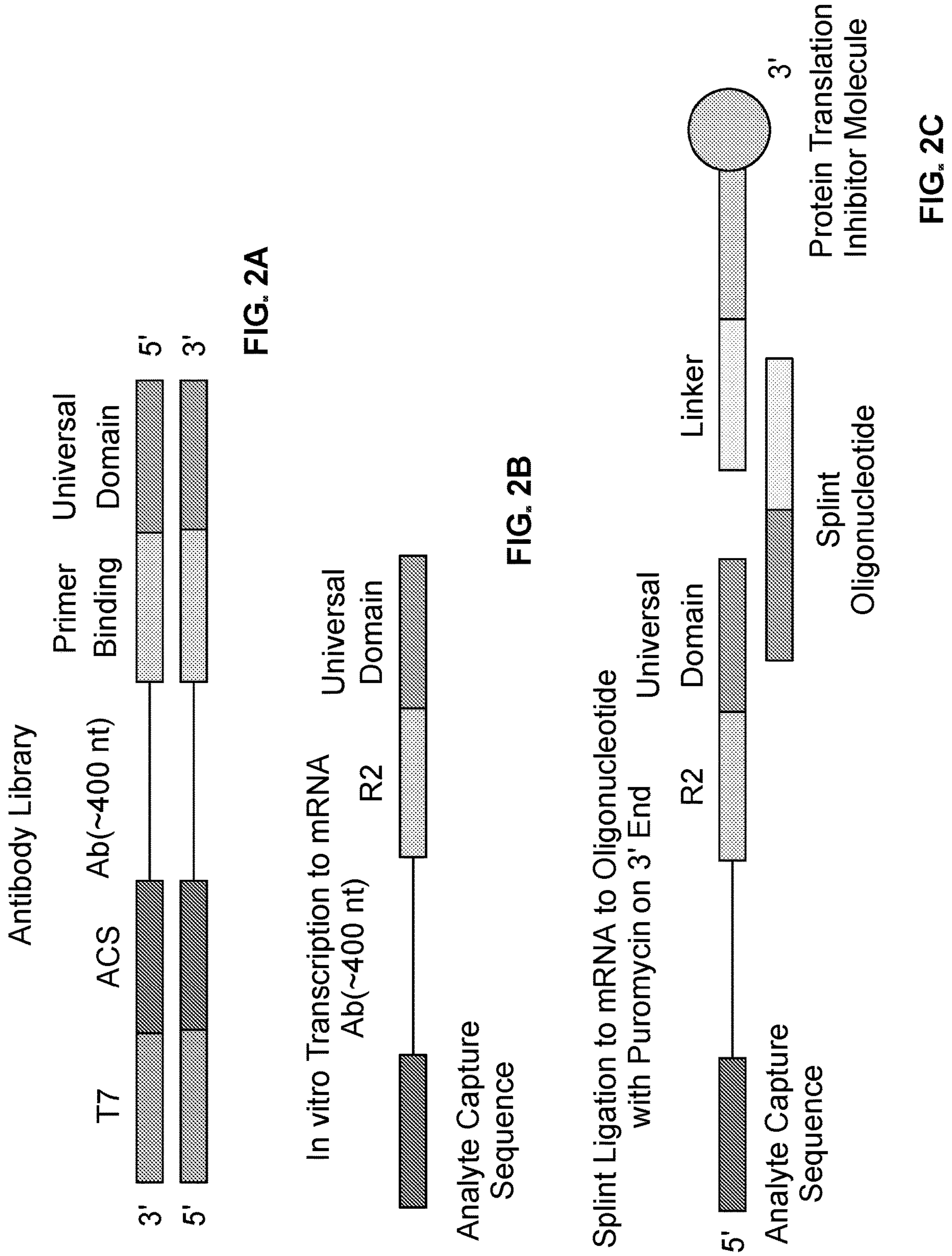
FIGS. 2A-E show an exemplary single-chain antibody nucleic acid library (FIG. 2A) and an exemplary method of generating a display library via in vitro transcription of the single-chain antibody nucleic acid library (FIGS. 2B-E).
Figure 2D:
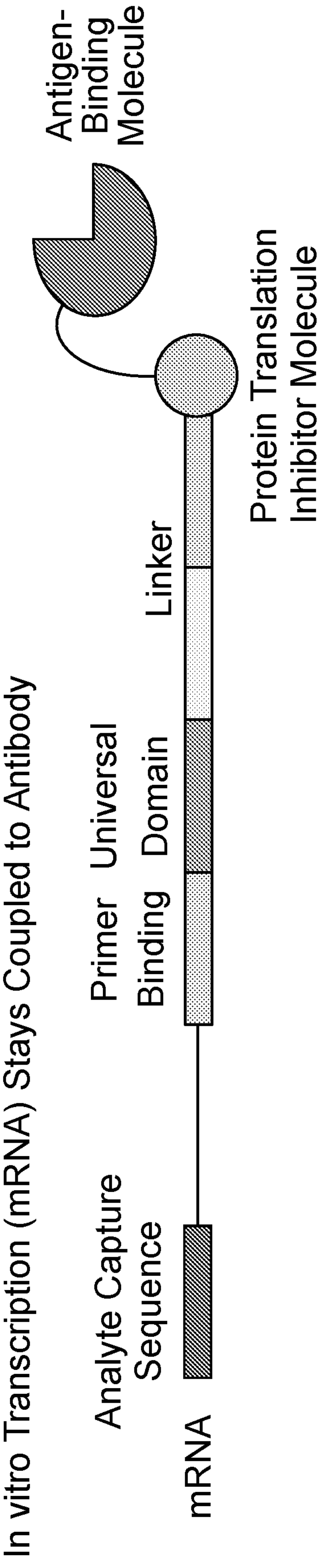
Figure 2E:
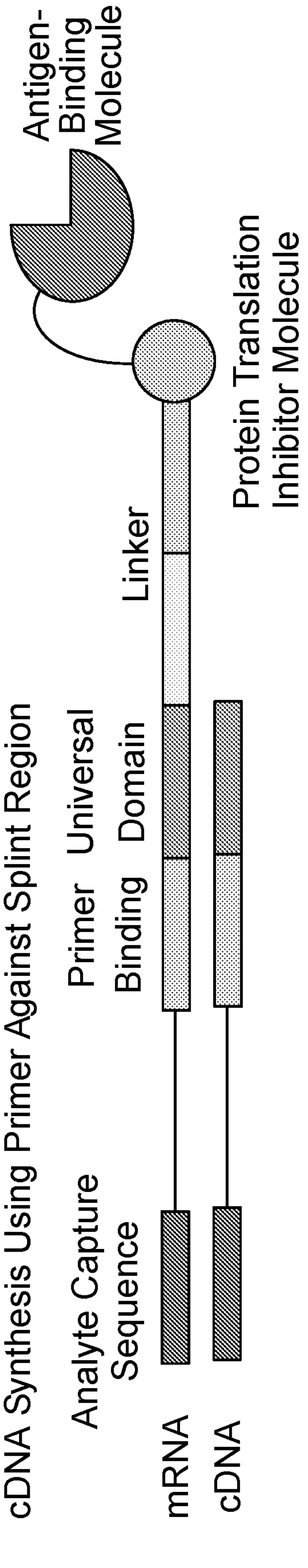

FIGS. 2A-E show an exemplary single-chain antibody nucleic acid library (FIG. 2A) and an exemplary method of generating a display library via in vitro transcription of the single-chain antibody nucleic acid library (FIGS. 2B-E). In some embodiments, a member of the nucleic acid library includes in a 5' to 3' direction a primer binding sequence, an analyte capture sequence (ACS) (e.g., an analyte capture sequence that interacts with a capture domain) or a reverse complement thereof, a sequence encoding a single-chain antibody or antigen-binding fragment thereof, a second primer binding site and a universal domain (FIG. 2A). In some embodiments, a member of the nucleic acid library includes an analyte capture sequence (e.g., an analyte capture sequence that interacts with a capture domain) or a reverse complement thereof, a sequence encoding a single-chain antibody or antigen-binding fragment thereof, a primer binding site, and a universal domain. In some embodiments, a member of the nucleic acid library includes a promoter sequence, an analyte capture sequence (e.g., an analyte capture sequence that interacts with a capture domain) or a reverse complement thereof, a sequence encoding a single-chain antibody or antigen-binding fragment thereof, a primer binding site, and a universal domain. The promoter sequence can be a promoter suitable for in vitro transcription. Exemplary promoter sequences for in vitro transcription include, but are not limited to, an RNA polymerase promoter sequence, e.g., a T7 promoter sequence, SP6 promoter sequence, T3 promoter sequence. While FIG. 2A shows a particular 5' to 3' orientation of the domains, it is appreciated by those skilled in the art that the orientation of the domains can be rearranged in such a manner to capture the mRNA directly after in vitro transcription as described above. Additionally, FIG. 2A shows a double-stranded nucleic acid library, however, it is understood by those skilled in the art that the nucleic acid library can be a single-stranded nucleic acid library. Thus, in some embodiments, the nucleic acid library is double-stranded. In some embodiments, the nucleic acid library is single-stranded. In some embodiments, the nucleic acid library (e.g., any of the nucleic acid libraries described herein) are transcribed to mRNA. For example. FIG. 2B shows the resulting mRNA after in vitro transcription of a member of the nucleic acid library shown in FIG. 2A. In some embodiments, a protein translation inhibitor molecule and a linker are attached to the 3' end of the transcribed mRNA. FIG. 2C shows an exemplary method of the mRNA of FIG. 2B ligated to a molecule including a linker and a protein translation inhibitor molecule. In some embodiments, the ligation includes a splint oligonucleotide, however, other methods as described herein can also be used. FIG. 2C shows an exemplary method where the ligation is facilitated by a splint oligonucleotide, although other methods of attaching the mRNA and the molecule including the linker and protein translation inhibitor molecule are known in the art. For example, other methods of attaching the mRNA and the molecule including the linker and the protein translation inhibitor molecule including Y-ligation or the TRAP system as described herein. FIG. 2D shows the resulting antigen-binding molecule/nucleic acid conjugate, however, other methods and additional orientations of the domains shown in FIG. 2D are also contemplated by the present disclosure. FIG. 2E shows a complementary cDNA synthesized to the nucleic acid portion of the antigen-binding/nucleic acid conjugate. In some embodiments, a cDNA is synthesized complementary to the mRNA sequence of the antigen-binding/nucleic acid conjugate. In some embodiments, a cDNA is not synthesized to the mRNA sequence of the antigen-binding/nucleic acid conjugate. For example, the mRNA (e.g., the nucleic acid sequence encoding the mRNA) can be designed in such a way and with the domains oriented in such a way as described herein to enable direct capture of the nucleic acid of the antigen-binding/nucleic acid conjugate without the synthesis of cDNA as shown in FIG. 2E.

Screening

The display methods described herein can be further used in various screening assays. For example, antigen-binding molecule/nucleic acid conjugates produced by any of the display methods described herein can be screened against a particular target of interest. Additionally, antigen-binding molecule/nucleic acid conjugates can be screened against diseased biological samples (e.g., tumorous tissue) to identify novel antigen-binding molecules that bind targets expressed and/or overexpressed in diseased cells or tissues that may be valuable in future therapeutic applications. For example, antigen-binding molecules can be first positively screened on healthy biological samples (e.g., control biological samples) to potentially identify any antigen-binding molecules with an affinity for a target present in a healthy biological sample. Further, non-binding antigen-binding molecules can be removed from the healthy biological sample and collected (e.g., negative selection) and assayed for binding to a diseased biological sample (e.g., positive selection on a tumorous biological sample). Additionally, while various display methods are typically performed on lysates for a particular target, methods of spatially capturing antigen-binding molecules (e.g., nucleic acids (e.g., cDNA) encoding antigen-binding molecules) from a biological sample (e.g., any of the biological samples described herein) are still needed. For example, screening is generally performed in vitro on selected cell lines and/or lysates and may not reflect the in vivo context. However, in contrast, screening performed on a biological sample (e.g., a tissue section) where the antigens, including known and unknown antigens, are embedded within a complex tissue environment can provide in vivo context lacking in cell lines and/or lysate samples.

Provided herein are methods of identifying an antigen-binding molecule that selectively binds to an antigen in a biological sample, the method including: a) providing an array including a plurality of capture probes, where a capture probe of the plurality includes (i) a spatial barcode and (ii) a capture domain; b) contacting the biological sample with members of an antigen-binding molecule/nucleic acid conjugate library, where an antigen-binding molecule/nucleic acid conjugate of the library includes an antigen-binding molecule linked to a nucleic acid encoding the antigen-binding molecule, and where the nucleic acid includes a cDNA/RNA duplex, where the RNA strand of the duplex comprises: i) a sequence complementary to the analyte capture sequence which binds a capture domain of a capture probe, ii) a sequence encoding an antigen-binding molecule, iii) a primer binding sequence, and iv) a universal domain attached to a donor oligonucleotide, where the donor oligonucleotide includes a linker having a nucleotide sequence and a protein translation inhibitor, c) removing one or more unbound antigen-binding molecule/nucleic acid conjugates from the biological sample; and d) capturing one or more cDNAs of the antigen-binding molecule/nucleic acid conjugates onto one or more capture probes of the array, where an analyte capture sequence of the cDNA binds to the capture domain of the capture probe.

In some embodiments, the method includes determining (i) the sequence of the spatial barcode or a complement thereof, and (ii) all or a portion of the sequence of the cDNA, or a complement thereof. In some embodiments, the method includes using the determined sequences of (i) the sequence of the spatial barcode or a complement thereof and (ii) all or a portion of the sequence of the cDNA or a complement thereof to identify an antigen-binding molecule that selectively binds to an antigen in the biological sample and determine the location of the antigen in the biological sample. In some embodiments, the determining includes sequencing. In some embodiments, step (c) is performed before (a), after (a), or after (b).

In some embodiments, the members of the antigen-binding molecule/nucleic acid conjugate library were selected by a prior step of contacting a control biological sample with the antigen-binding molecule/nucleic acid conjugate library, and selecting members of the library that did not bind to the control biological sample.

In some embodiments, the biological sample is disposed on the spatial array including the plurality of capture probes. For example, the biological sample (e.g., a tissue section) can be placed directly onto the spatial array, where the spatial array includes the plurality of capture probes. In some embodiments, the biological sample is disposed on a substrate (e.g., a separate substrate from the spatial array). For example, a biological sample can be disposed on a second substrate different from the substrate including the spatial array including the plurality of capture probes. In some embodiments, the method includes aligning the substrate (e.g., the substrate with a biological sample) with the spatial array, such that at least a portion of the biological sample is aligned with at least a portion of the spatial array. In such embodiments, the biological sample and the spatial array are in a “sandwich” configuration where either the spatial array or the biological sample are on the bottom or top position of the sandwich configuration.

In some embodiments, the control biological sample is a healthy biological sample. In some embodiments, the biological sample includes one or more healthy regions and one or more disease regions.

In some embodiments, biological sample is a diseased biological sample. In some embodiments, the diseased biological sample is a tumorous biological sample.

In some embodiments, the method includes releasing the cDNA from the antigen-binding molecule/nucleic acid conjugate prior to the capturing step. In some embodiments, the releasing includes an RNase. In some embodiments, the RNase is selected from the group consisting of RNase A, RNase C, RNase H, and RNase I.

In some embodiments, the releasing includes heat.

In some embodiments, the method includes permeabilizing the biological sample, the test biological sample (e.g., a diseased biological sample, a tumorous biological sample), or both.

In some embodiments, the method includes imaging the biological sample. In some embodiments, the method includes staining the biological sample (e.g., staining by any of the methods described herein). In some embodiments, the staining includes hematoxylin and eosin (H&E) staining.

In some embodiments, the array includes one or more features. In some embodiments, the one or more features includes a bead. In some embodiments, the capture probe includes any one or more of: a cleavage domain, a unique molecular identifier (UMI), one or more functional domain, and combinations thereof.

In some embodiments, the antigen-binding molecule is a single-chain antigen-binding molecule. In some embodiments, the single-chain antigen-binding molecule includes a single-chain variable fragment (scFv). In some embodiments, the single-chain antigen-binding molecule includes a nanobody.

In some embodiments, the cDNA complementary to the nucleic acid of the antigen-binding molecule/nucleic acid conjugate is generated by reverse transcription.

The methods described herein can also be multiplexed, that is, capture of additional analytes or analyte derivatives in addition to capturing nucleic acid (e.g., cDNA) encoding an antigen-binding molecule on a spatial array. Thus, for example, additional nucleic acid present in the biological sample can also be captured on a spatial array and/or a nucleic acid derivative, such as for example, RNA templated ligation (RTL) probes that hybridize to a target nucleic acid and where one probe includes an analyte capture sequence that binds to a capture domain of a capture probe. Similarly, protein capture via an analyte capture agent can also be multiplexed with the methods described herein.

In some embodiments, the method includes capturing a nucleic acid analyte or derivative thereof from the biological sample, where the nucleic acid analyte binds to the capture domain of the capture probe.

In some embodiments, the nucleic acid analyte, or derivative thereof, includes DNA. In some embodiments, the nucleic acid analyte, or derivative thereof, includes RNA.

In some embodiments, the method includes (a) contacting a first probe and a second probe with the biological sample, wherein the first probe and the second probe each include one or more sequences that are substantially complementary to sequences of an analyte, and wherein the second probe includes a capture probe capture domain that is complementary to all or a portion of the capture domain; (b) hybridizing the first probe and the second probe to the analyte; (c) generating a ligation product by ligating the first probe and the second probe; (d) releasing the ligation product from the analyte; (e) hybridizing the ligation product to the capture domain; and (g) determining (i) all or part of the sequence of the ligation product bound to the capture domain, or a complement thereof, and (ii) all of the sequence of the spatial barcode, or a complement thereof, and using the determined sequences of (i) and (ii) to identify the location of the analyte in the biological sample.

In some embodiments, the methods include identifying the antigen bound by the antigen-binding molecule/nucleic acid complex. In some embodiments, the identifying includes mass spectrometry. In some embodiments, the identifying includes determining differential gene expression patterns between the control biological sample and the test biological sample. In some embodiments, the identifying includes determining differential gene expression patterns within the biological sample. For example, in instances where a biological sample includes healthy and diseased regions, differential gene expression patterns within those regions can be determined.

Figure 3A:
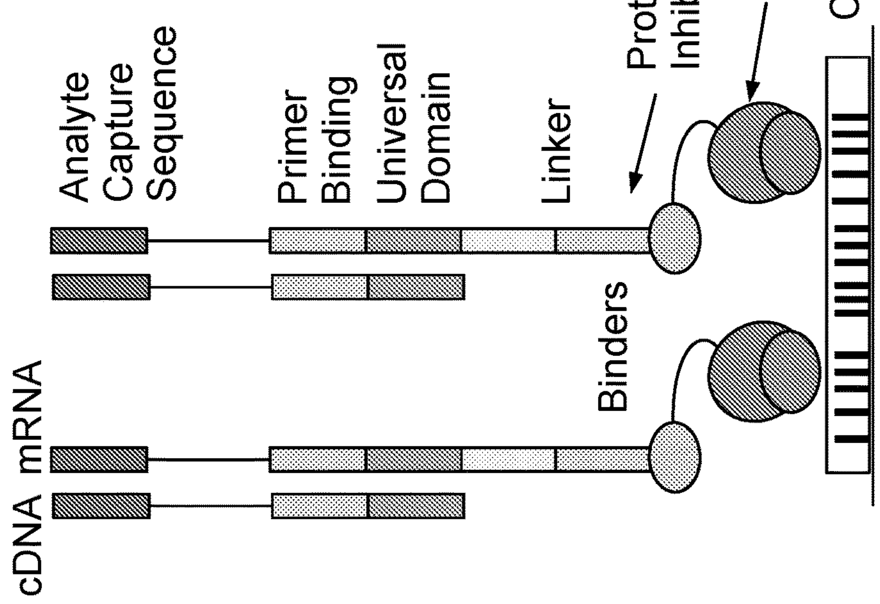
FIGS. 3A-B show exemplary antigen-binding molecule/nucleic acid conjugate members binding to an antigen in a biological sample (FIG. 3A) and removal of non-binding antigen-binding molecule/nucleic acid conjugate members (FIG. 3B).
Figure 3B:
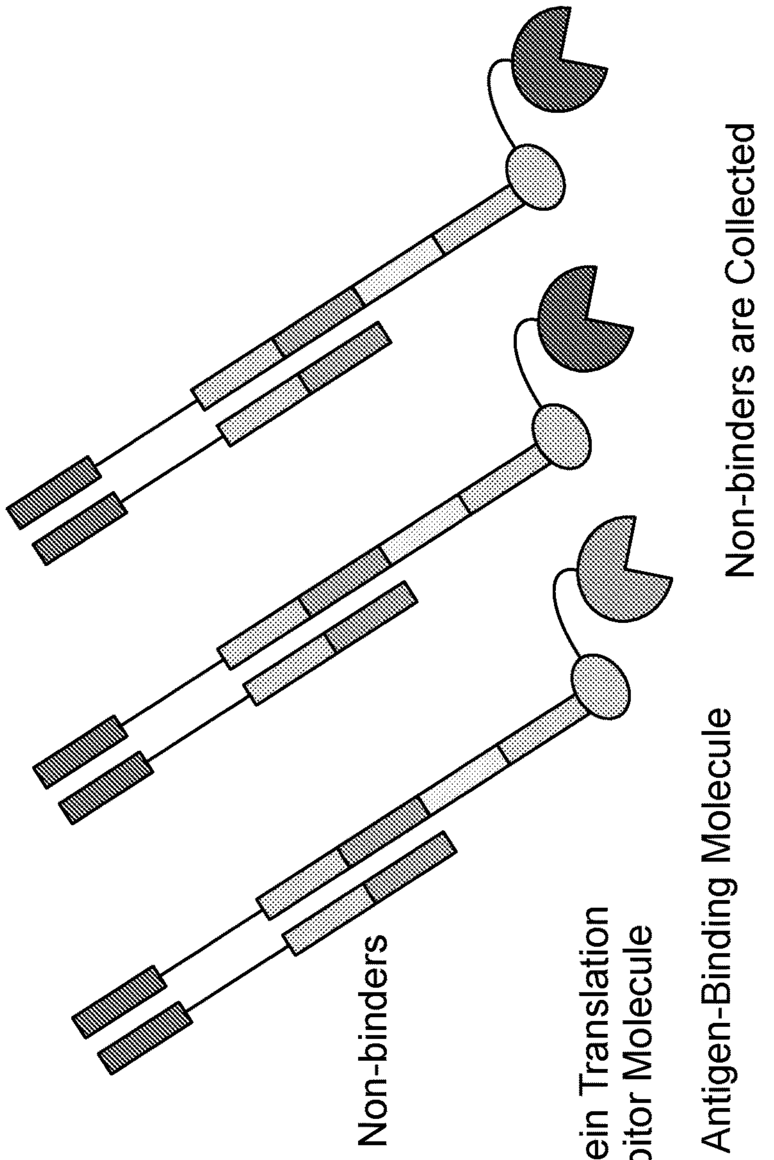

Antigen-binding molecule/nucleic acid conjugates generated as described herein can be screened against a control biological sample (e.g., a healthy biological sample, a non-diseased biological sample). In some embodiments, non-binding antigen-binding molecule/nucleic acid conjugates are removed from the control biological sample and collected for screening against a diseased (e.g., tumor) biological sample. FIGS. 3A-B show exemplary antigen-binding molecule/nucleic acid conjugate members generated, as described herein, binding to an antigen in a control biological sample (e.g., a healthy biological sample) (FIG. 3A). In some embodiments, the antigen-binding molecule/nucleic acid conjugate members bind to an antigen in a biological sample. In some embodiments, the antigen-binding molecule/nucleic acid conjugate members do not bind to an antigen in a biological sample (e.g., non-binding antigen-binding molecule/nucleic acid conjugates). While FIG. 3A shows an exemplary antigen-binding molecule/nucleic acid conjugate binding an antigen in a biological sample it is contemplated by the present disclosure that the antigen-binding molecule/nucleic acid conjugate, in some embodiments, does not include the cDNA as shown. In some embodiments, non-binding antigen-binding/nucleic acid conjugates are removed (e.g., washed) from the biological sample. In some embodiments, the non-binding antigen-binding/nucleic acid conjugates are collected (FIG. 3B).

Figure 4B:
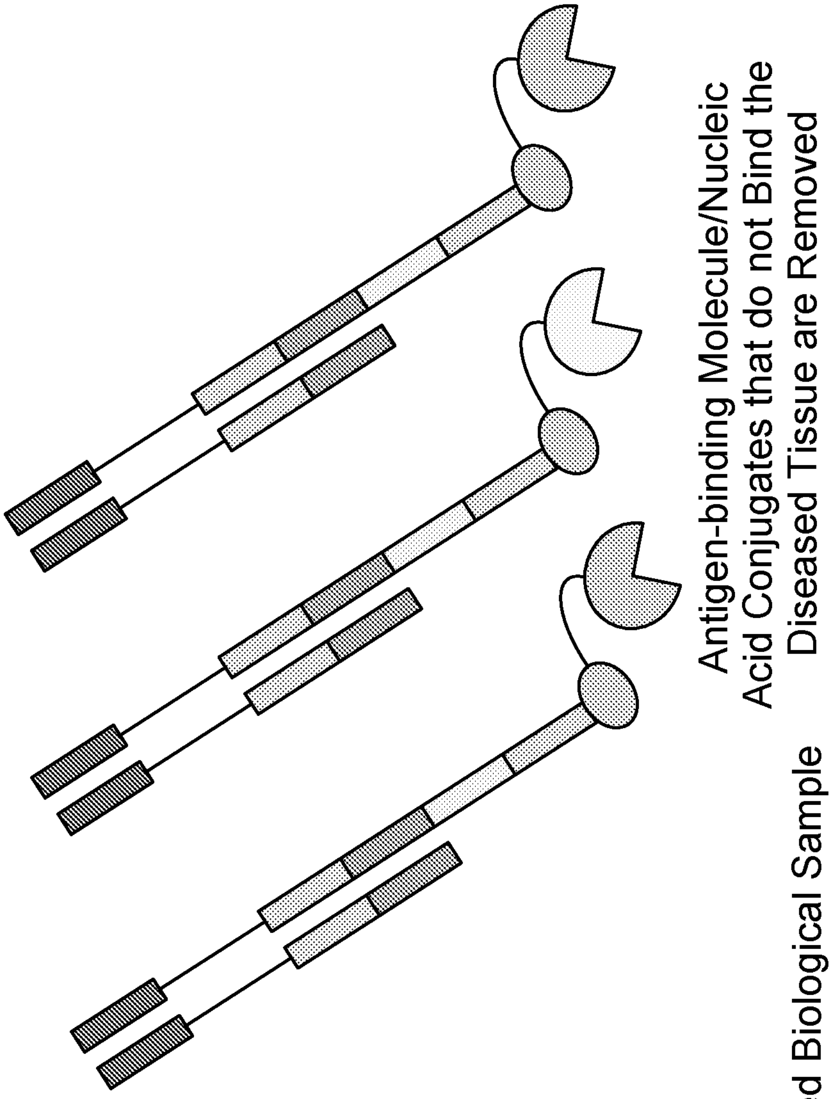
FIGS. 4A-B show non-binders from FIG. 3B binding to a diseased biological sample (FIG. 4A) and removal of non-binding antigen-binding molecule/nucleic acid conjugate members (FIG. 4B).
Figure 4A:
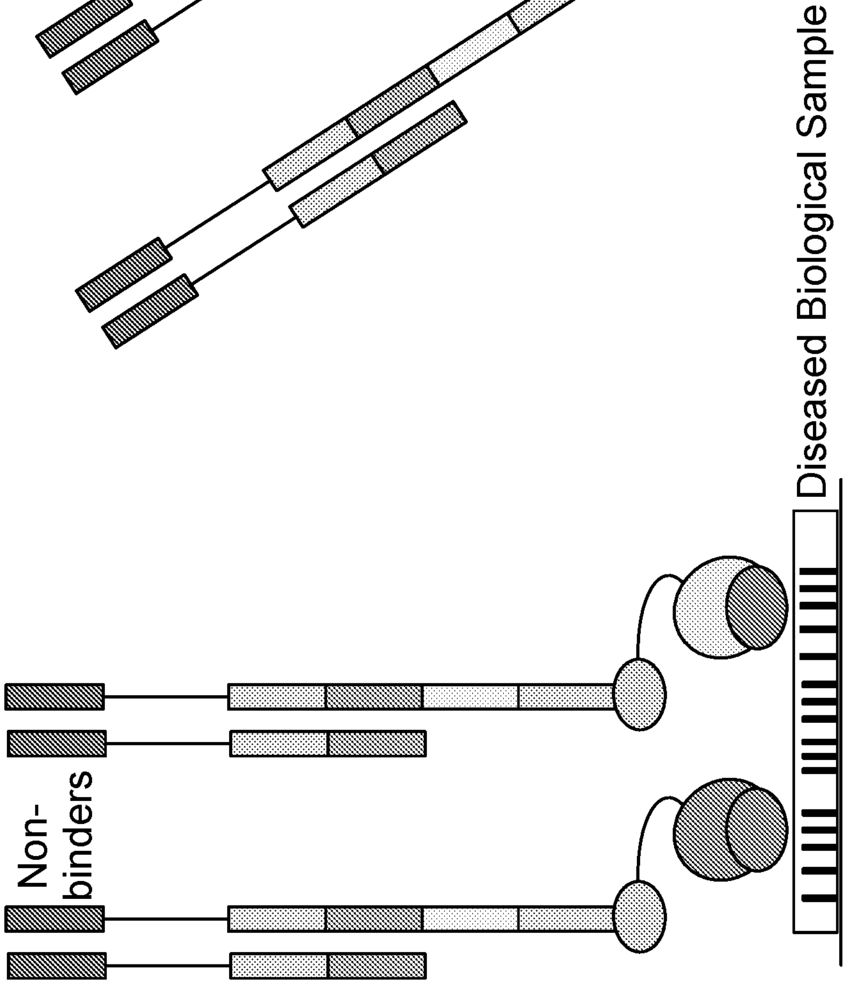

The non-binding antigen-binding molecule/nucleic acid conjugates collected in FIG. 3B can be screened against diseased biological samples. Thus, FIG. 4A shows such collected non-binding antigen-binding molecule/nucleic acid conjugates screened against a diseased biological sample. In some embodiments, one or more of the collected non-binding antigen-binding molecule/nucleic acid conjugates bind the diseased biological sample. In some embodiments, one or more of the collected non-binding antigen-binding molecule/nucleic acid conjugates do not bind the diseased biological sample. In some embodiments, the antigen-binding molecule/nucleic acid conjugates that do not bind a diseased biological sample are removed (e.g., washed off) from the diseased biological sample as shown in FIG. 4B.

In some embodiments, the synthesized cDNA, or a portion thereof, hybridizes to the binding antigen-binding molecule/nucleic acid conjugate members shown in FIG. 4A can be released (e.g., released with heat, treated with an RNase (e.g., any suitable RNase)) from the antigen-binding molecule/nucleic acid conjugate. In some embodiments, the released cDNA interacts with (e.g., hybridizes) the capture domain of a capture probe on array including a plurality of capture probes, where a capture probe includes a spatial barcode and a capture domain. For example, the cDNA includes an analyte capture sequence that binds to the capture domain. In some embodiments, no cDNA is synthesized (not shown). In such embodiments, the mRNA of the antigen-binding molecule/nucleic acid conjugate is directly captured (e.g., captured without the synthesis of the cDNA) by the capture probe on the array. In such embodiments, the orientation of the domains shown in FIG. 2A can be rearranged (e.g., rearranged as described herein) to facilitate direct capture of the mRNA of the antigen-binding molecule/nucleic acid conjugate.

In some embodiments, a capture probe (e.g., a capture probe including a spatial barcode) and a capture domain can bind (e.g., hybridize) with the released cDNA, or portion thereof, as shown in FIG. 5A. In some embodiments, the cDNA is the cDNA released (e.g., released by any of the methods described herein) from the antigen-binding molecule/nucleic acid conjugate members. In some embodiments, the cDNA is released via heat. In some embodiments, the cDNA is released via denaturation. In some embodiments, the cDNA is released via RNase digestion (e.g., digested by any of the RNases described herein). In some embodiments, the captured cDNA is extended using the capture probe as a template as shown in FIG. 5B. In some embodiments, the capture probe is extended using the captured cDNA as an extension template. In some embodiments, both the capture probe and the cDNA are extended using the cDNA and the capture probe, respectively, as an extension template.

FIG. 6A shows extension of the 3' end of the capture probe and the 3' end of the cDNA (FIG. 6A) from the antigen-binding molecule/nucleic acid conjugate. FIG. 6B shows the resulting nucleic acid library and potential downstream applications including amplifying the nucleic acid library and/or adding a promoter sequence (e.g., RNA polymerase promoter sequence, e.g., a T7, SP6 or T3 promoter sequence) to the nucleic acid library (or amplified nucleic acid library) for another round of antigen-binding molecule screening.

In some embodiments, the resulting nucleic acid library is amplified. In some embodiments, all or a portion of the resulting nucleic acid library (or amplified nucleic acid library) is sequenced according to known methods in the art to identify the antigen-binding molecule. In some embodiments, the resulting nucleic acid library (or amplified nucleic acid library) has a primer binding sequence added and is amplified for another round of antigen-binding molecule screening. In some embodiments, the resulting nucleic acid library (or amplified nucleic acid library) has a promoter sequence (e.g., RNA polymerase promoter sequence, e.g., a T7, SP6, or T3 promoter sequence) added and is amplified for another round of antigen-binding molecule screening.

Systems

As described herein, spatial analysis can be performed using dedicated hardware and/or software, such as any of the systems described in Sections (II)(e)(ii) and/or (V) of WO 2020/176788 and/or U.S. Patent Application Publication No. 2020/0277663, or any of one or more of the devices or methods described in Sections Control Slide for Imaging, Methods of Using Control Slides and Substrates for, Systems of Using Control Slides and Substrates for Imaging, and/or Sample and Array Alignment Devices and Methods, Informational labels of WO 2020/123320.

Suitable systems for performing spatial analysis can include components such as a chamber (e.g., a flow cell or sealable, fluid-tight chamber) for containing a biological sample. The biological sample can be mounted for example, in a biological sample holder. One or more fluid chambers can be connected to the chamber and/or the sample holder via fluid conduits, and fluids can be delivered into the chamber and/or sample holder via fluidic pumps, vacuum sources, or other devices coupled to the fluid conduits that create a pressure gradient to drive fluid flow. One or more valves can also be connected to fluid conduits to regulate the flow of reagents from reservoirs to the chamber and/or sample holder.

Thus, provided herein are systems including a) an antigen-binding molecule/nucleic acid conjugate produced by any of the methods described herein; and b) an array including a plurality of capture probes, wherein a capture probe of the plurality includes a capture domain that binds specifically (e.g., hybridizes) to the analyte capture domain and a spatial barcode. In some embodiments, the system includes reverse transcriptase.

In some embodiments, the system includes ribonucleotide triphosphates, deoxyribonucleotide triphosphates, and one or more buffers.

In some embodiments, the system includes one or more permeabilization reagents.

In some embodiments, the one or more permeabilization reagents includes an RNase, a DNase, a lipase, a protease, and combinations thereof.

In some embodiments, the capture probe includes one or more functional domains, a cleavage domain, a unique molecular identifier, and combinations thereof.

Compositions

The present disclosure also features compositions including antibody and/or antigen-binding molecule nucleic acid libraries and antigen-binding/nucleic acid conjugates generated therefrom.

Thus, provided herein are compositions including an in vitro transcribed mRNA in a 5' to 3' direction: (i) a sequence complementary to an analyte capture sequence that hybridized to a capture domain of a capture probe, (ii) a sequence encoding an antigen-binding molecule, (iii) a primer binding sequence, and (iv) a universal sequence. In some embodiments, the nucleic acid library is single-stranded. In some embodiments, the nucleic acid library is double-stranded.

In some embodiments, the composition includes a donor oligonucleotide attached to the universal sequence of the mRNA. In some embodiments, the donor oligonucleotide includes a linker having a sequence and a protein translation inhibitor. In some embodiments, the protein translation inhibitor includes a translation inhibitor molecule. In some embodiments, the translation inhibitor molecule includes puromycin. In some embodiments, the protein translation inhibitor does not include a stop codon. For example, the lack of a stop codon tethers the translated protein to its own mRNA non-covalently.

In some embodiments, the donor oligonucleotide is attached the universal sequence of the mRNA with a splint oligonucleotide. In some embodiments, the splint oligonucleotide includes a substantially complementary sequence to the universal domain and a substantially complementary sequence to the linker of the donor oligonucleotide.

In some embodiments, the nucleic acid library is transcribed (e.g., transcribed into mRNA). In some embodiments, a protein translation inhibitor molecule is attached to the transcribed mRNA. In some embodiments, a linker is disposed between the mRNA and the protein translation inhibitor molecule.

Also provided herein are compositions including an antigen-binding molecule/nucleic acid conjugate including (i) a sequence complementary to an analyte capture sequence, (ii) a sequence encoding an antigen-binding molecule, (iii) a primer binding sequence, (iv) a constant sequence; (v) a protein translation inhibitor molecule; and (vi) the antigen-binding molecule.

In some embodiments, the antigen-binding molecule includes a single-chain antigen binding molecule. In some embodiments, the single-chain antigen binding molecule includes an scFv. In some embodiments, the single-chain antigen binding molecule includes a nanobody.

In some embodiments, the composition further includes a cDNA hybridized to the nucleic acid of the antigen-binding molecule/nucleic acid conjugate. In some embodiments, the cDNA is generated by reverse transcription. For example, a complementary cDNA can be generated by reverse transcription to the nucleic acid portion of the antigen-binding molecule/nucleic acid conjugate.

Also provided herein are compositions including a) an array including a plurality of capture probes, where a capture probe includes: (i) a spatial barcode; and (ii) a capture domain; and b) a cDNA including in the 5' to 3' direction: (i) a sequence complementary to a universal domain; (ii) a sequence complementary to a primer binding site; (iii) a sequence complementary to a sequence encoding an antigen-binding molecule; and (iv) an analyte capture sequence, wherein the analyte capture sequence is bound to the capture domain of the capture probe.

Also provided herein are compositions including: a) an array including a plurality of capture probes, wherein a capture probe includes: (i) a spatial barcode; and (ii) a capture domain; and b) an extended cDNA product including in the 5' to 3' direction: (i) a sequence complementary to a universal domain; (ii) a sequence complementary to a primer binding site; (iii) a sequence complementary to a sequence encoding an antigen-binding molecule; (iv) an analyte capture sequence, where the analyte capture sequence is bound to the capture domain of the capture probe; (v) a sequence complementary the capture probe; and c) an extended capture probe including a sequence complementary to the cDNA using the cDNA as an extension template.

In some embodiments, the capture probe (e.g., any of the capture probes described herein) includes one or more functional domains, a unique molecular identifier, a cleavage domain, and combinations thereof.

Kits

In addition to the methods, systems, and compositions disclosed herein, the present disclosure also describes kits of the methods, systems, and compositions described herein. Thus, provided herein are kits including (i) a spatial array including a plurality of capture probes, wherein a capture probe of the plurality of capture probes includes a spatial barcode and a capture domain; (ii) a plurality of splint oligonucleotides; and (iii) a plurality of donor oligonucleotides, wherein a donor oligonucleotide of the plurality of donor oligonucleotides includes a universal domain, a linker, and a protein translation inhibitor.

In some embodiments, the kit includes a ligase (e.g., any of the ligases described herein).

In some embodiments, the kit includes one or more permeabilization reagents. In some embodiments, the one or more permeabilization reagents comprises an RNase, a DNase, a protease, a lipase, and combinations thereof.

In some embodiments, the kit includes one or more DNA polymerases. In some embodiments, the kit includes one or more reverse transcriptases. In some embodiments, the kit includes a template switch oligonucleotide.

In some embodiments, the protein translation inhibitor is puromycin.

In some embodiments, the kit includes a primer that binds to the universal domain.

EXAMPLES

Example 1. Generation of Antigen-Binding/Nucleic Acid Conjugate Library

FIGS. 2A-E show an exemplary single-chain antibody nucleic acid library (FIG. 2A) and an exemplary method of generating a display library via in vitro transcription of the single-chain antibody nucleic acid library (FIG. 2B-E). FIG. 2A shows a nucleic acid library where a member of the nucleic acid library includes in a 5' to 3' direction a primer binding sequence, an analyte capture sequence (e.g., an analyte capture sequence that binds to a capture domain) or a complement thereof, a sequence encoding a single-chain antibody or antigen-binding fragment, a second primer binding site and a universal domain. While FIG. 2A shows a double-stranded nucleic acid library, it is understood by those skilled in the art that the nucleic acid library can be a single-stranded nucleic acid library. FIG. 2B shows the resulting mRNA after in vitro transcription of a member of the nucleic acid library. FIG. 2C shows the mRNA of FIG. 2B ligated to a molecule including a linker and a protein translation inhibitor molecule. FIG. 2C shows the ligation facilitated by a splint oligonucleotide, although other methods of attaching the mRNA and the molecule including the linker and protein translation inhibitor molecule are known in the art, including Y-ligation and the TRAP system (as described herein), and the resulting antigen-binding molecule/nucleic acid conjugate (FIG. 2D). FIG. 2E shows a complementary cDNA synthesized to the nucleic acid portion of the antigen-binding/nucleic acid conjugate.

Example 2. Spatial Antibody or Antigen-Binding Fragment Screening

Antigen-binding molecule/nucleic acid conjugates generated in Example 1 are screened against healthy biological samples (e.g., a control biological sample) and non-binding antigen-binding molecule/nucleic acid conjugates are removed and collected for screening against diseased (e.g., tumor) biological samples. For example, FIGS. 3A-B show exemplary antigen-binding molecule/nucleic acid conjugate members generated in Example 1 binding to an antigen in a biological sample (FIG. 3A). FIG. 3A shows binding to a control biological sample (e.g., a healthy biological sample) and removal and collection of non-binding antigen-binding molecule/nucleic acid conjugate members (FIG. 3B).

As shown in FIGS. 4A-B non-binding antigen-binding molecule/nucleic acid conjugate members collected in FIG. 3B are assessed for binding to a diseased biological sample (FIG. 4A). Non-binding antigen-binding molecule/nucleic acid conjugate members are removed from the biological sample (e.g., washed off) (FIG. 4B).

The synthesized cDNA, or a portion thereof, hybridized to the binding antigen-binding molecule/nucleic acid conjugate members shown in FIG. 4A is released (e.g., released with heat, treated with an RNase (e.g., any RNase described herein)) from the antigen-binding molecule/nucleic acid conjugate. The released cDNA binds with (e.g., hybridizes) to the capture domain of a capture probe on array including a plurality of capture probes, where a capture probe includes a spatial barcode and a capture domain. For example, the cDNA includes an analyte capture sequence that binds to the capture domain.

FIGS. 5A-B show a capture probe (e.g., the capture domain of a capture probe) hybridized to the analyte capture sequence of the cDNA from the antigen-binding molecule/nucleic acid conjugate members (FIG. 5A). FIG. 5B shows extension of the 3' end of the capture probe and the 3' end of the cDNA.

FIGS. 6A-B show extension of the 3' end of the capture probe and the 3' end of the cDNA (FIG. 6A) and the resulting nucleic acid library in FIG. 6B. In some examples, the resulting nucleic acid library is sequenced according to known methods in the art to identify the antigen-binding molecule. In some examples, the resulting nucleic acid library has a primer binding sequence added and is amplified for another round of antigen-binding molecule screening as described herein.

What is claimed is:

1. A method of identifying an antigen-binding molecule that selectively binds to an antigen in a biological sample, the method comprising:

a) providing an array comprising a plurality of capture probes, wherein a capture probe of the plurality of capture probes comprises: (i) a spatial barcode and (ii) a capture domain;

b) contacting the biological sample with members of an antigen-binding molecule/nucleic acid conjugate library, wherein an antigen-binding molecule/nucleic acid conjugate of the library comprises an antigen-binding molecule linked to a nucleic acid encoding the antigen-binding molecule, and wherein the nucleic acid comprises a cDNA/RNA duplex, wherein the RNA of the cDNA/RNA duplex comprises:

i) a sequence complementary to an analyte capture sequence which hybridizes to the capture domain of the capture probe(s), ii) a sequence encoding an antigen-binding molecule, iii) a primer binding sequence, and iv) a universal domain attached to a donor oligonucleotide, wherein the donor oligonucleotide comprises a linker having a nucleotide sequence and a protein translation inhibitor;

c) hybridizing the analyte capture sequence of one or more cDNAs of the antigen-binding molecule/nucleic acid conjugates with the capture domain of the capture probe(s) on the array; and d) determining (i) the sequence of the spatial barcode or a complement thereof, and (ii) all or a portion of the sequence of the cDNA, or a complement thereof and using the determined sequences of (i) and (ii) to identify an antigen-binding molecule that selectively binds to an antigen in the biological sample.

2. The method of claim 1, further comprising using the determined sequences of (i) and (ii) to determine a location of the antigen in the biological sample.

3. The method of claim 1, wherein the determining comprises sequencing.

4. The method of claim 1, further comprising removing one or more unhybridized antigen-binding molecule/nucleic acid conjugates from the biological sample.

5. The method of claim 1, wherein the members of the antigen-binding molecule/nucleic acid conjugate library were selected by a prior step of contacting a control biological sample with the antigen-binding molecule/nucleic acid conjugate library, and selecting members of the library that did not bind to the control biological sample.

6. The method of claim 5, wherein the control biological sample is a healthy biological sample.

7. The method of claim 1, wherein the biological sample comprises one or more healthy regions and one or more disease regions or wherein the biological sample is a diseased biological sample, optionally, wherein the diseased biological sample is a tumorous biological sample.

8. The method of claim 1, wherein the method further comprises releasing the one or more cDNAs from the antigen-binding molecule/nucleic acid conjugate prior to the hybridization step.

9. The method of claim 8, wherein the releasing comprises an RNase, wherein the RNase is selected from the group consisting of RNase A, RNase C, RNase H, or RNase I or heat, or both.

10. The method of claim 1, wherein the method further comprises permeabilizing the biological sample.

11. The method of claim 1, wherein the method further comprises imaging the biological sample and/or staining the biological sample, optionally, wherein the staining comprises hematoxylin and/or eosin.

12. The method claim 1, wherein the capture probes comprise a cleavage domain, a unique molecular identifier (UMI), one or more functional domains, or combinations thereof.

13. The method of claim 1, wherein the antigen-binding molecule is a single-chain antigen-binding molecule.

14. The method of claim 13, wherein the single-chain antigen-binding molecule comprises a single-chain variable fragment (scFv) or a single variable domain on a heavy chain antibody.

15. The method of claim 1, wherein the method further comprises hybridizing a nucleic acid analyte from the biological sample to the capture domain of the capture probe(s).

16. The method of claim 1, wherein the method further comprises:

(a) contacting a first probe and a second probe with the biological sample, wherein the first probe and the second probe each comprise sequences that are substantially complementary to sequences of a nucleic acid analyte, and wherein the second probe comprises a capture probe capture domain that is complementary to all or a portion of the capture domain;

(b) hybridizing the first probe and the second probe to the nucleic acid analyte;

(c) generating a ligation product by ligating the first probe and the second probe;

(d) releasing the ligation product from the nucleic acid analyte;

(e) hybridizing the capture probe capture domain of the ligation product to the capture domain; and (f) determining the sequence of (i) all or a portion of the ligation product, or a complement thereof, and (ii) the spatial barcode, or a complement thereof, and using the determined sequences of (i) and (ii) to identify a location of the nucleic acid analyte in the biological sample.

17. The method of claim 1, wherein the method further comprises identifying the antigen bound by the antigen-binding molecule/nucleic acid complex, optionally, wherein the identifying comprises mass spectrometry.

18. The method of claim 1, wherein the identifying further comprises determining differential gene expression patterns within the biological sample.

19. The method of claim 1, wherein the biological sample is disposed on the array comprising the plurality of capture probes.

20. The method of claim 1, wherein the biological sample is disposed on a substrate the method further comprises aligning the substrate with the array, such that at least a portion of the biological sample is aligned with at least a portion of the array.

* * * * *